US008918724B2

(12) United States Patent
Sitrick et al.

(10) Patent No.: US 8,918,724 B2
(45) Date of Patent: *Dec. 23, 2014

(54) SYSTEMS AND METHODOLOGIES PROVIDING CONTROLLED VOICE AND DATA COMMUNICATION AMONG A PLURALITY OF COMPUTING APPLIANCES ASSOCIATED AS TEAM MEMBERS OF AT LEAST ONE RESPECTIVE TEAM OR OF A PLURALITY OF TEAMS AND SUB-TEAMS WITHIN THE TEAMS

(75) Inventors: David H. Sitrick, Highland Park, IL (US); Russell T. Fling, Naperville, IL (US)

(73) Assignee: David H. Sitrick, Los Angeles, CA (US)

( * ) Notice: Subject to any disclaimer, the term of this patent is extended or adjusted under 35 U.S.C. 154(b) by 201 days.
This patent is subject to a terminal disclaimer.

(21) Appl. No.: 13/102,908

(22) Filed: May 6, 2011

(65) Prior Publication Data
US 2012/0284645 A1    Nov. 8, 2012

(51) Int. Cl.
*G06F 3/00* (2006.01)
*G06Q 10/10* (2012.01)
*G06Q 50/20* (2012.01)
*G06Q 50/22* (2012.01)
*G06F 17/24* (2006.01)

(52) U.S. Cl.
CPC .............. *G06Q 10/101* (2013.01); *G06Q 50/20* (2013.01); *G06Q 50/22* (2013.01); *G06F 17/241* (2013.01)
USPC ........... 715/751; 715/762; 715/763; 715/765; 715/853

(58) Field of Classification Search
CPC ..................................................... G06F 17/241
USPC ................................................... 715/753, 741
See application file for complete search history.

(56) References Cited

U.S. PATENT DOCUMENTS 3,648,245 A    3/1972 Dodds, Jr. et al.
3,955,466 A    5/1976 Goldmark
(Continued)

FOREIGN PATENT DOCUMENTS

DE    3839361    5/1990
DE    4200673    7/1993
(Continued)

OTHER PUBLICATIONS

Ditlow et al., "Paging of Display Screen Images Using Footswitch and Digital Interface," IBM Technical Disclosure Bulletin, Jan. 1, 1989, pp. 252-254.

(Continued)

*Primary Examiner* — William Titcomb

(57) ABSTRACT

A system and methodology for communication and collaboration among a plurality of computing appliances associated as team members. The system is comprised of: at least one local communication means for use by at least one local team member, and conveying data (preferably media data and collaboration data); at least one other communication means for use by at least one other team member, and conveying data. Gateway means conveys data between each of the communication means. Network means links said at least one local communication means, and, said at least one other communication means, and enables the conveyance of the data. Display means provides a display presentation of a display image of display image data, for viewing by respective users at each of said at least one local communication means and said at least one other communication means. Input means provides annotation data representative of a respective user providing an input of annotations made relative to viewing the display of the common base image at a respective display apparatus at each of said at both the communication means (local and other). Storage means stores the annotation data as associated with the respective user at each of said local and said other communication means. Selection means permits selection as to which of the annotation data is selected annotation data. A display apparatus provides a combined display presentation responsive to the display image data and to the selected annotation data.

35 Claims, 38 Drawing Sheets

(56) References Cited

U.S. PATENT DOCUMENTS

| | | |
|---|---|---|
| 4,012,979 A | 3/1977 | Wemekamp |
| 4,260,229 A | 4/1981 | Bloomstein |
| 4,350,070 A | 9/1982 | Bahu |
| 4,386,551 A | 6/1983 | Morgando |
| 4,468,204 A | 8/1984 | Scott et al. |
| 4,484,507 A | 11/1984 | Nakada et al. |
| 4,500,879 A | 2/1985 | Smith, III et al. |
| 4,521,014 A | 6/1985 | Sitrick |
| 4,527,980 A | 7/1985 | Miller |
| 4,547,851 A | 10/1985 | Kurland |
| 4,553,222 A | 11/1985 | Kurland et al. |
| 4,572,509 A | 2/1986 | Sitrick |
| 4,591,928 A | 5/1986 | Bloom et al. |
| 4,646,609 A | 3/1987 | Teruo et al. |
| 4,688,105 A | 8/1987 | Bloch et al. |
| 4,694,723 A | 9/1987 | Shinohara et al. |
| 4,698,460 A | 10/1987 | Krein et al. |
| 4,698,461 A | 10/1987 | Meadaws et al. |
| 4,707,845 A | 11/1987 | Krein et al. |
| 4,745,836 A | 5/1988 | Dannenberg |
| 4,766,581 A | 8/1988 | Korn et al. |
| 4,779,510 A | 10/1988 | Van den Abbeel |
| 4,823,367 A | 4/1989 | Kreutzfeld |
| 4,827,532 A | 5/1989 | Bloomstein |
| 4,843,568 A | 6/1989 | Krueger et al. |
| 4,942,551 A | 7/1990 | Kappert et al. |
| 4,976,182 A | 12/1990 | Obuchi et al. |
| 5,001,632 A | 3/1991 | Hall-Tipping |
| 5,002,491 A | 3/1991 | Abrahamson et al. |
| 5,046,004 A | 9/1991 | Tsumura et al. |
| 5,053,757 A | 10/1991 | Meadows |
| 5,054,360 A | 10/1991 | Lisle et al. |
| 5,107,443 A | 4/1992 | Smith et al. |
| 5,117,726 A | 6/1992 | Lisle et al. |
| 5,126,639 A | 6/1992 | Srivastava |
| 5,136,146 A | 8/1992 | Anglin et al. |
| 5,142,620 A | 8/1992 | Watanabe et al. |
| 5,146,833 A | 9/1992 | Lui |
| 5,148,154 A | 9/1992 | Mackay et al. |
| 5,149,104 A | 9/1992 | Edelstein |
| 5,153,829 A | 10/1992 | Furuya et al. |
| 5,166,463 A | 11/1992 | Weber |
| 5,176,520 A | 1/1993 | Hamilton |
| 5,194,682 A | 3/1993 | Okamura et al. |
| 5,204,969 A | 4/1993 | Capps et al. |
| 5,225,618 A | 7/1993 | Wadhams |
| 5,240,417 A | 8/1993 | Smithson et al. |
| 5,247,126 A | 9/1993 | Okamura et al. |
| 5,250,747 A | 10/1993 | Tsumura |
| 5,270,475 A | 12/1993 | Weiss et al. |
| 5,315,911 A | 5/1994 | Ochi |
| 5,341,133 A | 8/1994 | Savoy et al. |
| 5,400,687 A | 3/1995 | Ishii |
| 5,488,196 A | 1/1996 | Zimmerman et al. |
| 5,521,323 A | 5/1996 | Paulson et al. |
| 5,553,864 A | 9/1996 | Sitrick |
| 5,590,282 A | 12/1996 | Clynas |
| 5,604,322 A | 2/1997 | Kikuchi |
| 5,665,927 A | 9/1997 | Taki et al. |
| 5,689,077 A | 11/1997 | Jasinski |
| 5,728,960 A | 3/1998 | Sitrick |
| 5,728,962 A | 3/1998 | Goede |
| 5,760,323 A | 6/1998 | Romero et al. |
| 5,801,694 A | 9/1998 | Gershen |
| 5,830,065 A | 11/1998 | Sitrick |
| 5,952,597 A | 9/1999 | Weinstock et al. |
| 6,084,168 A | 7/2000 | Sitrick |
| 6,425,825 B1 | 7/2002 | Sitrick |
| 6,508,706 B2 | 1/2003 | Sitrick |
| 6,662,210 B1 | 12/2003 | Carleton et al. |
| 6,675,205 B2 | 1/2004 | Meadway et al. |
| 6,687,878 B1 | 2/2004 | Eintracht et al. |
| 6,785,676 B2 * | 8/2004 | Oblinger ................. 1/1 |
| 7,074,999 B2 | 7/2006 | Sitrick et al. |
| 7,098,392 B2 | 8/2006 | Sitrick et al. |
| 7,137,892 B2 | 11/2006 | Sitrick |
| 7,157,638 B1 | 1/2007 | Sitrick |
| 7,297,856 B2 | 11/2007 | Sitrick |
| 7,353,252 B1 | 4/2008 | Yang et al. |
| 7,418,656 B1 | 8/2008 | Petersen |
| 7,423,213 B2 | 9/2008 | Sitrick |
| 7,536,637 B1 | 5/2009 | Nauerz et al. |
| 7,612,278 B2 | 11/2009 | Sitrick et al. |
| 7,620,902 B2 * | 11/2009 | Manion et al. ................. 715/758 |
| 7,647,306 B2 * | 1/2010 | Rose et al. ............. 707/999.003 |
| 7,689,682 B1 * | 3/2010 | Eldering et al. ............... 709/223 |
| 7,734,692 B1 | 6/2010 | Kaplan et al. |
| 7,792,903 B2 * | 9/2010 | Fischer et al. ................. 709/205 |
| 7,809,791 B2 | 10/2010 | Schwartz et al. |
| 7,827,488 B2 | 11/2010 | Sitrick |
| 7,867,086 B2 | 1/2011 | Sitrick |
| 7,899,915 B2 | 3/2011 | Reisman |
| 7,975,215 B2 | 7/2011 | Duncan et al. |
| 7,989,689 B2 | 8/2011 | Sitrick et al. |
| 8,005,835 B2 * | 8/2011 | Walther et al. ................. 707/736 |
| 8,108,778 B2 | 1/2012 | Athsani et al. |
| 8,131,866 B2 | 3/2012 | Samra et al. |
| 8,132,094 B1 | 3/2012 | Bryar et al. |
| 8,196,051 B2 * | 6/2012 | Zaner et al. .................... 715/758 |
| 8,201,094 B2 | 6/2012 | Wang et al. |
| 8,209,618 B2 * | 6/2012 | Garofalo ........................ 715/753 |
| 8,214,749 B2 * | 7/2012 | Feinberg et al. .............. 715/753 |
| 8,234,688 B2 * | 7/2012 | Grandison et al. ................. 726/1 |
| 8,261,182 B1 | 9/2012 | Petersen |
| 8,347,207 B2 | 1/2013 | Borgsmidt et al. |
| 8,418,055 B2 | 4/2013 | King et al. |
| 2003/0009756 A1 | 1/2003 | Moir |
| 2003/0112467 A1 | 6/2003 | McCollum et al. |
| 2003/0113100 A1 | 6/2003 | Hecht et al. |
| 2003/0227479 A1 * | 12/2003 | Mizrahi et al. ................. 345/753 |
| 2005/0041872 A1 | 2/2005 | Yim et al. |
| 2005/0080859 A1 | 4/2005 | Lake |
| 2005/0102245 A1 | 5/2005 | Edlund et al. |
| 2005/0102356 A1 | 5/2005 | Manion et al. |
| 2005/0171799 A1 | 8/2005 | Hull et al. |
| 2005/0172001 A1 | 8/2005 | Zaner et al. |
| 2005/0198031 A1 | 9/2005 | Pezaris et al. |
| 2005/0198173 A1 | 9/2005 | Evans |
| 2005/0235038 A1 | 10/2005 | Donatella et al. |
| 2006/0048092 A1 | 3/2006 | Kirkley et al. |
| 2006/0059253 A1 | 3/2006 | Goodman et al. |
| 2007/0050360 A1 | 3/2007 | Hull et al. |
| 2007/0061487 A1 | 3/2007 | Moore et al. |
| 2007/0143663 A1 | 6/2007 | Hansen et al. |
| 2008/0092239 A1 * | 4/2008 | Sitrick et al. ..................... 726/27 |
| 2008/0092240 A1 * | 4/2008 | Sitrick et al. ..................... 726/27 |
| 2008/0109737 A1 | 5/2008 | Schaeffer et al. |
| 2008/0148067 A1 * | 6/2008 | Sitrick et al. .................. 713/193 |
| 2008/0163379 A1 | 7/2008 | Robinson et al. |
| 2009/0048927 A1 | 2/2009 | Gross |
| 2009/0055477 A1 | 2/2009 | Flesher et al. |
| 2009/0063991 A1 | 3/2009 | Baron et al. |
| 2009/0063995 A1 | 3/2009 | Baron et al. |
| 2009/0193327 A1 | 7/2009 | Roychoudhuri et al. |
| 2009/0254843 A1 | 10/2009 | VanWie et al. |
| 2009/0265607 A1 | 10/2009 | Raz et al. |
| 2009/0307762 A1 | 12/2009 | Cudd, Jr. |
| 2009/0320073 A1 | 12/2009 | Reisman |
| 2010/0030578 A1 | 2/2010 | Siddique et al. |
| 2010/0042511 A1 | 2/2010 | Sundaresan et al. |
| 2010/0083169 A1 | 4/2010 | Athsani et al. |
| 2010/0146060 A1 | 6/2010 | Graham |
| 2010/0151431 A1 | 6/2010 | Miller |
| 2010/0199191 A1 | 8/2010 | Takahashi |
| 2010/0262659 A1 | 10/2010 | Christiansen et al. |
| 2010/0263004 A1 | 10/2010 | Barton et al. |
| 2010/0278453 A1 * | 11/2010 | King ........................ 382/321 |
| 2011/0029883 A1 | 2/2011 | Lussier et al. |
| 2011/0030031 A1 | 2/2011 | Lussier et al. |
| 2011/0066942 A1 | 3/2011 | Barton et al. |
| 2011/0066944 A1 | 3/2011 | Barton et al. |
| 2011/0067066 A1 | 3/2011 | Barton et al. |
| 2011/0067099 A1 | 3/2011 | Barton et al. |
| 2011/0078590 A1 | 3/2011 | Hao et al. |

(56) References Cited

U.S. PATENT DOCUMENTS

| | | |
|---|---|---|
| 2011/0107369 A1 | 5/2011 | O'Brien et al. |
| 2011/0118619 A1 | 5/2011 | Burton et al. |
| 2011/0154192 A1 | 6/2011 | Yang et al. |
| 2011/0181496 A1 | 7/2011 | Lanier et al. |
| 2011/0181780 A1 | 7/2011 | Barton |
| 2011/0183654 A1 | 7/2011 | Lanier et al. |
| 2011/0184862 A1 | 7/2011 | Lanier et al. |
| 2011/0185036 A1 | 7/2011 | Lanier et al. |
| 2011/0185296 A1 | 7/2011 | Lanier et al. |
| 2011/0185312 A1 | 7/2011 | Lanier et al. |
| 2011/0239142 A1 | 9/2011 | Steeves et al. |
| 2011/0252320 A1 | 10/2011 | Arrasvuori et al. |
| 2011/0252339 A1 | 10/2011 | Lemonik et al. |
| 2012/0102409 A1* | 4/2012 | Fan et al. ............ 715/738 |
| 2012/0144346 A1 | 6/2012 | Meredith et al. |
| 2012/0174006 A1 | 7/2012 | Brownell et al. |
| 2012/0210247 A1 | 8/2012 | Khouri et al. |
| 2012/0231441 A1 | 9/2012 | Parthasarathy et al. |
| 2012/0233544 A1 | 9/2012 | Roy |

FOREIGN PATENT DOCUMENTS

| | | |
|---|---|---|
| FR | 2670599 | 6/1992 |
| FR | 2762130 | 10/1998 |
| GB | 2279493 | 1/1995 |
| GB | 2293915 | 4/1996 |
| JP | 60-253082 | 12/1985 |
| JP | 01-099169 | 4/1989 |
| JP | 01-113785 | 5/1989 |
| JP | 05-073042 | 3/1993 |
| JP | 06-004071 | 1/1994 |
| JP | 06-274158 | 3/1994 |
| JP | 07-020858 | 1/1995 |
| JP | 08-115081 | 5/1996 |
| JP | 08-123416 | 5/1996 |
| JP | 09-034446 | 2/1997 |
| JP | 09-097057 | 4/1997 |
| JP | 09-114453 | 5/1997 |
| JP | 09-244524 | 9/1997 |
| WO | WO 94/10680 | 5/1994 |

OTHER PUBLICATIONS

Dasna, Orya et al., "Muse: Digital Music Stand for Symphony Musicians," Interactions Design Awards, May/Jun. 1996, pp. 27-35.

Graefe, Christopher et al., "Designing the Muse: A Digital Music Stand for the Symphony Musician," Apr. 13-18, 1996, pp. 436-441 and 521-524, Design Briefings, ACM/SIGCHI.

Conference on Human Factors in Computing, Systems, Vancouver, British Columbia, Canada, CHI 96, Apr. 13-18, 1996.

Finale: "The Art of Music Notation," 1992, vol. 2 Encyclopedia, 3.0 for Macintosh, 308 pages, Coda Music Software, Eden Prairie, Minnesota.

\* cited by examiner

Fig 11

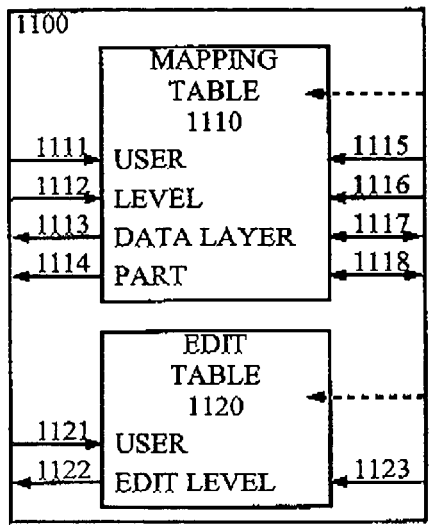

1130 Mapping Table Data Example

| USER | LEVEL | DATA LAYER | PART |
|---|---|---|---|
| A | 1 | DATA LAYER 2 | PAGE 1 |
| A | 0 | DATA LAYER 1 | PAGE 1 |
| B | 1 | DATA LAYER 3 | PAGE 2 |
| B | 0 | DATA LAYER 1 | PAGE 2 |
| C | 3 | DATA LAYER 2 | PAGE 1 |
| C | 2 | DATA LAYER 4 | PAGE 1 |
| C | 1 | DATA LAYER 3 | PAGE 1 |
| C | 0 | DATA LAYER 1 | PAGE 1 |

1140 Edit Table Data Example

| USER | EDIT LEVEL |
|---|---|
| A | 1 |
| B | 1 |
| C | 2 |

Fig 12

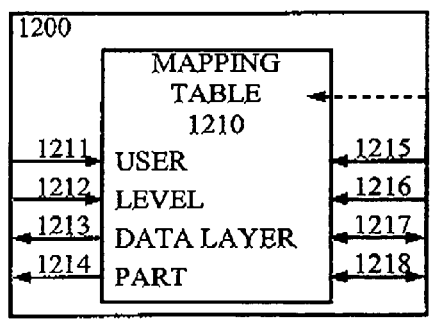

1230 Mapping Table Data Example

| USER | LEVEL | DATA LAYER | PART |
|---|---|---|---|
| A | 1 | DATA LAYER 2 | PAGE 1 |
| A | 0 | DATA LAYER 1 | PAGE 1 |
| B | 1 | DATA LAYER 3 | PAGE 2 |
| B | 0 | DATA LAYER 1 | PAGE 2 |
| C | 3 | DATA LAYER 2 | PAGE 1 |
| C | 2 | DATA LAYER 4 | PAGE 1 |
| C | 1 | DATA LAYER 3 | PAGE 1 |
| C | 0 | DATA LAYER 1 | PAGE 1 |

Fig 13

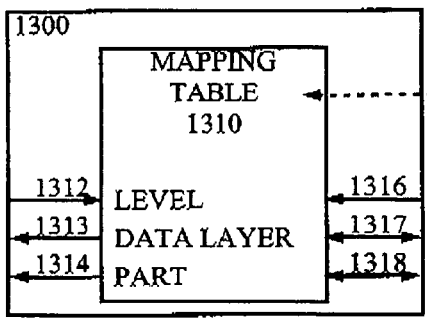

| 1330 Mapping Table Data Example for User C ||| 
|---|---|---|
| LEVEL | DATA LAYER | PART |
| 3 | DATA LAYER 2 | PAGE 1 |
| 2 | DATA LAYER 4 | PAGE 1 |
| 1 | DATA LAYER 3 | PAGE 1 |
| 0 | DATA LAYER 1 | PAGE 1 |

1331 Mapping Table Data Example for User B

| LEVEL | DATA LAYER | PART |
|---|---|---|
| 1 | DATA LAYER 3 | PAGE 2 |
| 0 | DATA LAYER 1 | PAGE 2 |

1332 Mapping Table Data Example for User A

| LEVEL | DATA LAYER | PART |
|---|---|---|
| 1 | DATA LAYER 2 | PAGE 1 |
| 0 | DATA LAYER 1 | PAGE 1 |

Fig 14

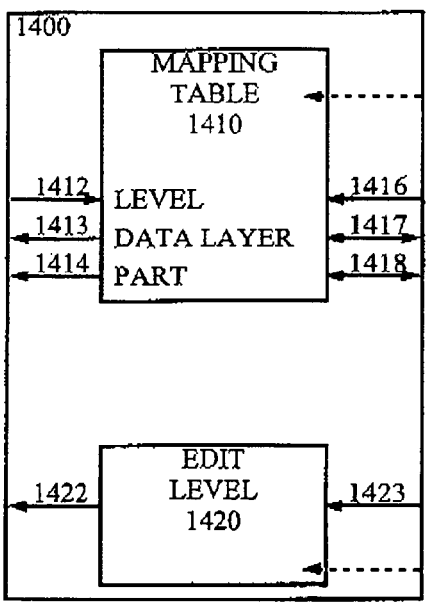

1430 Mapping Table Data Example for User C

| LEVEL | DATA LAYER | PART |
|---|---|---|
| 3 | DATA LAYER 2 | PAGE 1 |
| 2 | DATA LAYER 4 | PAGE 1 |
| 1 | DATA LAYER 3 | PAGE 1 |
| 0 | DATA LAYER 1 | PAGE 1 |

1431 Mapping Table Data Example for User B

| LEVEL | DATA LAYER | PART |
|---|---|---|
| 1 | DATA LAYER 3 | PAGE 2 |
| 0 | DATA LAYER 1 | PAGE 2 |

1432 Mapping Table Data Example for User A

| LEVEL | DATA LAYER | PART |
|---|---|---|
| 1 | DATA LAYER 2 | PAGE 1 |
| 0 | DATA LAYER 1 | PAGE 1 |

1440 Edit Table Data Example for User C

| EDIT LEVEL |
|---|
| 2 |

1441 Edit Table Data Example for User B

| EDIT LEVEL |
|---|
| 1 |

1442 Edit Table Data Example for User A

| EDIT LEVEL |
|---|
| 1 |

APPLIANCE DATA NETWORK

FIG. 22
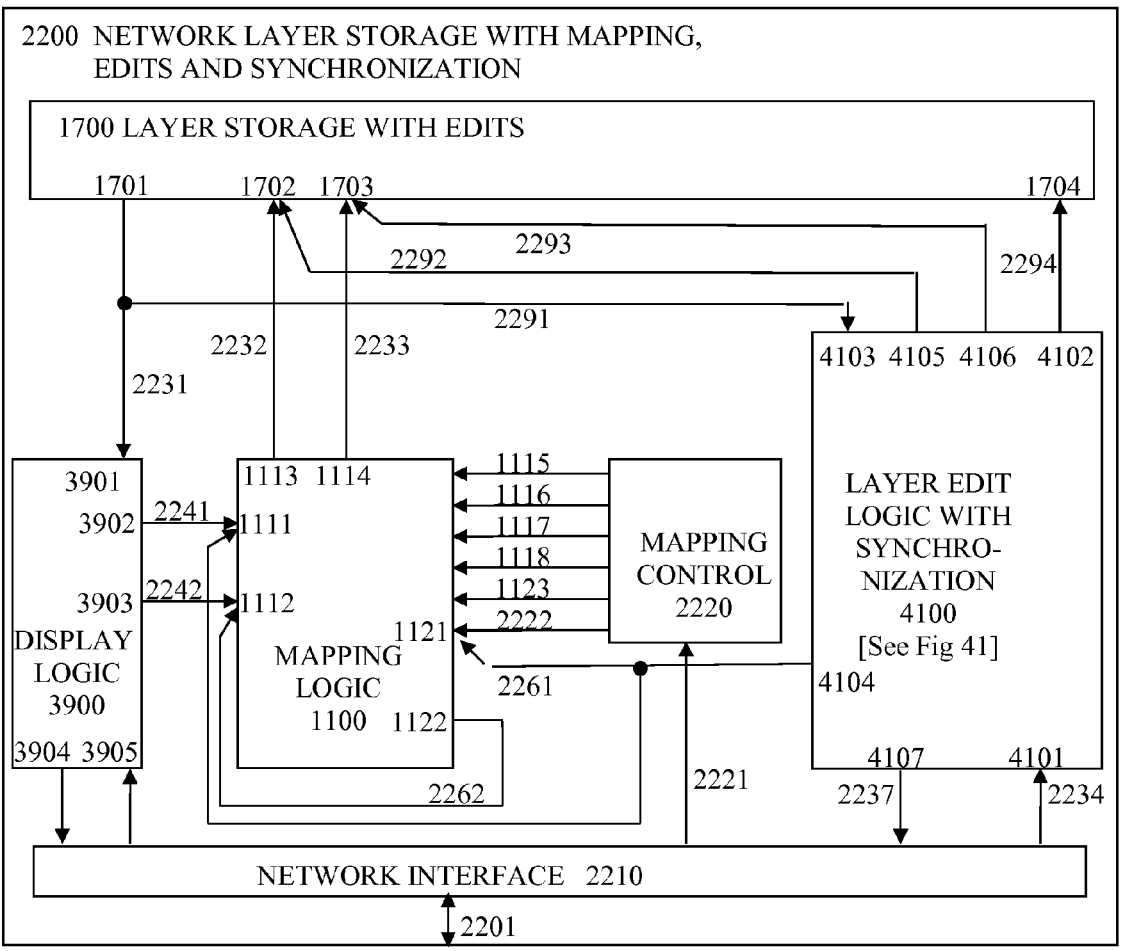
FIG. 23
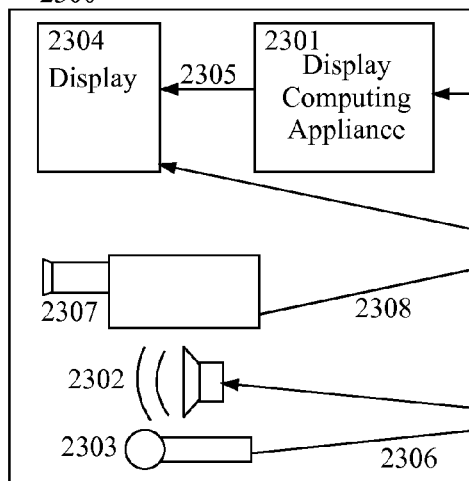
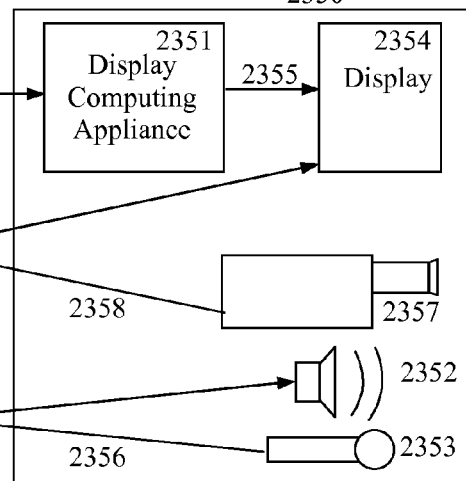

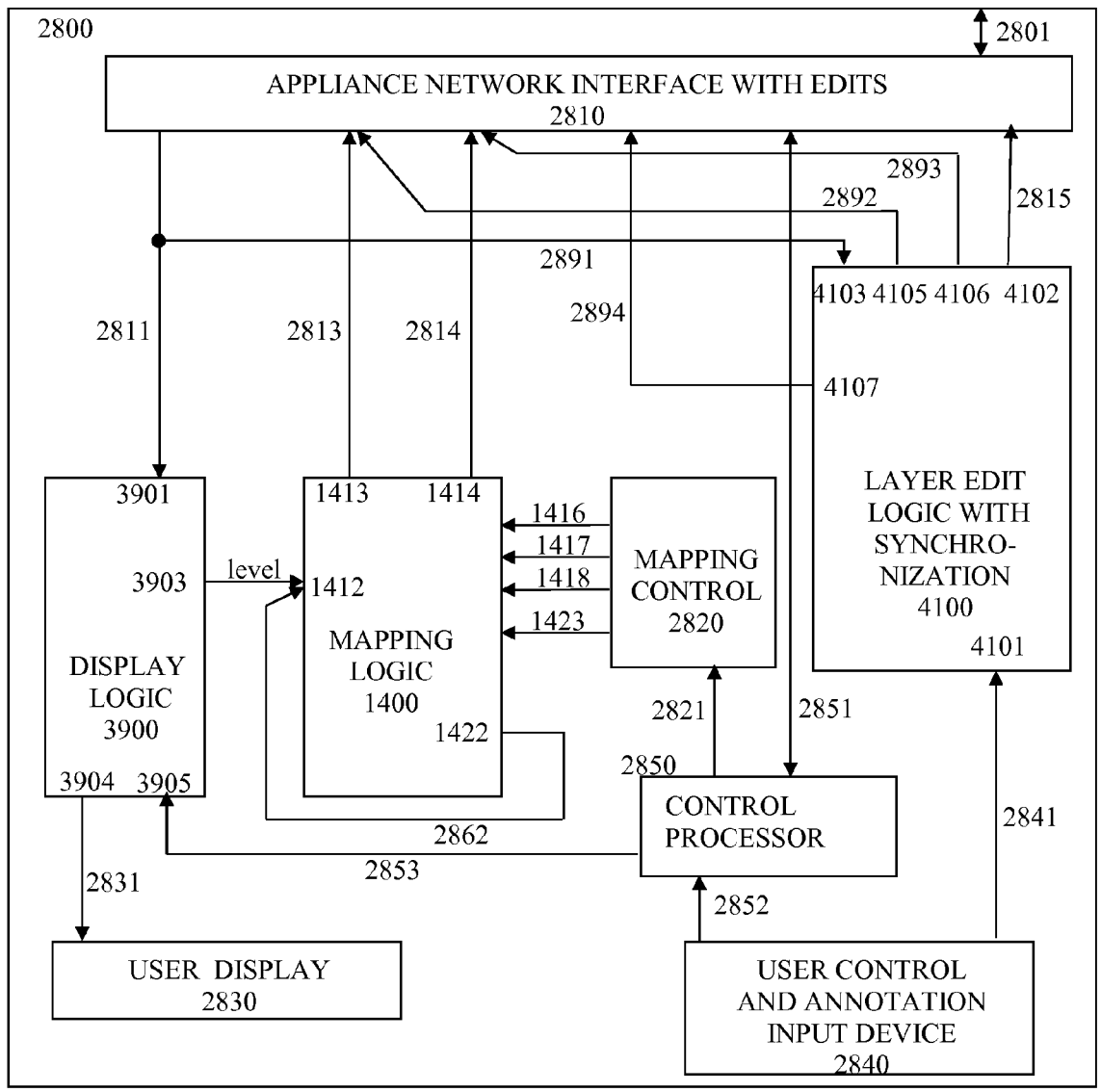

FIG. 29

LEADER 1 MAPPING LOGIC

Mapping Table

| Level | Layer | Part |
|---|---|---|
| 4 | LEADER 1 | PAGE 1 |
| 3 | LEADER 2 | PAGE 1 |
| 2 | OPTIONAL 1 | PAGE 1 |
| 1 | OPTIONAL 2 | PAGE 1 |
| 0 | COMMON | PAGE 1 |

| Edit Level |
|---|
| 4 |

MEMBER 3 MAPPING LOGIC

Mapping Table

| Level | Layer | Part |
|---|---|---|
| 4 | MEMBER 3 | PAGE 3 |
| 3 | LEADER 1 | PAGE 3 |
| 2 | LEADER 2 | PAGE 3 |
| 1 | OPTIONAL 3 | PAGE 3 |
| 0 | COMMON | PAGE 3 |

| Edit Level |
|---|
| 4 |

LEADER 2 MAPPING LOGIC

Mapping Table

| Level | Layer | Part |
|---|---|---|
| 2 | LEADER 2 | PAGE 5 |
| 1 | LEADER 1 | PAGE 5 |
| 0 | COMMON | PAGE 5 |

| Edit Level |
|---|
| 2 |

MEMBER 4 MAPPING LOGIC

Mapping Table

| Level | Layer | Part |
|---|---|---|
| 3 | MEMBER 4 | PAGE 5 |
| 2 | LEADER 1 | PAGE 5 |
| 1 | LEADER 2 | PAGE 5 |
| 0 | COMMON | PAGE 5 |

| Edit Level |
|---|
| 3 |

FIG. 32

TEACHER MAPPING LOGIC IN
TEACHER MODE

| Mapping Table | | |
|---|---|---|
| Level | Layer | Part |
| 1 | TEACHER | LESSON 6 |
| 0 | COMMON | LESSON 6 |

| Edit Level |
|---|
| 1 |

STUDENT Y MAPPING LOGIC

| Mapping Table | | |
|---|---|---|
| Level | Layer | Part |
| 2 | STUDENT Y | LESSON 6 |
| 1 | TEACHER | LESSON 6 |
| 0 | COMMON | LESSON 6 |

| Edit Level |
|---|
| 2 |

TEACHER MAPPING LOGIC IN
MULTI-MODE

| Mapping Table | | |
|---|---|---|
| Level | Layer | Part |
| ... | more students | LESSON 6 |
| 4 | STUDENT 3 | LESSON 6 |
| 3 | STUDENT 2 | LESSON 6 |
| 2 | STUDENT 1 | LESSON 6 |
| 1 | TEACHER | LESSON 6 |
| 0 | COMMON | LESSON 6 |

| Edit Level |
|---|
| none |

TEACHER MAPPING LOGIC
IN STUDENT MODE FOR STUDENT X

| Mapping Table | | |
|---|---|---|
| Level | Layer | Part |
| 2 | STUDENT X | LESSON 6 |
| 1 | TEACHER | LESSON 6 |
| 0 | COMMON | LESSON 6 |

| Edit Level |
|---|
| 2 |

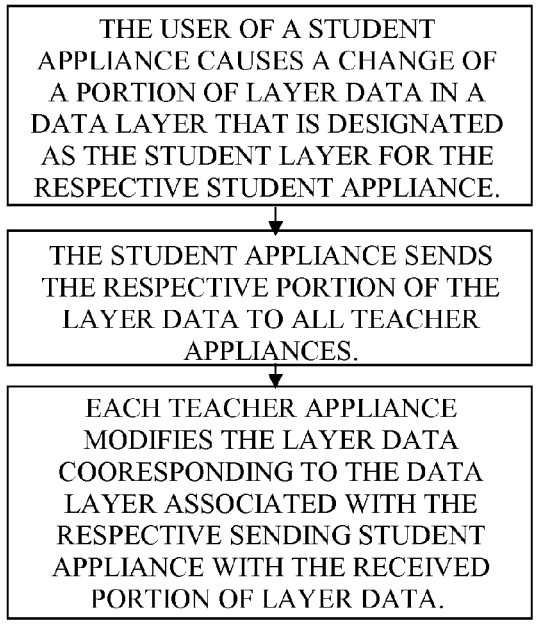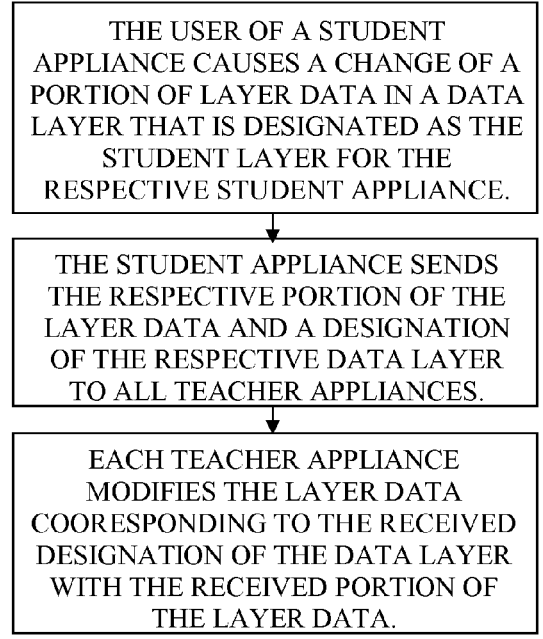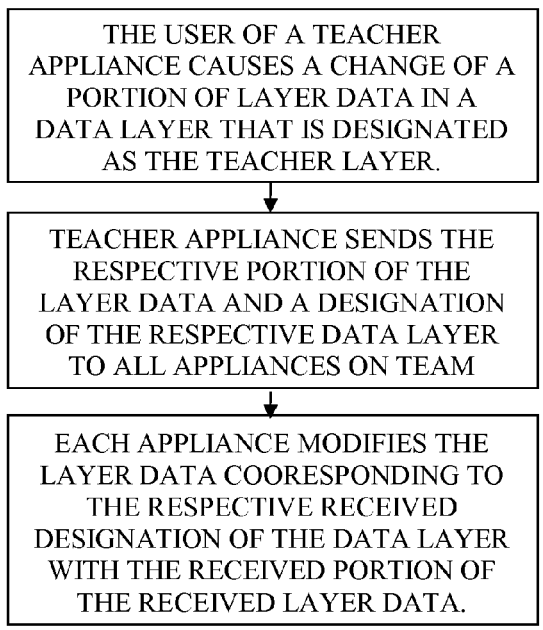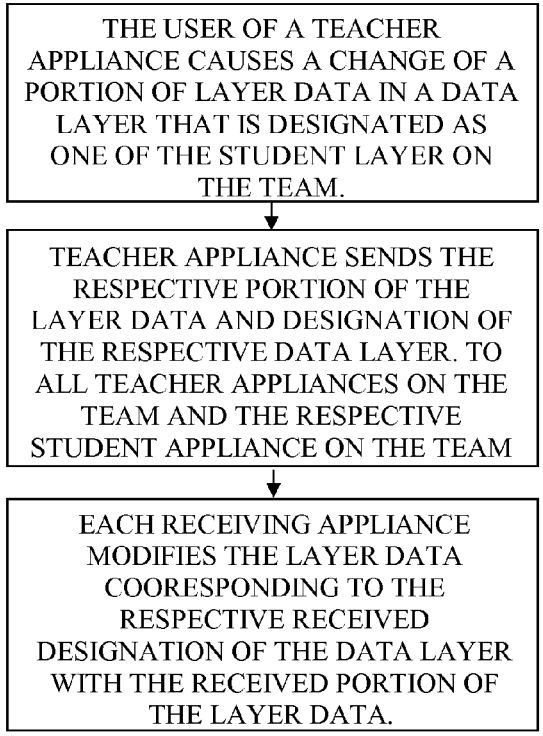

FIG. 37

AD HOC MEMBER 1 MAPPING LOGIC
WITH DISTRIBUTED DATA LAYERS

| Mapping Table | | |
|---|---|---|
| Level | Layer | Part |
| 2 | MEMBER 1 | PAGE 7 |
| 1 | NOTES 1 | PAGE 7 |
| 0 | COMMON | PAGE 7 |

| Edit Level |
|---|
| 2 |

AD HOC MEMBER2 MAPPING LOGIC
WITH DISTRIBUTED DATA LAYERS

| Mapping Table | | |
|---|---|---|
| Level | Layer | Part |
| 2 | MEMBER 2 | PAGE 8 |
| 1 | MEMBER 1 | PAGE 8 |
| 0 | COMMON | PAGE 8 |

| Edit Level |
|---|
| 1 |

AD HOC MEMBER 3 MAPPING LOGIC
WITH DISTRIBUTED DATA LAYERS

| Mapping Table | | |
|---|---|---|
| Level | Layer | Part |
| 1 | MEMBER 1 | PAGE 7 |
| 0 | COMMON | PAGE 7 |

| Edit Level |
|---|
| none |

FIG. 38

THE USER ON THE SENDING
APPLIANCE SELECTS A PORTION OF
LAYER DATA IN A DATA LAYER
(THAT IS MARKED FOR EDIT
OR ANY DATA THAT IS SELECTED)
↓
USER ON THE SENDING APPLIANCE
SELECTS ONE OR A PLURALITY OF
RECEIVING APPLIANCES ON TEAM
↓
SENDING APPLIANCE SENDS THE
RESPECTIVE PORTION OF THE
LAYER DATA TO RECEIVING
APPLIANCES
↓
EACH RECEIVING APPLIANCE
MODIFIES THE LAYER DATA IN THE
DATA LAYER MARKED FOR EDIT
FOR THE RESPECTIVE RECEIVING
APPLIANCE WITH THE RECEIVED
PORTION OF THE LAYER DATA.

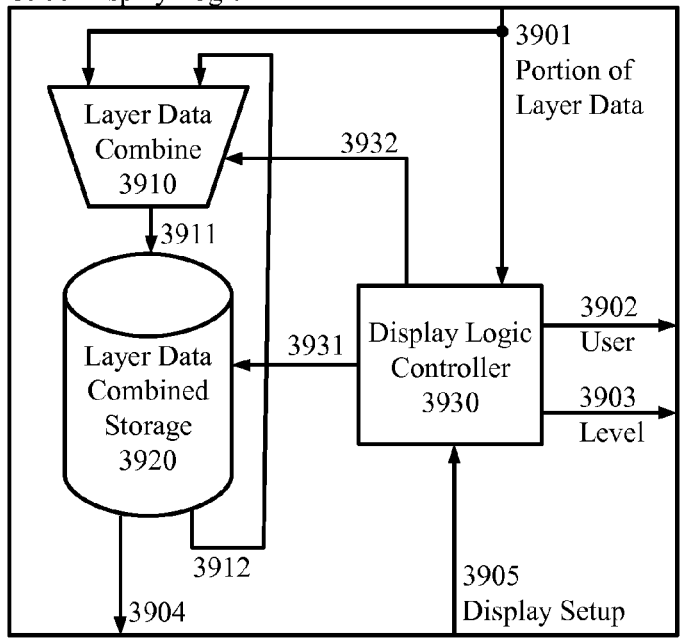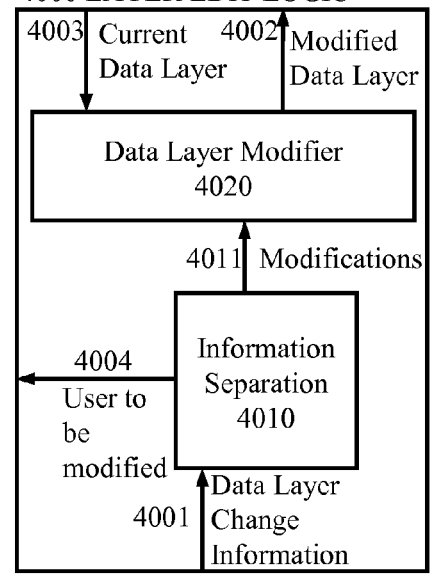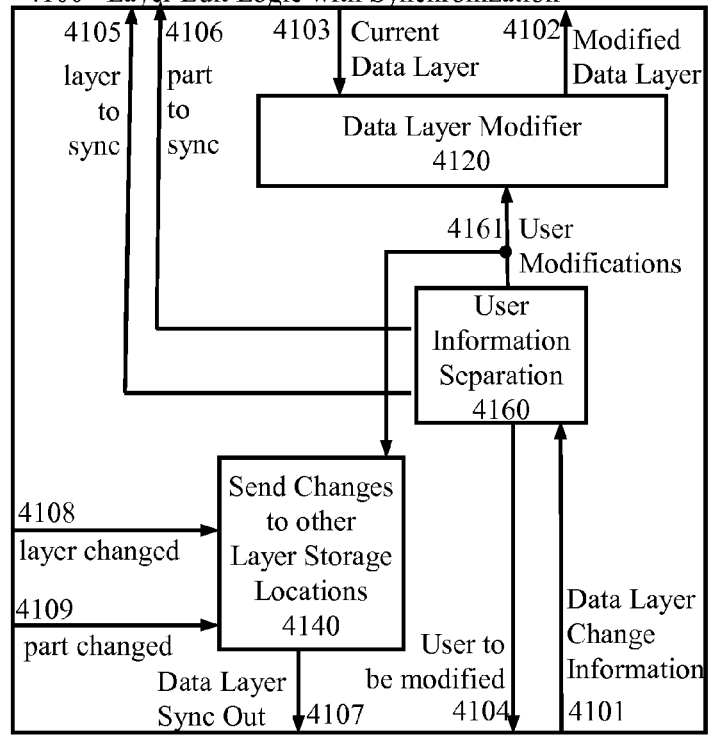

3 items are shown in each list,
each list can contain any number including none (0)

Fig 61

| | |
|---|---|
| 6101 | Chat |
| 6103 | Frankie |
| 6111 | From: John Hey how's it going? |
| 6112 | From: Mary I'm having a bad day. |
| 6113 | From: Jim Check out stock JUNK is going up. |
| 6114 | From: Me Just fine. |
| 6115 | From: Sally Just love your music. |
| 6116 | From: Jane I'm looking forward to next concert |
| 6117 | From: Russ When is the concert? |
| 6118 | From: David Next month at Odium Theater |
| 6119 | From: Jane at 7pm |
| 6120 | From: John Great, dinner with wives tonight? |
| 6121 | From: Fred I'm looking forward to concert too! |
| 6122 | From: Randy Jane want to go with me? |
| 6123 | From: Kim Randy, what can I get a ride? |
| 6124 | From: FrankS Concert will be great, new song |
| 6125 | From: Me Yes how about 8pm at OShay's |
| 6126 | From: Bill Kim, I can pick you up. |
| 6127 | From: Jim Now at 45. |
| 6128 | From: John Need to talk PR at dinner. |

Fig 62

| | |
|---|---|
| 6201 | Chat    Show: John — 6204 |
| 6203 | Frankie |
| 6111 | From: John Hey how's it going? |
| 6114 | From: Me Just fine. |
| 6120 | From: John Great, dinner with wives tonight? |
| 6125 | From: Me Yes how about 8pm at OShay's |
| 6128 | From: John Need to talk PR at dinner. |

Fig 63

Chat — Show: Groupies — 6304
Frankie
From: Mary  I'm having a bad day.
From: Jim  Check out stock JUNK is going up.
From: Sally  Just love your music.
From: Jane  I'm looking forward to next concert
From: Russ  When is the concert?
From:David  Next month at Odium Theater
From: Jane  at 7pm
From: Fred  I'm looking forward to concert too!
From: Randy  Jane want to go with me?
From: Kim  Randy, what can I get a ride?
From: FrankS  Concert will be great, new song
From: Bill  Kim, I can pick you up.
From: Jim  Now at 45.

Chat — Show: My threads — 6404
Frankie
From: John  Hey how's it going?
From: Me  Just fine.
From: John  Great, dinner with wives tonight?
From: Me  Yes how about 8pm at OShay's
From: John  Need to talk PR at dinner.
From: Jane  I'm looking forward to next concert
From: Russ  When is the concert?
From:David  Next month at Odium Theater
From: Jane  at 7pm
From: FrankS  Concert will be great, new song 6401
6403
6111
6114
6120
6125
6128
6116
6117
6118
6119
6124

Fig 65

| | |
|---|---|
| 6501 | Chat |
| 6503 | John |
| 6111 | From: Me Hey how's it going? |
| 6112 | From: Mary I'm having a bad day. |
| 6113 | From: Jim Check out stock JUNK is going up. |
| 6114 | From: Frankie Just fine. |
| 6115 | From: Sally Just love your music. |
| 6116 | From: Jane I'm looking forward to next concert |
| 6117 | From: Russ When is the concert? |
| 6118 | From: David Next month at Odium Theater |
| 6119 | From: Jane at 7pm |
| 6120 | From: Me Great, dinner with wives tonight? |
| 6121 | From: Fred I'm looking forward to concert too! |
| 6122 | From: Randy Jane want to go with me? |
| 6123 | From: Kim Randy, what can I get a ride? |
| 6124 | From: FrankS Concert will be great, new song |
| 6125 | From: Frankie Yes how about 8pm at OShay's |
| 6126 | From: Bill Kim, I can pick you up. |
| 6127 | From: Jim Now at 45. |
| 6128 | From: Me Need to talk PR at dinner. |

Fig 66

| | |
|---|---|
| 6601 | Chat    Show: Frankie 6604 |
| 6603 | John |
| 6111 | From: Me Hey how's it going? |
| 6114 | From: Frankie Just fine. |
| 6120 | From: Me Great, dinner with wives tonight? |
| 6125 | From: Frankie Yes how about 8pm at OShay's |
| 6128 | From: Me Need to talk PR at dinner. |

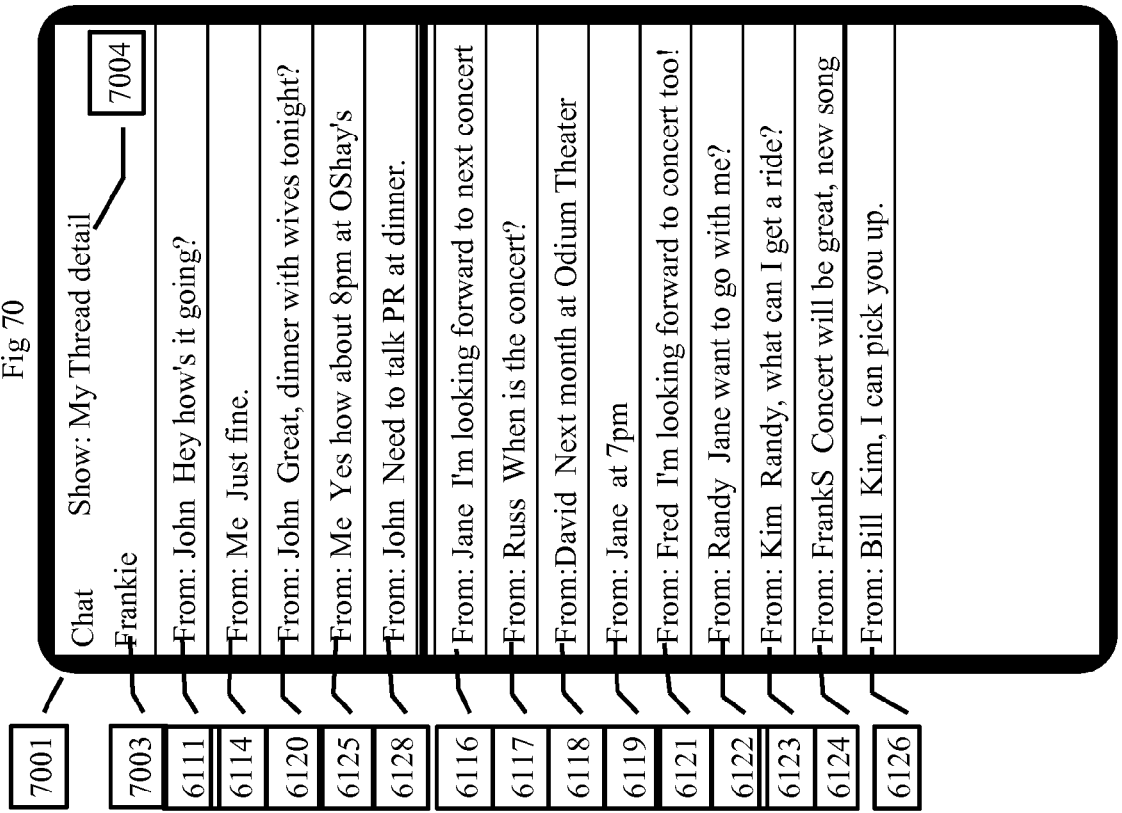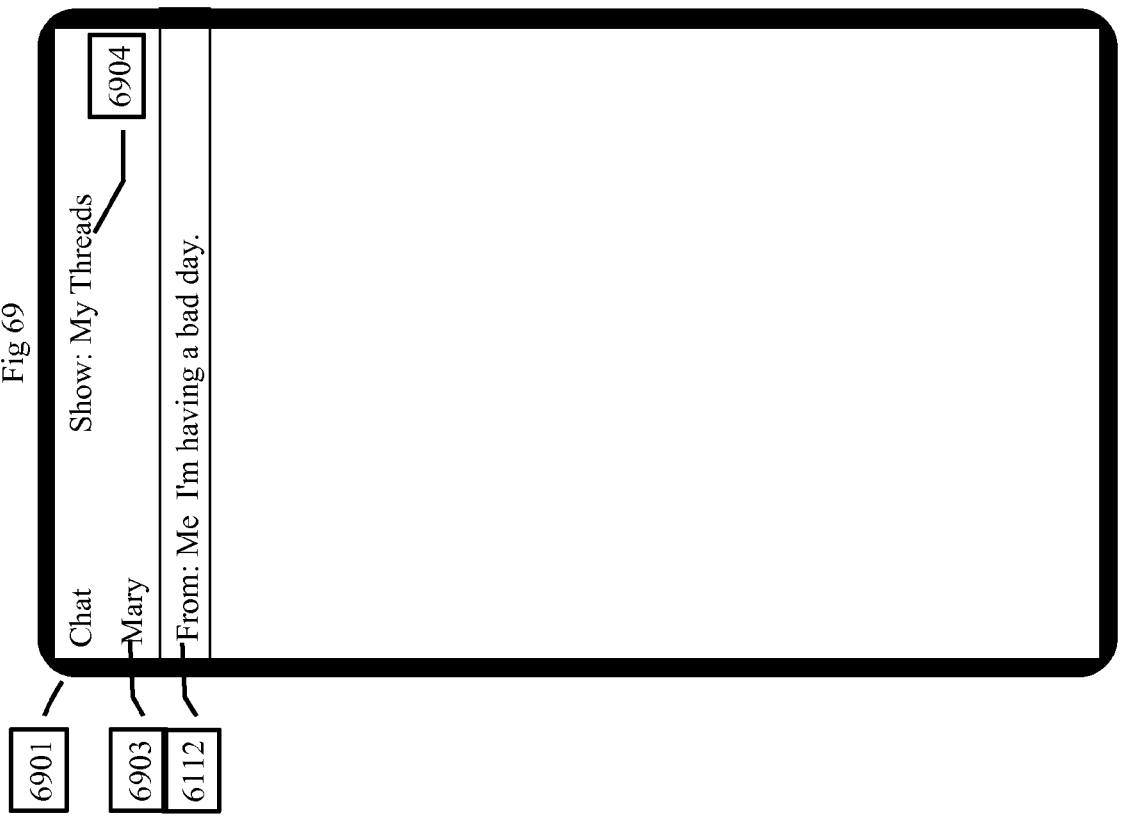

SYSTEMS AND METHODOLOGIES PROVIDING CONTROLLED VOICE AND DATA COMMUNICATION AMONG A PLURALITY OF COMPUTING APPLIANCES ASSOCIATED AS TEAM MEMBERS OF AT LEAST ONE RESPECTIVE TEAM OR OF A PLURALITY OF TEAMS AND SUB-TEAMS WITHIN THE TEAMS

FIELD OF THE INVENTION

The present invention relates generally to the use of computer systems and applications as a tool in working with documents, and more particularly to a family of systems, methods and apparatus for facilitating and managing a complete and thorough manner to concurrently view and collaborate on a document (or documents), and provide navigation, editing of images and providing user interfaces, and providing data storage and management infrastructures and mechanisms, such that the present invention provides for multiple user real-time collaboration, and to apparatus, systems and methods for multiple individual users each separately and concurrently being able to be modifying as a group a core graphical image, and selectively choosing and displaying chosen ones of the users' modifications along with the core graphical image.

BACKGROUND OF THE INVENTION

There are computer programs that permit a single user to type text and/or draw via a computer keyboard and/or mouse or other pointing device. An example is a Word Processor (such as Word by Microsoft Corporation, Redmond, Wash., as well as other programs such as WordPerfect, OpenOffice, etc.).

These Word Processor programs often permit the use of tracking of changes made by a user to a document. Thus, a first version of a base document from a first user can be saved as a new and separate document file (a base version of the base document), which file is then shared with a second user (or multiple other users). Then, that second user creates and saves a new and separate document file (a new second version of the base document), wherein that second user can make edits to the base document with tracking turned on so that it creates that new second version of the base document which is a red-lined markup version of the first version of a base. Then, a next user (such as either the first user or a third user) can receive and open that new and separate document file (the second version of the base document) and that next user creates and saves a new and separate document file (a new third version of the base document), wherein that next user can make edits to the second version of the base document with tracking turned on so that it creates that new third version of the base document which is a red-lined markup version of the second version of a base document. And this process can keep repeating over and over, and so on and so on, creating more and more new and separate document files (a new next version of the base document), wherein the next user makes edits to the previous version of the base document with tracking turned on so that it creates that new next version of the base document which is a red-lined markup version of the previous version of the base document. Then, when desired, at some point in this process, a latest one of the red-lined document versions can be "accepted" and saved as a new and separate document file which is a clean version of that latest red-lined version but with no red-ling showing, only the final result of deletions and additions of the totality of red-lining in the accepted version.

During this process, there are multiple new and separate document files created, one new and separate document file taken for each turn by each user for the set of separate edits made by that user during that turn by that user. And, this process inherently causes delays because there is a need to wait for each turn of a user to be completed before a next user can begin his/her turn of making edits and inputs.

Furthermore, there is also the case where the base version of the base document goes to multiple other users. Then, each one of the multiple other users individually and separately creates his/her own new and separate document file (creating multiple ones of a second version of the base document), wherein each one of the multiple other users makes his/her own set of separate edits to the base version of the base document (making the edits with tracking turned on) so that he/she creates a different one of multiple ones of a second version of the base document, each one of which is a red-lined markup version of the first version of the base document. At that point, there are real problems, because now each and every one of the multiple users needs to look at each different one of multiple ones of a second version of the base document for each of the other ones of the multiple users, while also looking at their own separate one of the second version of the base document, in order to understand the inputs made by each of the multiple users. This is a slow, inefficient and frustrating manner to work. And it leads to a loss of momentum and to confusion. This process is again a step at a time, back and forth, seriatim, and not concurrent.

An alternative to this process with Word Processor and tracking, and sending new and separate document file versions of a base document version back and forth, is to work online as a group with a shared file that keeps being updated with changes as they are occurring, but still occurring with only one user in control (making his/her edits/inputs at a time, in a seriatim usage manner. [An example of such a tool with one user in control at a time, and seriatim use, is "Google-Docs", available at docs.google.com, or at www.google.com, owned by Google, Inc., of Mountain View, Calif.]

Initially, a first version of a base document from a first user is saved as a new and separate document file (a base version of the base document), which file is then centrally stored on a Google computer server, which file is then shared via that server and an Internet coupling with multiple other users). Any one of the other users can select to take control and make an edit to the shared document. As the edit is made, the shared file on the server is updated to create and save a new and separate document file (anew second version of the base document) that contains those edits to the base document. Then, a next user (such as either the first user or a third user) takes control and he/she can edit that shared server document file (the second version of the base document), and when those edits are made, the shared file on the server is again updated to create and save another new and separate document file (a new third version of the base document) that contains those edits to the base document. And this process can keep repeating over and over, and so on and son on, creating more and more new and separate document files (a new next version of the base document).

During this process, there are multiple new and separate document files created and saved and stored on the server, one new and separate document file for each turn taken by each user. And, this process inherently causes delays because there is a need to wait for each turn of a user to be completed before a next user can begin his/her turn of making edits and inputs.

And, it leads to a loss of momentum and to confusion. This process is again a step at a time, back and forth, seriatim, and not concurrent.

There are drawing programs and illustration programs that are single user with a single document on a single computer, which permit multiple layers to be utilized to create an image. However, these are for single user use, and do not work for multiple user collaboration. [An example of such a tool with one user in control at a time, and seriatim use, is "Photoshop", available from Adobe at www.adobe.com (Adobe Systems Incorporated, of San Jose, Calif.] This is a slow, inefficient and frustrating manner to work. This process is again seriatim, and not concurrent.

There are also programs that permit communications via email permitting sending and receiving of communications (text with or without attached files) to be sent back and forth between users. [An example of such a tool with one user in control at a time, and seriatim use, is "Thunderbird", available from www.Mozilla.org.] This is a slow, inefficient and frustrating manner to work. And, it leads to a loss of momentum and to confusion. This process is again a step at a time, back and forth, seriatim, and not concurrent.

There are also programs that permit communications via instant messaging to permit multiple users to text message back and forth. These communicate text messages back and forth, but do not permit collaborative work upon a common base document text or image. This is a slow, inefficient and frustrating manner to work. And, it leads to a loss of momentum and to confusion. This process is again a step at a time, back and forth, seriatim, and not concurrent.

There are also programs that permit conferencing communications via voice (using a microphone and speaker) or via video (using a video or still camera) among multiple users. These permit voice communication or camera-based video communication in a very limited manner, but do not permit concurrent collaborative edits and inputs in real-time to be performed upon a common base document (text or image).

There are also problems that permit communications wherein there is conferencing where one specific user at a time is in control (often referred to as that user having the token), wherein that one specific user can show what is on his/her computer screen to be viewed by other viewing users who can only passively watch based upon that one specific user's display. [An example of such a web-conferencing tool with one user in control at a time, and seriatim use, is "WEBEX" at www.webex.com, owned by Cisco Systems, Inc., of San Jose, Calif.] At some point, that one specific user can decide to give up control, and can decide to select a document file stored on that one specific user's computer, or that one specific user can choose to save a first version of a base document from that one specific user's computer, and that first version of a base document is then shared with one or multiple other users.

Then, the control (the token) is taken over by another user. That other user can then show what is on his/her computer screen to be viewed by other viewing users who can only passively watch based upon that specific another user's display. That display can be something independent of what the first user was showing, or can be a display of the first version of a base document from that one specific user's computer.

At some point, that specific another user can decide to give up control, and can decide to select a document file stored on that specific another user's computer, or that one specific user an choose to save another version of the base document (which is an edited version of the first version of a base document (which is an edited version of the first version of a base document from that one specific user's computer), and that another version of a base document can then be shared with one or multiple other users. And, this process can keep repeating over and over, and so on and so on, creating more and more new and separate document files (a new another version of the base document), wherein a next another user makes edits to the previous version of the base document, so that it creates that new next another version of the base document.

This alternative is a low, inefficient and frustrating manner to work. And, it leads to a loss of momentum and to confusion. This process is again a step at a time, back and forth, seriatim, and not concurrent.

This invention provides for an efficient, real-time document collaboration system that provides an unique ability to separate the input of users and provide customized and dynamic presentations of the document with edits to each user.

SUMMARY OF THE INVENTION

Document collaboration ("DC") is a powerful paradigm. Document collaboration provides a unique vehicle, to concurrently work with others, (1) in simultaneously viewing a same-base document image, (2) any or all users can annotate at the same time, and (3) all users can see the real-time annotations of all other ones of the users that are in a same group. Its embodiment is a powerful tool to its users. It provides a new user interface paradigm—like FaceBook. Document collaboration is an enabling medium upon which can be built a set of usage practices and protocols to allow the medium to be adapted to the operations of a target use.

In accordance with another aspect of the present invention, the concurrent use of document collaboration is used in conjunction with and concurrently with conferencing (such as audio, video, screen sharing, application sharing, etc.).

In accordance with another aspect of the present invention, "document collaboration" is combined in various permutations with the "conferencing solutions" and results in special synergy.

The document collaboration solution works with a wide-range of many different target markets (each which for separate reasons cares about document collaboration features). With document collaboration, users can focus on working directly on the core base document. Each user can write, draw or type text as user annotations that appear in the display presentation that is made viewable to all users in the working group/team.

The legal market is a good fit, because they are not focused on giving of presentations, but rather the focus is on working with documents and tracking of "who said what"

As used herein, the term, "conferencing solutions", refers primarily to a screen sharing and/or and audio/video conferencing tool.

As used herein, the term "screen sharing" refers to the user that is a presenter has a selected window of the screen display image on their computer desktop as displayed on their desktop screen display is communicated to and displayed upon the displays of all other users.

As used herein, an "audio/video tool" provides all equipment and tools for people to be connected to one another ranging from using web-cams and microphones to audio-only phone calls. Just as there can be split-screen video of different users' subsets of annotations, there is a parallel analogy in the audio and audio/video areas (such as using multiple channels (switched/controlled) for multiple chats at once. Audio can be separately sent to other people on the team through the computing system hosting the document collaboration or via a separate phone conference (e.g., POTS (Plain Old Telephone System) or Internet or cable).

As used herein, "document collaboration" permits users (each at a separate computer display) to all commonly view, collaborate upon and work on (discuss and annotate) documents, and manage a library of documents.

All users commonly view the same image display for an underlying document being worked on. As annotations are made by a first user that appear in that first user's display as markings showing atop the image of the underlying document, the annotations can also be seen simultaneously by other users as appearing in each of the other users' displays also aligned for viewing atop the image of the underlying document.

Conferencing solutions are about people interaction and transitory visuals that are momentarily displayed or audio sounds that are momentarily played. Conferencing solutions do not permit management of documents or groups of documents.

With document collaboration, the users are concerned about the development of a document.

With conference solutions, the users' concern is to discuss something (e.g., a subject or document).

The collaboration technology of the present invention maintains information about the development and evolution of the document (layers of annotation data mapped and stored by User Identification and by Annotation Timing).

With the present invention, each user's annotations are logically mapped and correlated to a document. This is one focus of the collaboration. However, another novel perspective is how the annotations are correlated to the document and presented to the users.

Annotations for each of the users are stored and separated into user layers or user Data Layers. In addition to the annotation data stored in the user layers, there is also stored meta-data as to when (date, time) those annotations were made, and by whom. This provides a time line and ownership of annotation data, a related meta-data defining how the documents were created and evolved.

Another novel area is utilizing the perspective and paradigm of working on the viewable image of a document and using "images of annotations" aligned atop the image of the document. The annotation data is thus representative of the display presentation for annotations of a respective user as aligned to and written atop the underlying document.

With user ID and timing information for the annotation data, it makes it easier to be able to reconstruct "who said what when", and to maintain information about the development and evolution of the document.

This information (about the development and evolution of the document) that is maintained can then be utilized for selective viewing of annotations by user or group or subgroup of users, and/or by time of entry or by other criteria.

By contrast, "The conferencing solutions" are one user at a time. All annotations are in the same single layer in a conferencing solution. There are limited tracking of annotations made by members of the conference and if they are available it isn't easy to separate various users from the final result because they do not maintain each user's markings in a separate Data Layer. The conferencing solutions may not even provide a final markup of a document. It does not even provide any concurrent markup of a document.

Conferencing solutions may permit a user who is presenting at the time to markup or annotate his/her screen. Others may be given the opportunity to further markup the document but it doesn't get maintained in the document. The screen that was annotated can be saved outside the document on a "per page" basis. These saved screens with annotations must be manually correlated later by the user who maintains the work product.

Conferencing solutions do allow all annotations to be placed on one layer over an underlying document. Individual annotations can be removed but since all users contribute to the same single layer, the individual contributions by user is lost and the order of the development of the document with annotations is lost.

The collaboration technology of the present invention is a better tool than standard conference tools in those instances where the document itself is the center of attention (that needs to be changed) [rather than the focus being a presentation and personal interaction].

There are other document collaboration tools available other than the collaboration technology of the present invention but many do not provide real-time editing. None allow for multiple Data Layers for separating the user's additions or for creating a new Base Data Layer from previous edits. They provide a single Data Layer for providing the annotations, markings and edits to the existing document.

Also, the collaboration technology of the present invention is a peer-to-peer solution whereas the conference solutions and other document collaboration solutions are a client/server model. (The collaboration technology of the present invention can also be implemented in a client/server model as well.) The collaboration technology of the present invention can operate on a local area network where every appliance can communicate with any of the other appliances. This provides the flexibility to operate, even when Internet access or is not available.

One of the difficulties with a peer-to-peer solution is that communications over the Internet is conducted in a server-to-server or client-to-server manner. Client-to-client communications are generally not possible directly on the Internet for a variety of practical and technical reasons. The collaboration technology of the present invention avoids this by using an Internet server that the peer-to-peer clients connect to. Then the server allows messages from one client to be passed to other clients that are connected to the same server. The peer-to-peer messages are maintained but the client-to-client connection is simulated by the client/server connections. The server does not have significant computational requirements so it can handle more clients. The server is also not storing large amounts of information for all the users. This is maintained on the user's systems. Security issues with centralized storage of information is minimized. Still the redundancy of the data is maintained at each user's local appliance. This allows each user to access the documents, albeit maybe not in direct collaboration with others, any time, anywhere.

Our document collaboration system provides control of the operation in each system with data also flowing between systems. Client/server systems generally require that you be able to access the server to access the documents unless local storage for all documents are provided on the user's appliance. This either makes it impractical to access the documents reduces the benefits of a centralized storage of document information. The server in addition controls most of the aspect of the system. This does allow for better centralized control of the use of the system but it also puts a "middleman" between the user and getting their job done. If control of the users is minimized in a centralized server then the benefits of this control is minimized for a central server and a peer-to-peer solution is more appropriate.

When our systems are used in a local network the bandwidth is not limited by Internet connectivity or server bandwidth, only by the user appliances. On the other hand our system and all peer-to-peer systems have more synchronization issues of data since the data is generally replicated across several systems. If a system is not connected to the team and activities take place, the system must be brought up-to-date to the rest of the team and the team must be brought up-to-date to changes made by the user.

Even where the collaboration technology of the present invention is a better solution for a customer than conferencing above, there are also many situations where some or all of the features in the conferencing (e.g., audio and/or video) solution are beneficially added to the document collaboration. This combines the best of conferencing and document collaboration to allow real-time discussions to occur as the documents are edited. This minimized miss-communication and provides instant feedback.

In its simplest form, the document collaboration is utilizable as a tool used in conjunction with a concurrent use of a telephone or video conference. Alternatively, an online conferencing can be utilized for voice or video.

For instance, Skype is an online audio and/or video conferencing system that provides the typical conference solutions. This could be done in a split screen mode with the document collaboration on one part of the split-screen display and the conferencing being shown in another part of the split-screen display. Furthermore, if desired, the base document being worked on (e.g., a Word document) can be shown in yet another part of the split-screen display.

A starting document provides an underlying canvas referenced and utilized in common by all users for joint collaboration. The starting document can be a Word document file, or Excel file, or image file (e.g., JPEG, PDF) or any computer file. The starting document is converted into an importable format for an equivalent image file for its associated display presentation.

This starting document has a respective associated display presentation, which forms the underling image file utilized as the underlying canvas for the collaborative display of the underlying image of the starting document.

In document drafting, the starting document file format is usually a text or word processing [".doc"—Word] file, such as for the Word text document corresponding to the associated display presentation.

This is the base document which has a corresponding underlying image upon which are overlaid all annotations thereafter drawn, written, typed-in, or otherwise provided, responsive to input by each of multiple users each at a respective one of the plurality of computing systems. This collaboration continues iterating, continuing to generate a respective updated version of a collaborative display output and continuing until the result evolves into a final consensus of what the document should be (as shown in its updated version of a collaborative display output having an associated display presentation wherein, ultimately consensus is reached in the form of a final collaborative display output with associated display presentation).

This results in generating a final agreed-to document [whether it be an agreement, a patent application, a prospectus, litigation papers, one or more drawings, or any multimedia object (audio and/or video-visual)], which also are provided in the generation of the display presentation for final collaborative display output, which comprises as the underlying image the respective associated display presentation for the original starting (base document), upon which is overlaid the respective associated display presentations for each of multiple image layers, each comprised of a semi-transparent overlay image for the video presentation representative of respective annotations for each user as stored in a respective one of the multiple layers which annotations are drawn, written and typed-in by each of the multiple users.

The end result of this joint collaboration with multiple users at multiple respective computing systems is to provide a final result obtained by consensus reached by collaboratively annotating relative to the image of the starting document, and relative to the overlaid annotations of each and all of the multiple users. This final result is provided as a video presentation that is the final collaborative display output representing the END RESULT of multiple users annotating relative to a common display of a current updated version of a collaborative display output progressing to generate the display presentation for the final collaborative display output.

With our technology, all users make modifications individually and in parallel, concurrently, in real-time, that are stored in an associatively mapped data layer in memory as associated with the respective user making the input of annotations. Those modifications may or may not be sent to all users. The modifications may or may not be sent to one or more other users. The annotation data for the modifications (or annotations) are selectively sent to other users based on what the defined Role of each of the other users in the defined Team.

For instance, in an Education Team, the appliances with a defined Role of students only send those modifications (edits) made by the Student appliances to the appliances with a defined role of Teachers. The Student appliances do not send to other Students' appliances in terms of communication).

The third component is that each of those appliances can merge the modifications that they have for display on a local display. An example would be in the education mode, if you are a student role, then your appliance always displays the teacher layers/images and your appliance also always displays your own user layer. Whereas only, if you are a teacher role, the user of the teacher appliance can either select to see only the display of the teacher layer (or layers) or alternatively, the display can be of the image from the teacher layer along with the image from the respective student layer(s) for a Student, or you can see all of the displays present at each of the students' appliances shown in multiple small images plus the display for the teacher layer selectively merged with the core/base document along with each individual students' appliances shown in small picture images. The teacher can select from three different views (+/- views as design choice), or the teacher's appliance can display the choice of the user of the teacher appliance for each of those views, whenever you are in one of those views, that also determines what modifications you can make to the displayed document from that view. In the first example, where you are looking at teacher-only display, you are able to modify the teacher layer. If you are viewing a display for a particular student, then you as the teacher are able to do editing or modifying of that respective student's layer. If you are viewing a display on the teacher's appliance of all the students, then you cannot make any modifications to any of them from the teacher's appliance in this mode.

With a Team, there are three things: we have a team made up of multiple members or users (at least two), each user at a respective appliance. Each member has a role in the team, and has capabilities that are permitted based on the role of the team. Examples of these capabilities include: 1) what modifications a user can make based on their specific role; and 2) what sort of data level mergers are going to be made in providing a display; and 3) who (to which other members/users) do they communicate their modifications to, and 4) in what specific data layers are their modifications stored and what data is stored in which data layers. It is not just about managing which appliances to send the modifications to, but it is what layers to send the modifications to be stored in the receiving appliance, and which data layer the respective data is to be stored in on the receiving appliance.

Consider an example of an education team with teacher and student roles. There are multiple views where the view that is taken as a subset determines other feature sets. For example, the teacher can write and display but the feature set that the teacher activates is dependent on the mode or the view that the teacher puts their appliance into. So if the teacher goes into a teacher mode, then the teacher is going to view a display presentation using only the teacher layer but the modifications the teacher makes will be sent to all students' appliances to be stored in a teacher data layer therein and to be provided as a part of a display presentation thereto. In fact, all other appliances of all students and all teachers will store and display the modifications. Whereas, checkerboard multiple student and teacher mode, then the display presentation shown to each teacher will see a checkerboard layout of screen displays for all students and teachers, each screen display shown in a thumbnail or filmstrip-type display, but only the teacher sill be able to select one of the checkerboard images to bring to full screen and switch to a one-on-one interactive mode. In the multiple screen view mode, there is selection of a screen and/or viewing mode, but there are no modifications or changes or layers that are communications. The teacher can simply move to another view with the exception that any modifications that are happening in real time on a screen being viewed will be shown on the checkerboard. So the teacher can see the other modifications happening in real time, but in multiple screen view-mode, the teacher cannot make any modifications in her role.

A third role for the teacher is a private communications where the teacher touches the screen for one of the students' thumbnails (instead of the teachers). By touching a specific student's thumbnail, the teacher selects a one-on-one mode, where the teacher's modifications appear on that student's screen for viewing by the student in real time, even if the student is also concurrently writing. The student can erase what the teacher has written when in the one-on-one mode, but not what the teacher has written during when the teacher was in the teacher layer mode. The role of teacher and the mode of operation not only affects what the teacher as the appliance in that view can do, but it also affects the rights and privileges of what the receiving appliance can do with the modifications it receives. So if the teacher sent the modification in the teacher mode with the teacher layer only, and with the changes made, then the student, when they receive it, cannot erase or change that modification. But, if the teacher is in a one-on-one private network and makes a change, the student can erase that change.

On the student appliance, the user can always modify the students' layer and can communicate the student layer changes/modifications to all the teachers. So, the student's role does not change, and its user always can selectively see displayed the changes of the student layer. However, teacher changes can select different modes of which data layer the teacher's appliance it is modifying from the teacher layer in teacher mode to a particular student's layer in the one-on-one mode.

On a one-on-one network, the teacher is modifying the student's layer and therefore, the student has access to un-modify it. This determines which layers are being modified. More specific language or restrictive language to the claim to have specific limitations on what layers are modified, what modifications to which layers are sent to other appliances, and what other appliances display from the merger of which layers and the document.

When an ad-hoc meeting is conducted for collaborative work, each appliance has one user layer file. The user of any appliance can select a portion of said user layer file that is the user layer file for that respective appliance or stored locally at that respective appliance or stored as the user layer file for that respective appliance but stored in one or more of any of the plurality of the appliances. Each appliance has its own respective associated user layer file for storing data for that user/appliance. Each appliance has a respective one user data layer file (out of a plurality of data layers stored in a layer storage memory) associated with that respective appliance. In user edit mode, the respective appliance can make modifications to its own one respective user data layer.

A communicating user of an appliance can select one of the other appliances, and they can select a portion of their own data layer to communicate to one of the other appliances and then the communication select portion is stored. In the one mode, the selected user data layer file for storage of data layers at each appliance as it receives data. Thus, the received data is stored in the respective one user data layer file as associated by the receiving appliance. So it is receiving appliance that stores received edit data for each respective user in respective user data layers. So in laymen's terms, we have a bunch of stands there.

Everyone has their own user selected. They draw a lasso around some annotations that they have made on their display and select them. That is the selected portion. Then, they click on "send" and they can send the selected portion to one or all of the appliances that are in networked communications. The receiving appliance takes those annotations and puts those annotations in the same data layer that the other appliances are currently using for storage of similarly originated edits, for that said user. So the user can thereafter delete them or edit them from there.

User 1 is using an appliance (appliance 1). Appliance 1 has an associated storage user data layer (named "D"). User 2 is using Appliance 2. Appliance 2 has its own associated user layer, a user layer name "R". The two appliances communicate. Appliance 2 makes edits to Page 4 of his music. Appliance 2's user layer R (associated with Page 4) is selected and that portion is sent to Appliance 1. That portion is written into Appliance 1's user layer D (associated with Page 4). Appliance 1 does not write user data layer R on to Appliance 1, and then do a merge of data layer R (for Page 4) and data layer D (for Page 4). This could however also be done, in order to gain the ability to keep the edits sent to you separate from the edits that you were making [In the music mode, we do that. Essentially that. For the feature set of being able to distinguish edits shared in the document in real time, then wouldn't you want to be able to do what I said, which is to associate the changes you made to a portion of modifications you made for selected portion of your user layer that is associated with a respective selected portion of a common underlying document and your user layer would be communicated and stored as a separate user layer, the R layer for example.] So, Appliance 1, when connected to Appliance 2, would add an R layer and to Appliance 1 and would add a D layer to Appliance 2. So all the appliances would contain data layers for all networked appliances in collaboration so that users could do and undo the edits as they needed to.

Let us suppose a person, user A made changes to a number of particular pages, and has sent the annotation data for the modifications for a first page to another person (user B). User A also sends the annotation data for modification to page two to user C. User A also sends annotation data for modifications to the third page of modifications. User A asks all three of those people, users B, C and D, to modify the pages. Users B, C and D have also have been making some changes, independently, on their own. With the present invention, all that individual input collaboratively can be integrated and work together to result in a complete record of the activity. Each user's annotations are stored in an associatively mapped one data layer. All input of annotations (edits) by a user persists in the storage of the respective annotation data in the respective one data layer. The result of the combining the layers is the completed all-in-one document. Each user sends back to the other users, the annotation data as stored in that user's respective said data layers. By creating user data layers on each appliance, each appliance has a mirror of the content in the set of data layers in local memory of all the other appliances and the users can track changes by user and by time back and forward.

Thus, in the example of document sharing by users where after multiple users entries, a user is unable to allow you to individually take and remove certain edits made by one user or another, such as because the shared document just keeps adding all users changes in time to a single common layer. By contrast, in accordance with one aspect of the present invention, the documents' modifications are separated and stored and organized by user data layer. Prior art document sharing creates a layer for all users' environment. Whereas in accordance with this aspect of the present invention, in an ad-hoc mode, every user that logs on has their own user layer that they are editing. They may also get some edits form some other people and some not. An, everybody actually has a chance to have their set of edits on that document. With prior art document sharing a letter with some blanks left in it, is a common base document that everyone sees and everyone makes their own independent (concurrent) edits to that document. Let us suppose that everyone is customizing the document for a letter which will be going out to a companies a, b, and c. Each user has a, b, and c companies that they are sending it out to. They are making their own custom edits to change that. There is no set of associative data layer storage to individually store annotations. Rather one data layer overwrites all users annotations to a common element atop one another. If user A selects a word "Red", and user B changes it to "Blue", and user C changes it to "Brown" and user D changes it to "Green", then user A sees only "Green" and none of the other comments from other users Wheres with the present invention and associatively mapped data layer storage, each user's edits are viewable and can be turned "on" or "off" selectively. You can make changes and send that change to everybody or just certain people in certain groups and change that clause in there and everybody gets it.

For example, for a particular company, somebody else might want to go and override and change it back because of some contractual relationship or something. That is a peer-to-peer communication implemented by each user having a layer and communicating.

Data layer storage can be centralized or distributed with each local appliance having a layer locally stored. Each appliance could have an associated one of the data layers that is for storing that user's annotation and then centrally stored (in a set of data layers).

In an appliance mode embodiment, each local appliance has computing power and stores the database in the set of data layers (locally storing the multiple data layers in that database).

In a centrally stored embodiment, it would require that the central database be maintained so that the contained layers (or sets of layers) are stored for every user and a merged output is provided to each user comprised of the global or common layer, plus either the individual layer for just that user or the individual layers for all users or a subset of users. This would require that the system differentiate based on who/which user appliance is communicating and if displayed through a browser as to what it would provide an output part of the merged database is to be locally stored for display.

The advantage of a central server is that it always has all the storage for all the appliances available to it. IT could actually potentially do a few more things. It also has not synchronization issues, since with a central server, all storage is all in one place, or a few places, with fewer synchronization issues. There is also fewer synchronization issues because the data layers are all stored in a central place. The disadvantage is that the system always has to be connected to that central server in order to do anything. Users cannot work independently at all. There are also some potential speed issues because you have to connect and go over a communication line to the central server.

In a preferred embodiment, there is also provided for at least two of the users' voice communications provided concurrently with the collaboration via annotations. This is a further parallel of a same-place/same-time work environment.

A voice communication happening at the same time as the document collaboration provides for discussing the collaboration and the suggested changes while they are being made by the user viewing the computer display presentation.

In one embodiment, a PDF file of the printout of the final collaborative display output represents the END RESULT of using the collaboration system in collaborative sessions by multiple users concurrently viewing and annotating relative to a same video display presentation to create a then version of final collaborative display presentation output.

In a preferred embodiment, the collaboration system continuously updates from its initial (or then current) starting document to utilize a new next starting document image that is to be utilized as an underlying display presentation from which to create a next final collaborative display presentation output representative of the next current base underlying image.

In one embodiment, an administrative user who is typing revisions to the starting document file, (e.g., in Word format), can utilize a split-screen display presentation, displaying the final collaborative output display on one part of a large LCD screen in a split screen mode and on the other part of the large screen (in the LCD split screen mode of the display apparatus) there is displayed the display presentation for the in-process starting document file [e.g., such as an open Word document running in Word as the starting document].

Using one part of the display presentation screen for the Word document, then the other part of the display presentation screen is used to see the results of the collaboration and what the substance of the annotations are in the final collaborative display presentation output. The administrative user can utilize that information to decide what changes are needed to be made to the starting document and then to actually make those changes to the starting document itself (e.g., the Word document) so that it corresponds to the final collaborative display presentation output.

Where annotations made by a user during collaboration are input by typing of text, then that text is stored in the collaborative document file format as a portion thereof that is usable in text format (e.g., to copy/paste between documents). The collaborative system permits the administrative user who is revising the starting document to copy and paste to or from any text that was typed by any of the multiple users into the collaborative file and to permit that user to take the copied text and to move it from within the file format of the collaboration technology of the present invention, and thereafter pasting the copied text into a Word (or other) document as text in the proper respective location in the starting document relative to the same corresponding location in the final collaborative display presentation output [since that "output" represents the image of the display presentation of the respective starting document]. Alternatively, or additionally, text can be copied from an external document (e.g., Word, Excel, text, or other document, or an Internet web-page), and pasted into a document in the collaboration technology of the present invention.

This saves a lot of time (especially for longer phrases) both in eliminating the retyping the text, and in eliminating having to re-proof the re-typed text in the Word document.

Consider the case where a Word file corresponds to an original base or starting document, from which an initial version of a collaborative display presentation output was obtained as the underlying image.

Starting from this initial version of a collaborative display presentation output (having a corresponding respective data file format structure and logic), and after many hours of multiple users annotating and creating an updated multilayer file version having a continuously updated collaborative display presentation output, continuing to be updated, until a final consensus is reached having a corresponding respective final collaborative display presentation output.

In one embodiment, there are multiple users who are respective primary deal workers and one or more administrative support workers. The primary deal workers are the ones that concurrently use the collaborative document system to create the final collaborative display presentation output.

A server or server-less networking system can be used.

The collaboration technology of the present invention bridges the "physical presence gap" that makes it hard to work with same documents with multiple users in different locations as compared to working with those documents in the same way as if the multiple users were all in a single room in the same location working on the same physical document(s).

The collaboration technology of the present invention utilize the starting document to provide an underlying canvas upon which the multiple users can reference to individually or concurrently work upon to annotate an overlaid image layer that is visually aligned relative to the respective associated display presentation for the starting document. The corresponding display presentation output is created by layers of overlaid user annotations relative to the underlying image. The final collaborative display presentation output is created utilizing the underlying canvas representative of, and overlays representative of, a final collaborative mutual consensus and agreement, which is represented by the display presentation of the final collaborative display output.

The collaboration technology of the present invention enables users at remote locations ("remote users") to concurrently work together on a common document as though the remote users were physically in the same location working on the same physical document. And, beyond just working on a static common underlying document, there is additionally provided a sense of images of an evolving (with users' annotations overlaid upon the common document).

In accordance with another aspect of the collaboration technology, users in a same physical location ("local user") are able to precisely, visually communicate with annotations overlaid atop a specific visually seen location in a selected document. This is a new level that does not even exist without the collaboration technology of the present invention.

The collaboration technology of the present invention provides a user the ability to precisely communicate exactly specific thoughts as a visual overlay of that user's input of annotations appearing at the user's selected specific location/position within (aligned atop the display presentation of) a document being worked on collaboratively by a plurality of users as a group (or team, or additionally, members of a group within groups-sub-groups; and members of teams within teams-sub-teams). A user can instantly highlight for all to see, and let other users know specific selected location (words that bother me in a sentence that has been written). A user can look at an image such as a CAT-Scan, and the user can circle or highlight to effectively point all other users to focus on a specific selected region of the CAT-Scan image and this enables each user to immediately mark-up and communicate to other users looking at that same common core image document (in this example, the CAT-Scan image). This would also be highly beneficial to a remote user(s) linked to other users and/or databases (resident local), and/or remote databases that can be accessed. For example, an emergency worker could get access to each work with a schematic of wiring of a phone closet, or of the water piping or ventilation in a public building, etc. This provides an ability to collaborate in an emergency situation occurs such as between firemen and crew, through working and discussing with someone how to fix a problem.

The collaboration technology of the present invention can also be used in business to communicate among remotely located individuals [such as for use in a shareholders' meeting, such as to communicate with the officers of the company, by a plurality of users in (each) participating via a computer display subsystem to collaborate at a conference, providing a way for the attendees to communicate with the presenters, and vice-versa.]

It can also be used for purposes, such as meetings (or conference calls/collaboration sessions) for document preparation, use in lawsuits and discovery (where there are thousands of pages of documents and the collaboration technology of the present invention provides the ability to precisely pinpoint exactly from which discovery step, or which word, or which part of what drawing, or what part of an agreement).

In each of these cases, there is a common core document where the document can be an agreement (or proposal, or legal brief, or prospectus, or marketing plan, etc.), where there is specific language that is not acceptable, the collaboration technology of the present invention allows each and all of multiple users to show other multiple users precisely the location (circle or highlights, etc.) what is not acceptable, and to also precisely correct it (e.g., insert typed or written annotations with arrow pointing to location point for insertion of the annotations), and let all users see instantly what correction is being suggested (and, precisely showing the other users (in their display presentations) what the suggested correction looks like and where it is to appear within the document).

In a preferred embodiment, each user is provided with (voice or video with voice conferencing) concurrently with being provided a related collaborative document display presentation. Multiple people/users can all concurrently type or hand-write via stylus or otherwise annotate, or provide markings of their own ideas, atop the display presentation of the core document. This allows each and all of them to instantly share their ideas with other users. This also provides a display presentation wherein some or all users (on the team) can instantly see all the other users' ideas and specific suggestions.

The collaboration technology of the present invention creates a new environment, a new paradigm that did not previously exist. It creates the ability to collaborate, enhanced in ways that enables concurrently markings of each and all the users, and provides a display of the markings that concurrently appear within the display presentation provided to all the users. The display presentation is shared for viewing by a selected one, some or all users (in real-time, preferably).

In a preferred embodiment, the collaboration technology of the present invention provides for concurrent entry by each user of that users' annotations for a plurality of the users, and provides a concurrent updated display presentation comprised of a base core document image and an image of the users' annotations (appearing aligned atop the core document image within the display presentation (of a combined image display presentation)).

In a preferred embodiment, each user's markings are uniquely identifiable (e.g., by an assigned respective color to identify the respective users' markings) within a combined display presentation provided to all the users within the group/team. The ideas of the users are concurrently expressed, displayed (in a way that identifies them with the user), and shared (ideally in real-time), wherein the annotations as integrated into an updated combined display provided to multiple selected users for all to see concurrently with the ongoing voice and/or video-conference discussion in the shared document (image).

Thus, each user is provided with precision of communication at levels of clarity and achievement that were not really attainable heretofore.

Best of all, the collaboration technology of the present invention provides a key team tool to allow opposing teams of people (users) to actually resolve all issues to closure for a shared document, such as representative of text, graphic, image, multi-media, etc.).

The collaboration technology of the present invention provides a way to synchronize and track user markings/edits, in a time-stamped tracking mode, and can maintain a continuous history of at least to all one user's activity in the collaboration technology of the present invention.

All the people working together on documents (and also concurrently talking either in person in a same room, or remotely talking via phone or video conference) can collaborate in real-time via hand-written annotations, typed edits, inserted images and/or talking [while each and all are viewing (concurrently) the same physical documents display images]. People can collaborate together whether within a same room with all local users, or remotely linked to collaboratively couple users at multiple different locations to collaborate together (with one or more at each sites (e.g., local, or remote relative to each other user. This can be used within a company or law firm, or any group or organization. This can also be used between different groups or organizations. Teams can be formed to communicate within the team with one another. Sut-teams with members from within the team can be formed, to communicate among members of the sub-team, independently of other communications between the team's members. And, there can be multiple sub-teams within a team.

Another use of this technology is to facilitate group collaboration, annotation and use of large amounts of documents. Any user in the group can use bookmarks to locate (mark a location for later reference) things for later discussion (label/name them for use in a table of bookmarks). Thereafter, all the users benefit from this locating and labeling as bookmarks, which simplifies document review so that any user can use only the labeled (e.g. 50) bookmarks to find things instantly and benefit from that organization. Thus, only the relevant 50 bookmarks are needed and used, instead of having to physically go through 10,000 or 100,000 pages. This has valuable beneficial uses in law, research of any kind, engineering, marketing, sales, medicine, music, etc. Plus, it allows any one user of the group to be a leader of the group and to control which page is to be displayed at one, or all, of the users' displays, such as controlling a jump to page X for everyone to be at the same place in the same document (e.g., Go To Bookmark, or Go To Page #).

With the collaboration technology of the present invention, any user can quickly (nearly instantly) find and share with other users on the same team. They can share everything they want. In a preferred embodiment, each user is collaboratively linked together. The users can be in the same room, and/or users can be at remote locations. In a preferred embodiment, each user is also coupled for communicating (e.g., voice, video with the users in the group). For example, each user can be coupled on to a conference call (e.g., video or voice only) with other users on the same team (or on the same sub-team within a team). Alternatively, if all users are local, they can sit in a room together and talk and concurrently provide annotation input via a respective user input responsive to each single user's control. Each user has their own said respective computing appliance (e.g., laptop PC, tablet PC, desktop PC, tough-screen PC systems, etc.) Each user can create and use bookmarks by marking a location in the present display presentation (or use section marks or page jumps) to instantly jump to any place within a library of stored documents, providing for a local display presentation to that user (or to all users including that user). Then, any user can mark annotations via their user input and using their local touchscreen display relative to a base display image. A user can start with a highlighter transparency setting and select as the pen type=marker, and mark up what it is wanted by the presenter to be seen by others in a group of users (e.g., while drawing a circle, saying, "see this area here" (within the commonly displayed image of a specific page of a specific document). Prior solutions required saying "third line on the page, the 12th sentence". However, now with the collaboration technology of the present invention, a user can simply mark its location (such as circle it) (and everyone instantly sees the marking) and say "see this", and everybody is in the same place. When one user on a team marks the display presentation (e.g., highlights it), everyone on the same team get highlights on all users' display presentation screens.

Alternatively or additionally, each user can have one or multiple separate open display presentation windows, with one or more application software display presentation windows using the collaboration technology of the present invention, and with one or more other application software display presentation windows, (such as running a Word processor (e.g., Word, NotePad, TextEdit, Quark Express), image processor (e.g., Adobe PhotoShop, PreView, Adobe Acrobat, Adobe Illustrator, Corel Draw, PowerPoint, and image viewer (e.g., PreView, Acrobat, QuickTime, etc.).

A user can also select an area to copy from a document in one window (either) and paste it into another document within another window, such as pasting it into a collaborative work in the window that is being worked on.

A user can also cite to the bookmarks within the collaborative document (or otherwise) or to a page number associated with the bookmark.

In accordance with one embodiment, any one (to all) of the users can operate with multiple windows open on that user's computer display, comprised of a display presentation in one window using the collaboration technology of the present invention, and a document, or graphic, or image (e.g., Word, PhotoShop, etc.) display presentation in another window.

The system described is composed of plurality of appliances on a network forming a team that is working together on a common project. Users collaborate with the team by interacting with Layer Data which is stored in Data Layers that are shared with other team members. Each user accesses a display of information that can be composed of image, video, text, audio and other forms that the appliance can provide and the user view. Each user views a customized display of the information based on selectively accessing the Data Layers. These Data Layers are combined responsive to the Layer Data. The display is thus customized for each user based on the ordering of the Data Layer and the selection of Data Layers. The storage of Layer Data in Data Layers and their selective combination based on the user provides for a flexible and powerful mechanism to facilitate collaboration in the team and meet the changing requirements for each user's need to view different Layer Data and the collaboration occurs.

The Layer Data in the Data Layers is composed of Layer Data Elements which include two items: context and content information. The latter, is the content that is displayed for the user. The content information can be in the form of vector line drawings, graphics, images, tables of data, text, audio, video, gaming data, and other data. The context information is used to provide the display logic the information to properly display the content. Context information provides context parameters for the display of content information in either relative or absolute terms to other Layer Data Elements, in the same or another Data Layer, or to an entire Data Layer. The context parameters can be spatial locations or references to other Layer Data Elements that imply ordering of Data Layer elements. For instance, several Data Layers containing text, e.g., "This i", "s a te", "st.", could be referenced in a particular order using context information. The display would then display them to the user as "This is a test". Also, a Data Layer element could contain an X,Y coordinate that refers to a location on the screen of the display or it could refer to an offset from another Layer Data Element. The context information could also contain other information such as a name which could be used by the display generation to include or eliminate Layer Data Elements based on the context information. If context parameters provide invalid information, such as an X,Y coordinate that would be off screen or a reference to another Data Layer element that is not visible or no longer existing then the display generation can choose to include the said Data Layer element with default information or not include it in the display.

The embodiment of Data Layer structure is illustrated in FIG. 71. This can be implemented using tools in several ways. A relational database can be used. Relational databases can be accessed in various ways but a common method is using Structured Query Language, SQL, statements (http://www.itl.nist.gov/div897/ctg/dm/sgl_info.html). The Layer Data can be stored in a Layer Data Table wherein each row is a Layer Data Element. A number of columns in the table make up the context information and other columns provide the content information. Alternatively, a Context Elements Table could contain columns for only the context information and an index column. Each row of said table would represent a Context Element. A Content Elements Table could contain columns for only the content information and an index column. Each row of said table would represent a Content Element. The relational join operation could dynamically create a table containing both context and content information. A SQL SELECT statement with a WHERE clause can be used to implement the Layer Data Element Selection function. The WHERE clause would be formed from the Part specification and context columns. For example, "WHERE ContextPage=5". ContextPage is a column in the Data Layer table. The Page indicates that "page 5" should be retrieved from the Layer Data. The content information can be stored in the relational database as a column as a binary large object, BLOB (see SQL specifications for a BLOB), either in the Data Layer Table directly or in a separate table. The content information can also be stored as a link, or filename, to the content in one of the columns of the Data Layer Table. Those skill in the art of relational databases have many options for the specific structure of the tables that are used for the optimization of performance and the type of content information. This embodiment is preferred if a relational database is available and the system is fast enough to use it.

An alternate embodiment would implement as illustrated in FIGS. 45 and 56. This embodiment uses a hybrid structure for the Data Layers. The Base Data Layer is stored in a database illustrated in FIG. 45 which could be a relational or similar table based database. The Image Table, 4560, contains the content information as a filename (imgname) to the content information as an image in the File System, 4540. The context information is stored in the Doc Table, 4510, DocPage Table, 4520, Value Table, 4530, and Image Table, 4560. The PageImage Table, 4550, is used as part of the linkage of all of these tables to provide the Data Layers. The other Data Layers are pointed to by doodle_file in the Value Table, 4530. The doodle_file is illustrated in FIG. 56. Some of the context information is obtained from the database tables Doc Table, 4510, DocPage Table, 4520, Value Table, 4530. The remaining context information is stored in the doodle_file. The Wrapper Group, 5610, provides the pointers to the Data Layers available. The Layer Groups, 5630, 5631, 5632 provide for the individual Layer Data storage locations. The Layer Groups also contain context information for the Layer Data. The Layer Data storage illustrated in FIG. 56 is optimized for speed while the Base Data Layer image is optimized for storage of large images. This embodiment shows multiple tools implementing the Layer Storage and Data Layers. A system does not have to implement the Layer Storage identically for all Data Layers and can optimization the Data Layer for the system requirements and type of Layer Data. This is a preferred embodiment that illustrates flexibility in the design and optimization of speed when needed.

The context information can include the time that a document was created, the time that a n annotation was created, modified or accessed, the visibility of an annotation, the size of an annotation, image properties, user name, page number, section, chapter, bookmark, Layer Data Element that it is linked to (may be in another data layer), company name, physical location of appliance, location relative to another Layer Data Element, color, font, font size, font style, line width, . . .

An appliance may be associated with more than one Data Layer. This allows many possibilities for the operation of a team. A team could be composed of multiple subteams. Each subteam would have members to that team. Each team would only view the Data Layers used by their subteam and a few other Data Layers used to collaborate between teams. A coordinator appliance would control those Data Layers. This would allow several teams to operate independently but can publish their results on Data Layers that are visible to other teams. This provides both security and minimizes distractions as multiple teams as subteams work together as one large team. Teams can include more subteams as needed and can be included in larger teams with changing their structure.

Each appliance is assigned a "Role" that it performs in the team and each team is defined by its "Team Type", e.g., how the team should function together. The Team Type and Role provide the rules for the appliance to manage the appliance's use Data Layers and the rules for combining the Data Layers for the display. This includes managing which Data Layer a user can edit and modify, which Data Layers an appliance combines for the display, options for the Data Layer combination, what part of the Data Layer the appliance uses for the display.

Lawyers routinely work with documents that shared with others and many times need to discuss and modify the document before an agreement can be concluded. Many times everyone is not physically available in the same location. They are also not necessarily available at the same time. The use of the collaboration technology of the present invention allows both of these restraints to be eliminated while allowing simultaneous collaboration regardless of location and time. The modifications to the document would have the opportunity to record a time line of what modifications were made by whom and when. This time line could also be erased when the parties make an agreement and this time line is no longer necessary.

Contracts, litigation and licensing have at least two parties, typically composed of lawyers, plaintiff, defendants and clients. Each party needs its own subgroup to discuss, modify and propose changes to the contract, suit or patent. The proposed changes by a party is then communicated to the other parties in the contract in their own private discussions. The lawyer tends to be the person that proposes the changes to the other subgroups and communicates the reasons and significance to the clients in their subgroup. Therefore the lawyer will input data in two layers, one private layer for communicating with the others in their subgroup, and a second subgroup layer for communicating with the other subgroups. Everyone would be able to view the subgroup layer of all subgroups. Everyone would be able to view the private layer for their own subgroup only.

Patents require the development of documents that require the input of the patent attorney and the inventors. Notes by the inventor and review of the patents with the patent attorney can be conducted in real time, despite location differences.

Litigation also provides a unique opportunity for providing a real-time discussion of court documents in a trial. The judge would have access to all layers which provide input from all the lawyers in the courtroom. Each lawyer and the judge would have their own layer that they could provide input. The layers that the jury could see is controlled by the judge so that only the appropriate layers for the jury are shown to them after approved by the judge for their viewing.

Discovery using the collaboration technology of the present invention would allow all parties to review documents, mark their objections and have them reviewed by the judge. This would not require that all the parties be physically in the same room so it can speed up the preparation for trial.

Doctors are increasingly dealing with documents in their practice. These documents are shared between physicians, specialists, pharmacies, insurance representatives, billing departments and of course the patient. Documents include medical records, bills, insurance forms, admitting forms, medical releases, prescriptions and medical results. Many times the people are in very different locations. A collaboration technology of the present invention medical system could ease the time required to collaborate on these documents. Also data rights management can be applied to documents so only those authorized to view a document are allowed to view it or modify it. Patients, nurses, administrators, insurance agents and doctors can fill in forms with all the information about who provided what input at what time. Physicians can collaborate in real time on x-rays, cat-scans and other medical tests.

Engineers and architects create many documents that need to be reviewed by their clients, project managers, manufacturing, construction, procurement and each other. A collaboration technology of the present invention provides that ability to have each person, regardless of location, provide real-time input, review, analysis and reference to the latest documents. In addition, each change is recorded so each party's input can be compared, reviewed and approved.

Shareholder meetings, churches, synagogues and public meetings are real-time events where there can be user interaction with the audience. Questions are routinely ask and documents are routinely shared with the audience. Both can be communicated via an appliance which has large screen or a projector that is viewable by the audience.

Live production requires a team that is in close coordination. As the saying goes, "The show must go on", which is the result of something not going according to the rehearsed plan. The ability of a collaboration technology of the present invention to rapidly communicate the issue and then rapidly communicate the changes provides all the production team to continue while maintaining the best performance.

Other examples of the Team Type are "Music", "Education", "Meeting", "Ad Hoc" and "Social". Teams will be prefixed by their Team Type later in this description such as "Music Team", "Education Team", "Meeting Team", "Ad Hoc Team" and "Social Team".

A Music Team can have the Roles of "Leader", "Member" and "Listener". An Ad Hoc Team uses the same Roles as the Music Team: "Leader", "Member" and "Listener". The Member and Listener Roles are identical in operation when operating within a Music Team. The Leader and Member Roles are identical in operation when operating within an Ad Hoc Team. Otherwise the Roles differ in operation in an Ad Hoc Team or Music Team. The Education Team can have the Roles of "Teacher" and "Student". The Meeting Team can have the Roles of "Presenter", "Facilitator" and "Participant".

The number of Roles for a Team Type is not limited and may be one, two or more. Later in this document we will refer to an appliance by its Role, e.g., Leader Appliance, Member Appliance, Listener Appliance, Teacher Appliance, Student Appliance, Presenter Appliance, Facilitator Appliance or Attendee Appliance.

The appliances working on a team must be operating in a role that is included in a Team Type and may include a "Coordinator Appliance". A Coordinator Appliance is an appliance operating in a Role with "Coordinator" functionality that allows it to define such things as which appliances are included in the team, their Roles and access rights. A "Non-Coordinator Appliance" is simply an appliance that is not a Coordinator Appliance. The Leader Appliances, Teacher Appliances and Facilitator Appliances are examples of Coordinator Appliances for their respective Team Types. There can be many appliances operating on the network so some Team Types require that at least one appliance on the team be a Coordinator Appliance.

Each Teacher Appliance defines which Student and Teacher Appliances are on their Education Team, thereby creating various "Classrooms" of Education Teams. Student Appliances only communicate with the Teacher Appliances in their Classroom by sending their annotations in the particular student's drawing layer. Teacher Appliances communicate with all the appliances in the Classroom or a particular Student Appliance. The Teacher Appliance either sends annotations in the student's drawing layer to a particular Student Appliance and any other Teacher Appliances in the Classroom or a common teacher layer annotation to all the Student Appliances and any other Teacher Appliances in the Classroom.

Likewise, Leader Appliances define the Leader Appliances, Member Appliances and Listener Appliances on their Music Teams. The Leader sends their annotations to all the other appliances in the team in their own layer. This layer is only modifiable by the that particular Leader Appliance. The Leader Appliances can also send other messages such as page turns to the Music Team. The Member Appliances and Listener Appliances on the display the all the Leader Appliance drawing layers in their team. Member Appliances and Listener Appliances operate the same on a Music Team, their operation differs on the Ad Hoc Team described later.

Facilitator Appliances define the Presenter Appliances, Facilitator Appliances and ttendee Appliances on the Meeting Teams. The Presenter appliance has control of the other appliances in terms of what page they are viewing. The Facilitator Appliance controls which appliance is the Presenter Appliances and Attendee Appliances, what data layers are viewed by each appliance and which data layers are editable by each appliance. The Attendee Appliances may be able to turn pages on their own determined by the Facilitator Appliance. The Attendee Appliances will be controlled as to what layers they can view and edit based on control from the Presenter and Facilitator Appliances. The Ad Hoc Team has no Coordinator Appliances and is composed of Leader Appliances, Member Appliances and Listener Appliances. The Ad Hoc Team uses all the appliances available on the network of these Roles. Leader Appliances and Member Appliances can send annotations to an other appliance in the Ad Hoc Team, but the Listener Appliances only receive annotations.

By utilizing the teachings of the present invention, a method is provided for displaying collaborative work as input by a plurality of users.

In a first embodiment, the method is comprised of providing annotation data for each of the plurality of users which is representative of the respective annotations by the respective user; storing the annotation data for each respective said user in a memory as associated with said each respective said user; enabling at least one user of the plurality of users to select which of the annotations are selected annotations that are used in generating the display presentation; and providing a combined display presentation to at least one user, the combined display presentation comprised of the selected annotations combined with a base core image.

The annotation data can be provided by any of multiple means, such as via a user input apparatus such as a keyboard, mouse, touchscreen input, stylus and digitizer input, voice recognition, camera recognition, import of images, scans, vector drawings, 2D and 3D models, audio, video or text data. This is discussed in further detail with relation to FIGS. 26, 27, 28, 42 and 43 herein.

The association of each user with his/her respective annotation data is provided by mapping logic whose configuration is responsive to the mapping control that is responsive to one or more control processors. The mapping logic is discussed in further detail with relation to FIGS. 11, 12, 13, 14, 29, 32 and 37 herein. The mapping control is discussed in further detail with relation to FIGS. 15, 18, 22, 24, 27 and 28 herein. The memory is structured to support this association by layer storage. This is discussed in further detail with relation to FIGS. 16, 17, 19 and 20 herein. The memory can be centralized or distributed as discussed in further detail with relation to FIGS. 1, 2, 3, 4, 5, 6, 7, 8, 9 and 10. The enabling of selection by at least one user of the plurality of users to select which of the annotations are selected annotations that are used in generating the display presentation is provided by one or more control processors to which the aforementioned mapping control is responsive. Coordinator control logic is a control processor that is responsible for coordinating all the user displays. The Non-coordinator control logic is responsive to the coordinator control logic. This is discussed in further detail with relation to FIGS. 8, 9, 10, 24, 25, 26, 27, 28, 42 and 43 herein.

The generation of the display presentation is provided by the user display which is responsive to the display logic. The display logic is responsive to the aforementioned layer storage and mapping logic. The display logic is discussed in further detail with relation to FIGS. 24, 27, 28, and 39 herein. The user display is discussed in further detail with relation to FIGS. 24, 25, 26, 27, 28, 42 and 43 herein.

In a further embodiment to the one embodiment, the method is further comprised of enabling at least one user of the plurality of users to select which of the plurality of users is enabled to input the respective annotations therefor.

The global control processor obtains input from the at least one user of the plurality of users and communicates with the all the mapping controls to control mapping logic and display logic for selecting the annotation that is the destination for user input from the respective input device. This is discussed in further detail with relation to FIGS. 8, 9 and 10 herein. There may be a plurality of control processors which obtain input from each respective user. At least one control processor of the plurality of control processors and communicates with the all the control processors in the system to coordinate the selection of which of the plurality of users is enabled to input the respective annotations. The control processors control mapping logic and display logic for the display of annotations for all user displays and the annotation that is the destination for user input from the respective input device. This is discussed in further detail with relation to FIGS. 26, 27, 28, 42 and 43 herein.

In a further embodiment to the one embodiment, the method is further comprised of enabling at least one user of the plurality of users to select which of the users are selected to have their respective annotations selected for use in generating the display presentation.

The global control processor obtains input from the at least one user of the plurality of users and communicates with the all the mapping controls to control mapping logic and display logic for selecting which of the users are selected to have their respective annotations selected for use in generating the display presentation. This is discussed in further detail with relation to FIGS. 8, 9 and 10 herein. There may be a plurality of control processors which obtain input from at least one user of the plurality of users. The plurality of control processors receiving input from said at least one user communicates with the all the control processors in the system to coordinate the selection of the users that are selected to have their respective annotations selected for use in generating the display presentation. The control processors control mapping logic and display logic for the display of annotations for all user displays and the annotation that is the destination for user input from the respective input device. This is discussed in further detail with relation to FIGS. 26, 27, 28, 42 and 43 herein.

In a further embodiment to the one embodiment, the method is further comprised of enabling at least one user, of the plurality of users, to do one of selectively enable and selectively disable utilizing of selected ones of the plurality of users said respective annotations in generating the display presentation provided for viewing to at least one of the plurality of users.

The global control processor obtains input from the at least one user of the plurality of users and communicates with the all the mapping controls to control mapping logic and display logic to selectively enable and selectively disable utilizing of selected ones of the plurality of users said respective annotations. This is discussed in further detail with relation to FIGS. 8, 9 and 10 herein. There may be a plurality of control processors which obtain input from at least one user of the plurality of users. The plurality of control processors receiving input from said at least one user communicates with the all the control processors in the system to coordinate selectively enabling and selectively disabling to utilize of selected ones of the plurality of users said respective annotations. The control processors control mapping logic and display logic for the display of annotations for all user displays and the annotation that is the destination for user input from the respective input device. This is discussed in further detail with relation to FIGS. 24, 25, 26, 27, 28, 42 and 43 herein.

In a further embodiment to the one embodiment, the method is further comprised of enabling at least one user, of the plurality of users, to do one of selectively enable and selectively disable utilizing of selected ones of the plurality of users said respective annotations in generating the display presentation provided for viewing by another said user that is not the at least one user.

The global control processor obtains input from the at least one user of the plurality of users and communicates with the all the mapping controls to control mapping logic and display logic to selectively enable and selectively disable utilizing of selected ones of the plurality of users said respective annotations in generating the display presentation provided for viewing by another said user that is not the at least one user. This is discussed in further detail with relation to FIGS. 8, 9 and 10 herein. There may be a plurality of control processors which obtain input from at least one user of the plurality of users. The plurality of control processors receiving input from said at least one user communicates with the all the control processors in the system to coordinate selectively enabling and selectively disabling to utilize of selected ones of the plurality of users said respective annotations in generating the display presentation provided for viewing by another said user that is not the at least one user. The control processors control mapping logic and display logic for the display of annotations for all user displays and the annotation that is the destination for user input from the respective input device. This is discussed in further detail with relation to FIGS. 24, 25, 26, 27, 28, 42 and 43 herein.

In a further embodiment to the one embodiment, the method is further comprised of displaying the user annotations for each respective said user within the combined display presentation as separately identifiable with the respective user as shown in the combined display presentation.

The control processors communicate setup information to the display logic that configures the display logic to add separately identifiable information for each respective user. The separately identifiable information can be in the form of a different color, a visual label added, a mouse over popup visual label, blinking visual effects, a different text font or character effect, modifying the location of the annotation on the display, 3D layer visualizations and other forms. This is discussed in further detail with relation to FIGS. 39, 42 and 43 herein.

In a further embodiment to the one embodiment, the method is further comprised of generating a separate and independent version of the combined display presentation for each of at least two of the plurality of users. Each said independent version of the combined display presentation is comprised of the respective said annotations of respective selected ones of the plurality of users as combined with the base core image.

The layer storage contains the base core image that is associated with all users. The mapping logic is configured to include the base core image or common data layer and data layers for annotations of respective selected ones of the plurality of users. This is discussed in further detail with relation to FIGS. 29, 32 and 37 herein.

In a further embodiment to the one embodiment, the method is further comprised of associating each respective said subgroup with at least two respective ones of the plurality of individual data layers which are associated with said respective subgroup. Each respective user of the plurality of users is associated with a respective said individual data layer. The method further enables each said respective user to selectively create associated respective said annotations. And the method stores the respective said annotation data for the respective said annotations in the respective said individual data layer associated with the respective user.

The control processors contain the information associating each user with a subgroup. A data layer is associated with each user. The edit level for each respective mapping logic user is setup to point to the respective data layer for each user. This is discussed in further detail with relation to FIGS. 8, 9, 10, 26, 27, 28, 42 and 43 herein.

In a further embodiment to the one embodiment, the method is further comprised of associating each respective said subgroup with at least two respective said individual data layers associated with the respective said subgroup; and associating with an editable layer with each of the respective said subgroups, selectively enabling each respective said editable layer for each of said respective said subgroups, to permit at least one user of the respective plurality of users, within the respective subgroup, to create the annotations provided for display to the users of the respective subgroup.

The control processors contain the information associating a subgroup edit data layer with a subgroup. The edit level for at least one user in the respective mapping logic is setup to point to a subgroup edit data layer. Said at least one user can provide change information to the respective subgroup edit data layer. All users associated with the said subgroup include the subgroup edit data layer in the mapping table for display of the subgroup edit data layer and other data layers as needed. This is discussed in further detail with relation to FIG. 32 herein.

In a preferred embodiment, at least one user selects a plurality of the annotations for a respective plurality of users, for use in generating the combined display presentation.

At least one of the control processors is responsive to said at least one user and communicates the selection of a plurality of the annotations for a respective plurality of users. Said at least one of the control processors communicates the selection to all other control processors. The control processors setup the mapping control for the respective users for use in generating the combined display presentation. This is discussed in further detail with relation to FIGS. 24, 25, 26, 27, 28, 42 and 43 herein.

In the preferred embodiment, each one of the respective plurality of users is separately identifiable in the combined display presentation.

The control processors communicate setup information to the display logic that configures the display logic to add separately identifiable information for each respective user. This is discussed in further detail with relation to FIGS. 39, 42 and 43 herein.

In an alternate embodiment, the method is further comprised of identifying at least one sub-grouping comprised of at least two of the respective plurality of users which form members of a respective separate subgroup of users; selecting the respective annotation data for the respective separate subgroup of users for the at least one said sub-grouping of the plurality of users, to be utilized in generating a first combined display presentation presented for viewing to only those said users in the subgroup of users; generating the first combined display presentation comprising the annotations of all the members of the respective separate subgroup provided for viewing by at least one of the respective plurality of users in the respective separate subgroup; generating a second combined display presentation for viewing by at least one other one of the plurality of users that are not members of the respective separate in the subgroup, wherein the second combined display presentation is comprised of the annotations of only one of the members of said respective separate subgroup and excludes the annotations of all the members except the only one member.

Thus, there can be subgroups of users that interact within themselves independently of the larger group of multiple ones of the subgroups. Within each subgroup, the users/members can see the annotations of some or all of the other members of the subgroup. However, only the designated one (or more if so designated) can see the annotations of the other subgroups, and the other subgroups can only see the annotations of the designated one (or more if so designated) user/member of a respective subgroup. This can be done for one subgroup with multiple members, and the rest of the plurality of users are not in subgroups, or there can be multiple subgroups, each as described above, or there can be multiple subgroups, each as described above plus the rest of the plurality of users are not in subgroups. The present invention works equally well in each of these scenarios as above. This aspect of the invention is discussed in further detail with relation to FIGS. 32, 33, 34, 35 and 36 herein.

With this embodiment of subgroups, the method is further comprised of generating the first combined display presentation comprising the annotations of all the members of the respective separate subgroup provided for viewing by all of the respective plurality of users in the respective separate subgroup.

The control processors contain the information associating each user with a subgroup. A data layer is associated with each user. The mapping table for each respective mapping logic user is setup to point to the respective data layers for respective plurality of users having the same subgroup as the said user. This is discussed in further detail with relation to FIGS. 11, 12, 13 and 14.

In one embodiment, there are at least two separate subgroups of users comprised of at least two said sub-groupings, each said respective separate subgroup comprised of members comprising at least two of the plurality of users, and the method is further comprised of linking one said member of a first one of the at least two subgroups to a different one said member of a second one of the at least two subgroups; providing communication between the one said member and the different one said member, of the annotations of the different one said member and the one said member, respectively; generating a first linked and combined display presentation comprising the annotations of a plurality of the members of the first one of the at least two subgroups combined with the annotations of the different one member; and, displaying the combined display presentation responsive to the generating.

The control processors contain the information associating a subgroup edit data layer with a subgroup. The edit level for first said member of a first one of the at least two subgroups in the respective mapping logic is setup to point to a the first subgroup edit data layer. First said member of a first one of the at least two subgroups can provide change information to the first subgroup edit data layer. The edit level for second said member of a second one of the at least two subgroups in the respective mapping logic is setup to point to a the second subgroup edit data layer. Second said member of a second one of the at least two subgroups can provide change information to the second subgroup edit data layer. The first said member of a first one of the at least two subgroups and the second said member of a second one of the at least two subgroups include in the mapping table for display of the first subgroup edit data layer, second subgroup edit data layer and the respective data layers for respective plurality of users having the same subgroup as the said user. This is discussed in further detail with relation to FIG. 32 herein.

In a further embodiment to the one embodiment, the method is further comprised of generating a second linked and combined display presentation comprising the annotations of a plurality of the members of the second one of the at least two subgroups combined with the annotations of the one member; and displaying to the different one said member the second linked and combined display presentation, responsive to the generating. The education team has two groups, a teacher group and student group. The teacher can display the annotations of all the students, together with the teacher annotations on the teacher display simultaneously. This is discussed in further detail with relation to FIG. 60 herein.

In an addition to the first embodiment, the method is further comprised of organizing the memory as a plurality of mapped data layers; associating each individual data layer of the plurality of mapped data layers with at least one respective one of the plurality of users; storing the annotation data for each respective said user in a respective said individual data layer that is associated with the respective said user; enabling at least one user of the plurality of users to select which of the individual data layers are chosen as selected data layers that are used in generating the display presentation; and providing the combined display presentation comprised of the respective annotations for the respective said users associated with the respective selected data layers, annotations combined with the base core image, responsive to the selected data layers. The users of appliances in a social team can change settings on the appliance to hide one or all of the team member layers. This is discussed in further detail with relation to FIGS. 61 through 70 herein.

In the one embodiment, the method is further comprised of generating a same combined display presentation for viewing by at least two users of the plurality of users for the respective subgroup. The education team has two groups, a teacher group and student group. The teacher can display the annotations of a single the student, together with the teacher annotations on the teacher display. These are the same annotations shown on the said student so each view exactly the same display. This is discussed in further detail with relation to FIG. 59 herein.

In the one embodiment, the method is further comprised of generating a different separate respective combined display presentation for respective viewing by at least two respective users of the plurality of users for the respective subgroup. The teacher can display the annotations of a just the teacher on the teacher display. The students display the annotations of the teacher and the student's own annotation. Every appliance has a different display. This is discussed in further detail with relation to FIG. 58 herein.

In a further embodiment to the one embodiment, the method is further comprised of associating each said individual user with a respective computing appliance; providing the input of the respective annotations for the respective individual user responsive to each respective said individual user; and providing the respective combined display presentation to the respective individual user associated therewith on a respective display apparatus at each respective one of the plurality of computing appliances. The teacher can display the annotations of a just the teacher on the teacher display. The students display the annotations of the teacher and the student's own annotation. Every appliance has a different display. The input device for each appliance is responsive to the respective annotation data layer that is being displayed, e.g., the teacher modifies the teacher layer and every student modifies their own layer. This is discussed in further detail with relation to FIG. 58 herein.

Multiple alternative systems are illustrated and described herein for implementing the one embodiment (as well as other embodiments), utilizing a plurality of computing appliances each with a display apparatus for displaying collaborative work comprised of a display presentation to at least one user of a base core image in combination with selected annotations as input by a plurality of users. One such system for the one embodiment is comprised of input apparatus providing annotation data for each of the plurality of users which is representative of the respective annotations by the respective user responsive to user input at said respective input apparatus; memory storing the annotation data for each respective said user in an area of the memory as associated with said each respective said user; logic enabling at least one user of the plurality of users to select which of the annotations for which of the plurality of users are selected annotations, that are used in generating the display presentation; and the display apparatus providing a combined display presentation comprised of the selected annotations combined with the base core image. The overall system is described in FIGS. 5, 6, 7, 8, 9, 10. The input apparatus and annotation data is described in greater detail in FIGS. 26, 27 and 28. The memory stores are described in greater detail in FIGS. 45, 53, 54, 55, 56 and 71.

The annotation/user selection logic enables at least one user of the plurality of users to select which of the annotations for which of the plurality of users are selected annotations, that are used in generating the display presentation. The annotation/user selection logic can be comprised of pointer lists, database tables, tables, vector lists, and is described in greater detail in relation to FIGS. 11, 12, 13, 14, 29 and 60 herein.

The display apparatus provides a combined display presentation comprised of the selected annotations combined with the base core image. The display apparatus can be comprised of graphic adapters, software code for creating the combined image, specialized graphic processors, and is described in greater detail in relation to FIG. 39 herein. The combined display presentation and its structure can be comprised of an image, display languages such as Postscript, PCL, SVG, and others, is described in greater detail in relation to FIG. 39 herein.

In this system, at least one user selects a plurality of data layers for at least two users of the plurality of users, for use in generating the combined display presentation.

In a preferred embodiment of this system, each of the respective plurality of users is separately identifiable in the combined display presentation.

The preferred embodiment of this system is further comprised of logic for identifying a plurality of sub-groupings of the respective plurality of users as respective separate sub-groups of users; memory storing data for each one of the plurality of users in a respective one of a plurality of data layers for at least one said subgroup of users, for use in generating a first combined display presentation, for viewing by only those said users in the subgroup of users; display logic generating the first display presentation comprising the annotations of all the members of the subgroup for viewing by at least one (or some or all) of the respective said users in the subgroup; and wherein the display logic generates a second combined display presentation for viewing by other users who are not in the subgroup that utilizes the annotations of only one said user of the plurality of users in the subgroup.

In an alternate embodiment of the one embodiment, there is one said separate subgroup; wherein each member of that one said separate subgroup is linked to see all members annotations from other members of that one said separate subgroup, and wherein one member of that one said separate subgroup is also linked to all at least one, to all, of the other users who are not members of that one said separate subgroup.

In another embodiment, there are at least two separate subgroups, wherein within each of the at least two separate subgroups each member of that said separate subgroup is linked to see all members annotations from other members of that said separate subgroup, and wherein one member of each of the two said separate subgroup is also linked to show its annotations from that one user/member for viewing to all at least one, to all, of the other users who are not members of that one said separate subgroup.

In yet another embodiment, there are the at least two separate subgroups, wherein within each of the at least two separate subgroups each member of that said separate subgroup is linked to see all members annotations from other members of that said separate subgroup, and wherein one member of each of the two said separate subgroup is also linked to show its annotations from that one user/member for viewing to a respective said one member of the other one of the at least two separate subgroups. Optionally, each of the one member of each of the two said separate subgroup is also linked to show its annotations from that one user/member for viewing by at least one (to all) of the other users who are not members of either one of the two said separate subgroup.

Thus, there can be multiple separate subgroups of users, wherein each of the members of each such separate subgroup interact within themselves independently of the larger group of multiple ones of the subgroups. Within each subgroup, the users/members can see the annotations of some or all of the other members of the subgroup. However, only the designated one (or more if so designated) can see the annotations of the other subgroups, and the other subgroups can only see the annotations of the designated one (or more if so designated) user/member of a respective subgroup. This can be done for one subgroup with multiple members, and the rest of the plurality of users are not in subgroups, or there can be multiple subgroups, each as described above, or there can be multiple subgroups, each as described above plus the rest of the plurality of users are not in subgroups. The present invention works equally well in each of these scenarios as above. This aspect of the invention is discussed in further detail with relation to FIGS. 58, 59 and 60 herein.

In yet another embodiment, the another member of the other one (the second of the at least two subgroups) of the at least two subgroups has a display presentation generated of a second linked and combined display presentation comprising the annotations of a plurality of the members of one to all of the other one(s) of the at least two subgroups, combined with a display of the annotations of the one member of the first of the at least two subgroups. This aspect of the invention is discussed in further detail with relation to FIG. 60 herein. herein.

In a further extension of the system in the one embodiment, the memory is comprised of a plurality of mapped data layers. Each of plurality of mapped data layers is associated with at least one respective one of the plurality of users. The storage provides storing of the annotation data for each respective said user in a respective mapped data layer associated with the respective said user. In this further extension, the system further comprises control logic enabling at least one user of the plurality of users to select which of the mapped data layers are selected data layers that are used in generating the display presentation. The display apparatus provides a combined display presentation comprised of the selected users' annotations combined with the base core image, responsive to the selected data layers. This aspect of the invention is discussed in further detail with relation to FIGS. 15, 18, 22 and 24 herein.

In a preferred embodiment of the systems illustrating the embodiments of the present inventions, there is provided the ability for a user (or more than one user) to select which user or users are permitted to make annotations. This embodiment provides input logic enabling at least one user to select which of plurality of users is enabled to input the annotations for use in generating the display presentation. This aspect of the invention is discussed in further detail with relation to FIGS. 26, 27 and 28 herein.

In an alternate embodiment or additional aspect of this preferred embodiment, there is provided the ability for a user (or more than one user) to select which user or users annotations (for which of the users) is to be utilized in the generation of the display presentation, either for that one user, or for one or more other users. This embodiment provides input logic enabling at least one user to select which of the users are selected to have their respective annotations selected for use in generating the display presentation. This aspect of the invention is discussed in further detail with relation to FIGS. 11, 12, 13, 14, 29 and 60 herein.

In accordance with one aspect of this preferred embodiment, the system is further comprised of control logic enabling at least one user to selectively enable and disable selected ones of the plurality of users to have their respective annotations selected for use in generating the display presentation viewed by at least one of the plurality of users.

Thus, at least one of the users (or more) can select to turn on and off, at will, to select which of the users annotations will be utilized in generating of the display presentation for that one user or for other one or ones of the users. This aspect of the invention is discussed in further detail with relation to FIGS. 29 herein.

In another alternate embodiment of this preferred embodiment, the user annotations for each respective said user is provided within the combined display presentation as separately identifiable with the respective user as shown in the combined display presentation. Thus, for example one user can be red, another user blue, etc. Or, users who are members of a first subgroup can have a first set of colors (either different families of colors, or different hues within a same color) and each other subgroup has its own unique and identifiable set of colors. Thus, when viewing the display presentation, it is readily and easily identifiable as to which user of which subgroup made which annotations in the combined display presentation. This aspect of the invention is discussed in further detail previously herein in regard to context information.

In one alternate embodiment, a separate and independent version of the combined display presentation is provide to at least two of the plurality of users within the respective subgroup; and each said independent version of the combined display presentation is comprised of the respective said annotations of selected ones of the plurality of users as combined with a base core image. Thus, one user can see one subset of users annotations as overlaid atop of and aligned to the base core image in a first independent version of a combined display presentation, while another user user can see yet another subset of (the same or overlapping or completely different ones of) users annotations as overlaid atop of and aligned to the base core image in in a second independent version of a combined display presentation combined display presentation. And this can be done without limitations. It can be done for users within a same subgroup, or for users within different subgroups, or for independent users not within any subgroups at all. The users of appliances in a social team can change settings on the appliance to hide one or all of the team member layers. This is discussed in further detail with relation to FIGS. 61 through 70 herein.

In an alternate embodiment of the subgrouping aspect of the present inventions, each of the subgroups is comprised of at least two plurality of mapped data layers associated with said subgroup; and each user is associated with at least one of the mapped data layers that is an editable data layer that can be selectively enabled (or disabled) to permit (or not allow) the respective user to create the annotations for the respective user. The education team has two groups, a teacher group and student group. The teacher can display the annotations of just the teacher annotations on the teacher display or choose to display the teacher annotation a particular student data layers. The teacher's input changes from the teacher layer to the said student data layer in the latter display. This is discussed in further detail with relation to FIGS. 58 and 59 herein.

In the alternate embodiment of the subgrouping aspect of the present inventions, the system can additionally be implemented such that each of the subgroups is associated with at least two plurality of mapped data layers associated with said subgroup; and such that each of the subgroups is associated with an editable layer that is selectively enabled to permit at least one of the respective plurality of users to create the annotations for the respective subgroup. This aspect of the invention is discussed in further detail with relation to FIGS. 61, 62, 63, 64, 65, 66 and 67 herein.

In an option to the alternate embodiment of the subgrouping aspect of the present inventions, a same combined display presentation is generated at, at least two of the plurality of users for the respective subgroup. Thus, those at least two of the plurality of users for the respective subgroup view the combined display presentation of selected annotations and the base core image concurrently while they work in real time together on editing/annotating relative to the same base core image, provide for a collaborative work result. This aspect of the invention is discussed in further detail with relation to FIG. 59 herein.

In an alternate option to the alternate embodiment of the subgrouping aspect of the present inventions, a different separate combined display presentation is generated at, at least two of the plurality of users for the respective subgroup. Thus, each of those at least two of the plurality of users for the respective subgroup view a different combined display presentation of different ones of selected annotations for respective users, combined with the display of the base core image, concurrently while they work in real time on editing/annotating relative to the same base core image, provide for a collaborative work result. Thus, each of the subgroups can view selected members/users of their respective group independently of the other subgroups' users, or different users (whether or not within a same subgroup, can view selected users annotations independently of what another user is viewing of a separate set of selected users (some the same, or all different). This aspect of the invention is discussed in further detail with relation to FIGS. 61, 62, 63, 64, 65, 66 and 67 herein.

BRIEF DESCRIPTION OF THE DRAWINGS

The present invention may be better understood by reference to the following drawings along with the detailed description of the following drawings.

FIG. 1 illustrates a system with Global Layer Storage with Mapping Logic.

FIG. 11 illustrates an embodiment showing the mapping storage logic with edit logic and layer partitioning for global mapping.

FIG. 12 illustrates an embodiment showing Mapping Logic with layer partitioning for global mapping, alternative to and similar to FIG. 11 with the exception that it does not include the edit logic as shown in FIG. 11.

FIG. 13 shows system embodiment with a Mapping Logic for distributed mapping, alternative to and similar to FIG. 12, but having a separate one of the Mapping Logic for distributed mapping included for each user and included in each user display appliance.

FIG. 14 shows a system embodiment of a mapping layer logic with edit logic and for distributed mapping, alternative and similar to FIG. 12, but where the Mapping Logic/table does not have storage or logic for a user as in FIGS. 11 and 12, and where there is an additional element in FIG. 14 that is not in FIG. 13, which additional element provides logic to define for each user a definition of the edit permission level, which provides definition and permissions as to whether or not editing is permitted for a respective particular user, and as to which level that particular user should be editing.

FIG. 18 illustrates an alternative embodiment of FIG. 15, which is similar to FIG. 15, with the exception that there is now Layer Edit Logic so that the network interface may now receive information about a layer that needs to be edited, and which provides the information to edit it, and which communicates that information to and with Layer Storage with edit logic 1700.

FIG. 22 is similar to FIG. 18 and contains all of the elements and functions of FIG. 18, with the addition of synchronization logic which, similar to FIG. 21, maintains data integrity across Network Layer Storage elements as in FIG. 18.

FIG. 23 illustrates simultaneous document collaboration, video, voice and audio communications.

FIG. 28 illustrates an embodiment of a display computing appliance with mapping storage, user display logic, user display, user layer editing logic and synchronization logic, similar to FIG. 27 with the addition of synchronization logic.

FIG. 29 illustrates music team Mapping Logic for distributed Data Layers.

FIG. 32 illustrates education Mapping Logic for distributed Data Layers.

FIG. 33 illustrates a first method of data flow for a student in an education team.

FIG. 34 illustrates an alternative data flow for the student for an education team.

FIG. 35 illustrates data flow for a teacher for an education team.

FIG. 36 illustrates education team data flow for student layer edits made by the teacher.

FIG. 37 illustrates ad hoc Mapping Logic with distributed Data Layers.

FIG. 38 illustrates data flow of user-to-user edits in an Ad Hoc team.

FIG. 39 illustrates an embodiment of display logic, where the display logic has a storage for combined Layer Data, a Display Logic Controller and a means to combine layers and where the result is then sent to the display.

FIG. 40 illustrates Layer Edit Logic.

FIG. 41 illustrates Layer Edit Logic with synchronization logic.

FIG. 47 illustrates roles within a music team, showing multiple roles and the functioning of the appliance and what layers are used by a particular appliance and how it depends on its role, and showing how any edits that may be made will depend on the role that an appliance is functioning in.

FIG. 61 illustrates a social team where the owner, Frankie, is viewing all the messages.

FIG. 62 illustrates a social team where the owner, Frankie, is viewing messages between himself and his manager, John.

FIG. 63 illustrates a social team where the owner, Frankie, is viewing is messages from his groupies.

FIG. 64 illustrates a social team where the owner, Frankie, is viewing threads of messages that he has participated in.

FIG. 65 illustrates a social team where the owner, John, is viewing all the messages.

FIG. 66 illustrates a social team where the owner, John, is viewing messages between himself and Frankie.

FIG. 67 illustrates a social team where the owner, John, is viewing threads of messages that he has participated in.

FIG. 69 illustrates a social team where the owner, Mary, is viewing all the threads she has participated in.

FIG. 70 illustrates a social team where the owner, Frankie, is viewing threads of messages that he has participated in with an expanded view.

FIG. 71 illustrates Layer Data that contains Layer Data Elements with context and content information.

DETAILED DESCRIPTION OF FIGURES

FIGS. 1-10 illustrates alternate embodiments and various configurations of the invention.

Figure 1:
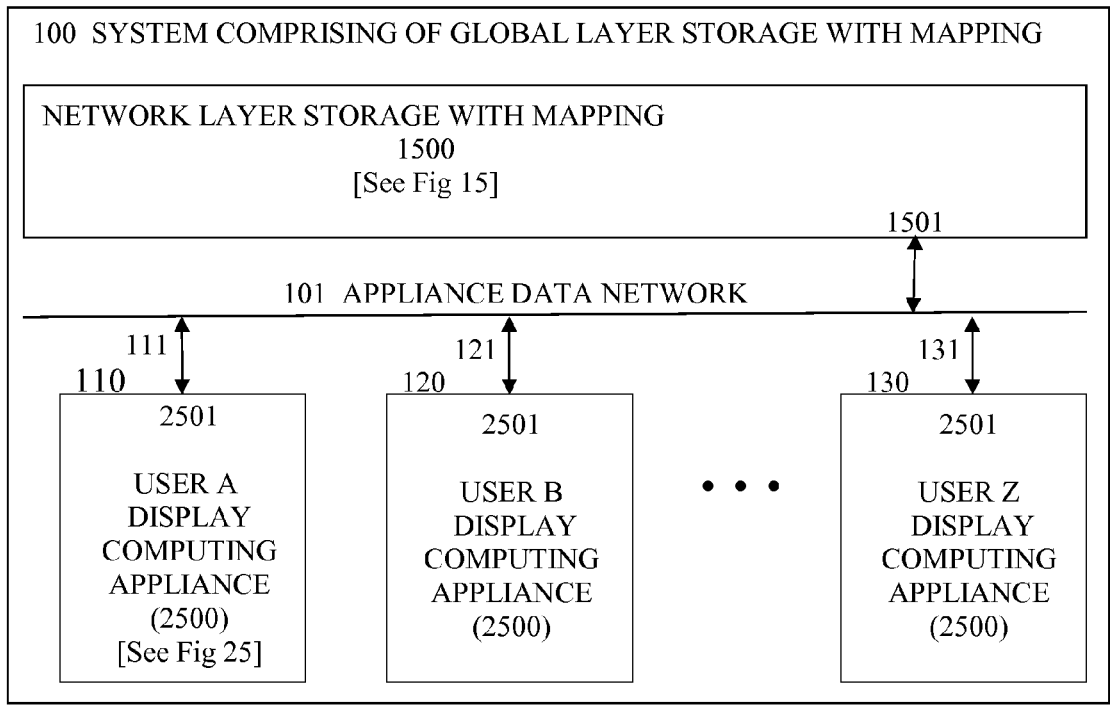
FIGS. 1-71 illustrates various configurations and embodiments of the invention with various features and functionality.

FIG. 1 illustrates a first embodiment comprising a system with Global Layer Storage with mapping. In a preferred embodiment of this system, it is comprised of Network Layer Storage, 1500, with mapping in a global location. In other words, Global Layer Storage is provided at one location that is on a connected Appliance Data Network of a plurality of appliances, communicating and providing information to the plurality of computing appliances each with their own display. The connected Appliance Data Network in this embodiment is comprised of a connection; 1501, 111, 121, 131; of each subsystem; 1500, 110, 120, 130 respectively; to the Appliance Data Network, 101. The Display Computing Appliances 110, 120 and 130. These are instances of a Display Computing Appliance 2500 as described in further detail in FIG. 25. The Network Layer Storage, 1500, is described in further detail in FIG. 15. It should be noted that in this embodiment shown in FIG. 1 and the embodiments illustrated in FIGS. 2, 3, 4, 5, 6, 7, 8, 9 and 10 that three Display Computing Appliances; as embodied in FIG. 24, 25, 26, 27 or 28; are shown but any number more than one is acceptable.

Figure 2:
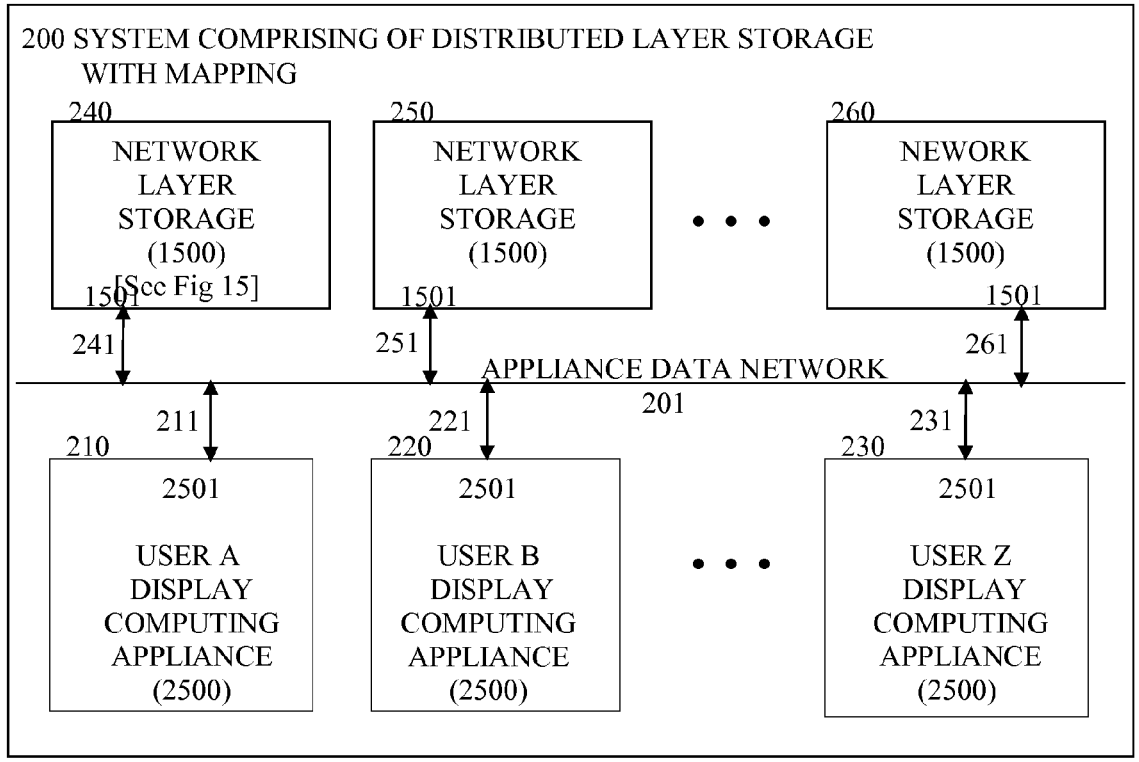
FIG. 2 illustrates a system with Distributed Layer Storage with Mapping Logic.

FIG. 2 illustrates a system with Distributed Layer Storage with mapping. There are multiple distributed networked layer storage at separate locations; 240, 250, 260; on the connected Appliance Data Network and each having mapping within the storage coupled to a plurality of user display computing appliances; 210, 220, 230; each with their own display. The connected Appliance Data Network in this embodiment is comprised of a connection; 241, 251, 261, 211, 221, 231; of each subsystem; 240, 250, 260, 210, 220, 230 respectively; to the Appliance Data Network, 201. In this embodiment a specific Data Layer is stored only once in one of the Network Layer Storage locations, 240, 250, 260. The Display Computing Appliance, 2500, is the embodiment of blocks 210, 220 and 230 and is described in further detail in FIG. 25. The Network Layer Storage, 1500, is described in further detail in FIG. 15. The number of Network Layer Storage locations and Display Computing Appliances can be the same or different. It should be noted that in this embodiment shown in FIG. 2 and the embodiments illustrated in FIGS. 4, 6, 7, 9 and 10; the physical location of the Network Layer Storage and the user display computing appliances may be in the same physical location or they may be in their own separate physical locations. Some appliances may have Network Layer Storage in the same physical location as a Display Computing Appliance or even integrated within the appliances, or some may not. The choice configuration is quite flexible and compatible with the present invention. Likewise three Network Layer Storage; embodied as shown in FIGS. 15, 18, 19, 20, 21 and 22; instances are shown in FIGS. 2, 4, 6, 7, 9 and 10 but any number above one is acceptable.

Figure 3:
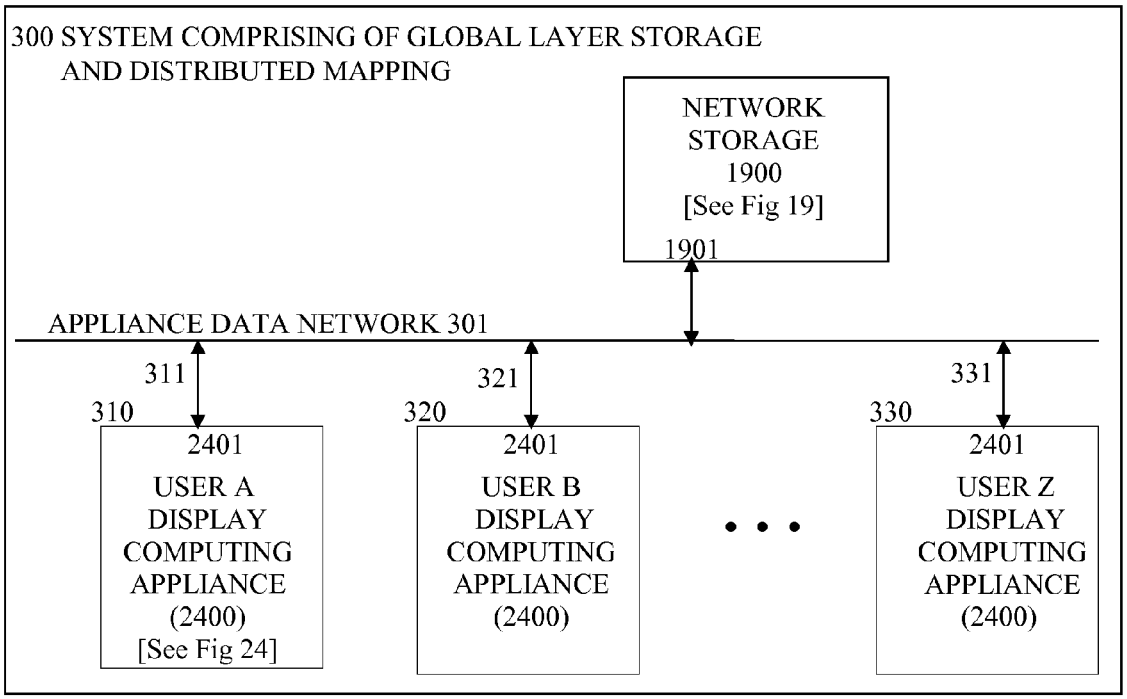
FIG. 3 illustrates a system with Global Layer Storage and distributed Mapping Logic.

FIG. 3 illustrates a system with Global Layer Storage and distributed mapping as illustrated in this embodiment. Global network storage, 1900, is concentrated in one location, communicating via the connected Appliance Data Network to a plurality of display computing appliances each having local mapping in the particular appliances to provide logic to map the global Data Layer storage. The connected Appliance Data Network in this embodiment is comprised of a connection; 1901, 311, 321, 331; of each subsystem; 1900, 310, 320, 330 respectively; to the Appliance Data Network, 301. The Display Computing Appliance, 2400, is the embodiment of subsystems 310, 320 and 330 and is described in further detail in FIG. 24. The Network Layer Storage, 1900, is described in further detail in FIG. 19.

Figure 4:
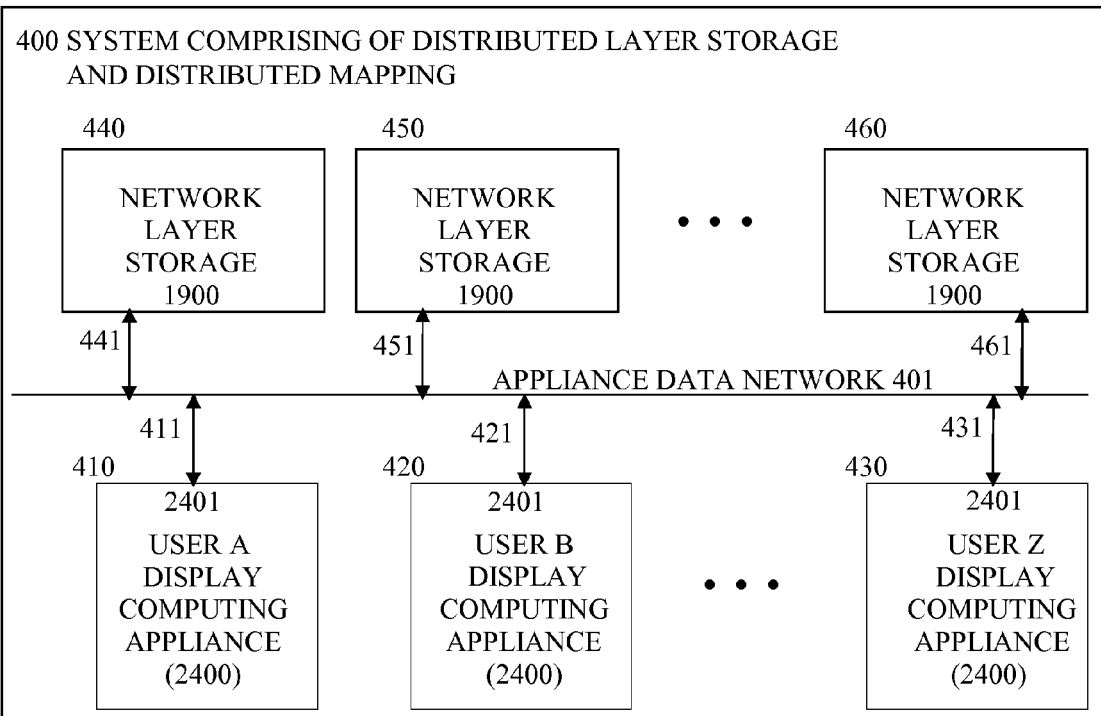
FIG. 4 illustrates a system with Distributed Layer Storage and distributed Mapping Logic.

FIG. 4 illustrates a system with Distributed Layer Storage and distributed mapping, as illustrated in FIG. 4, the system here has a plurality of networked layer storage locations; 440, 450, 460; which are in communication via the connected Appliance Data Network with a plurality of user display computing appliances; 410, 420, 430; which each containing a display and mapping for the layer storage. The connected Appliance Data Network in this embodiment is comprised of a connection; 441, 451, 461, 411, 421, 431; of each subsystem; 440, 450, 460, 410, 420, 430 respectively; to the Appliance Data Network, 401. In this embodiment a specific Data Layer is stored only once in one of the Network Layer Storage locations, 440, 450, 460. The Display Computing Appliance, 2400, is the embodiment of subsystems 410, 420 and 430 and is described in further detail in FIG. 24. The Network Layer Storage, 1900, is the embodiment of subsystems 440, 450 and 460 and is described in further detail in FIG. 19.

Figure 5:
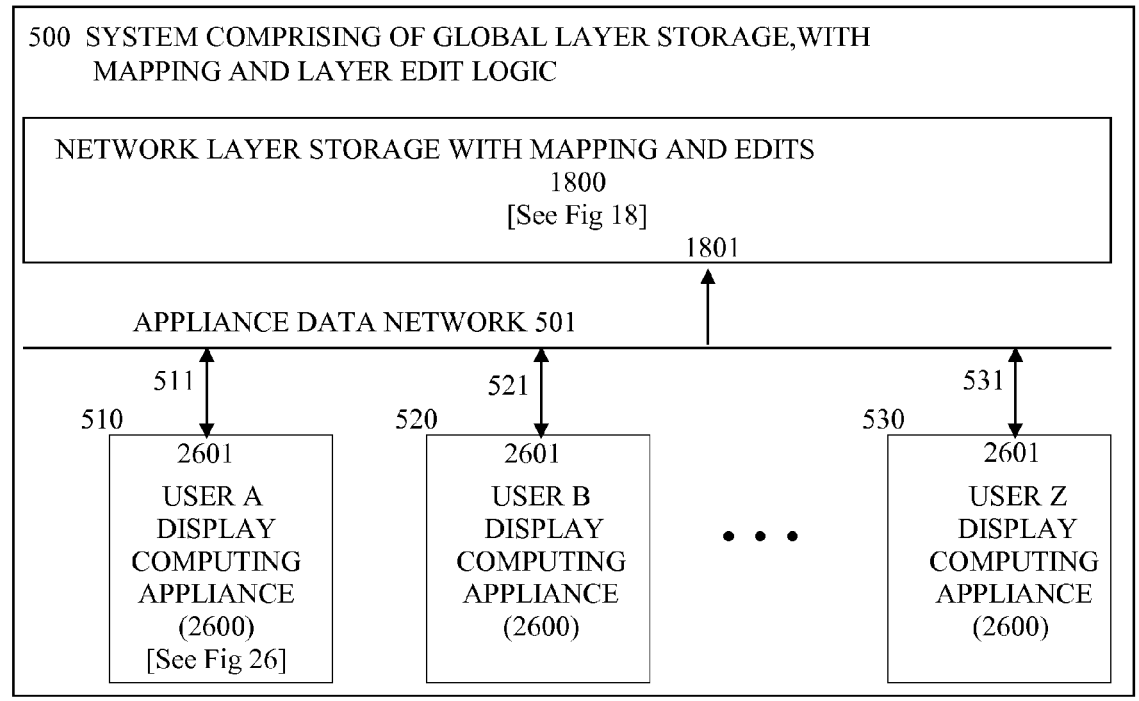
FIG. 5 illustrates an embodiment of a system with Global Layer Storage with Mapping Logic and layer-edit logic.

FIG. 5 illustrates an embodiment of a system with Global Layer Storage with mapping and layer-edit logic. This is similar to FIG. 1 with the exception that editing logic is added to both the Network Layer Storage and to each display-computing appliance. Thus, particular layers can be edited by a selected user, and results in causing modifications to the respective layer storage, and in accordance with one aspect of the present invention, can also selectively alter the composite display presentation on one or more selected ones of the user display computing appliances, depending on the mapping provided. The connected Appliance Data Network in this embodiment is comprised of a connection; 1801, 511, 521, 531; of each subsystem; 1800, 510, 520, 530 respectively; to the Appliance Data Network, 501. The Display Computing Appliance, 2600, is the embodiment of subsystems 510, 520 and 530 and is described in further detail in FIG. 26. The Network Layer Storage, 1800, is described in further detail in FIG. 18.

Figure 6:
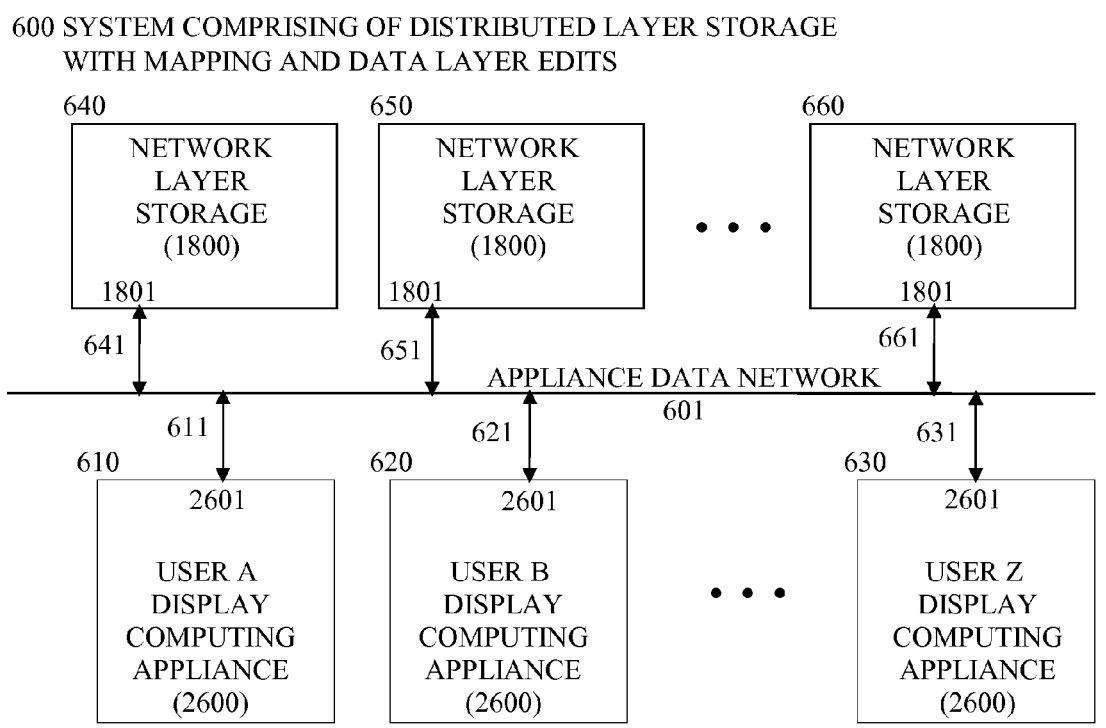
FIG. 6 illustrates embodies a system with Distributed Layer Storage with Mapping Logic and Data Layer Edit Logic.

FIG. 6 illustrates an embodiment of a system with Distributed Layer Storage with mapping and Data Layer edits. This is similar to FIG. 2 with the exception that editing logic has been added to both the Network Layer Storage. There are a plurality of Network Layer Storage memory; 640, 650, 660; and a plurality of user display computing appliances; 610, 620, 630; each and all of which has editing logic added to facilitate selectively allowing the user to make changes to the respective zero, one or more layers as determined by the Mapping Logic. The connected Appliance Data Network in this embodiment is comprised of a connection; 641, 651, 661, 611, 621, 631; of each subsystem; 640, 650, 660, 610, 620, 630 respectively; to the Appliance Data Network, 601. In this embodiment a specific Data Layer is stored only once in one of the Network Layer Storage locations, 640, 650, 660. The Display Computing Appliance, 2600, is the embodiment of subsystems 610, 620 and 630 and is described in further detail in FIG. 26. The Network Layer Storage, 1800, is the embodiment of subsystems 640, 650 and 660 and is described in further detail in FIG. 18.

Figure 7:
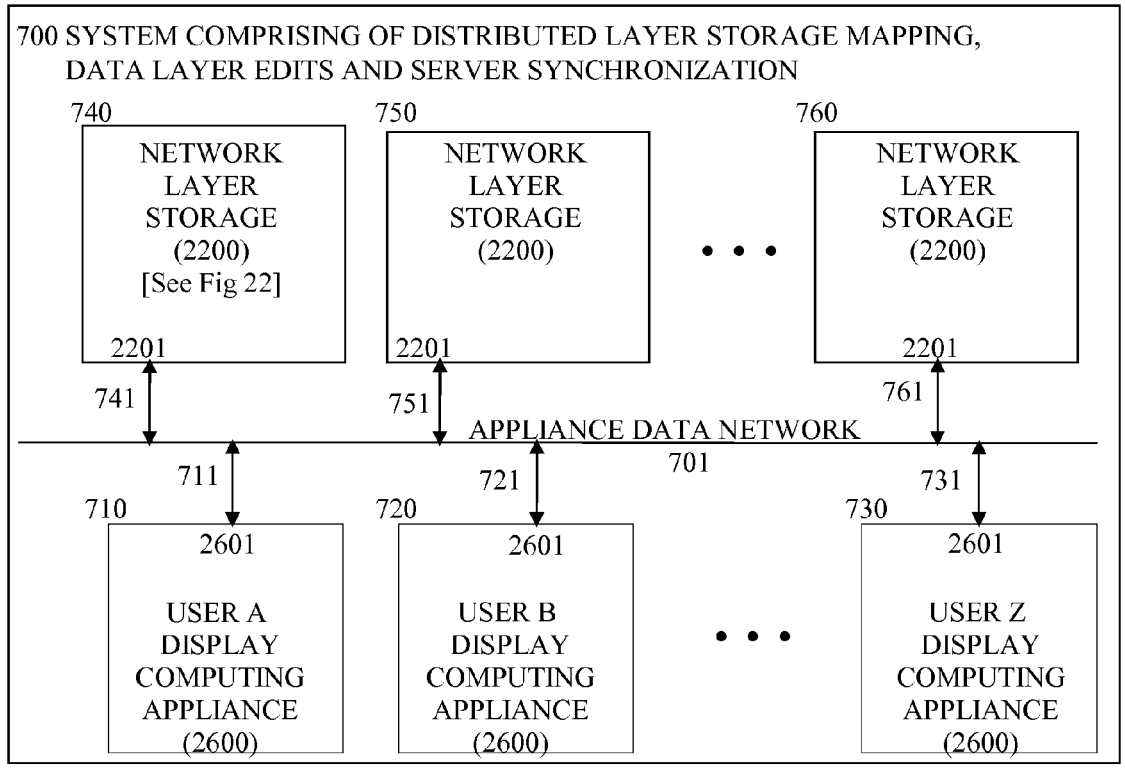
FIG. 7 illustrates an embodiment of a system with Distributed Layer Storage with mapping and Data Layer Edit Logic and server synchronization.
Figure 9:
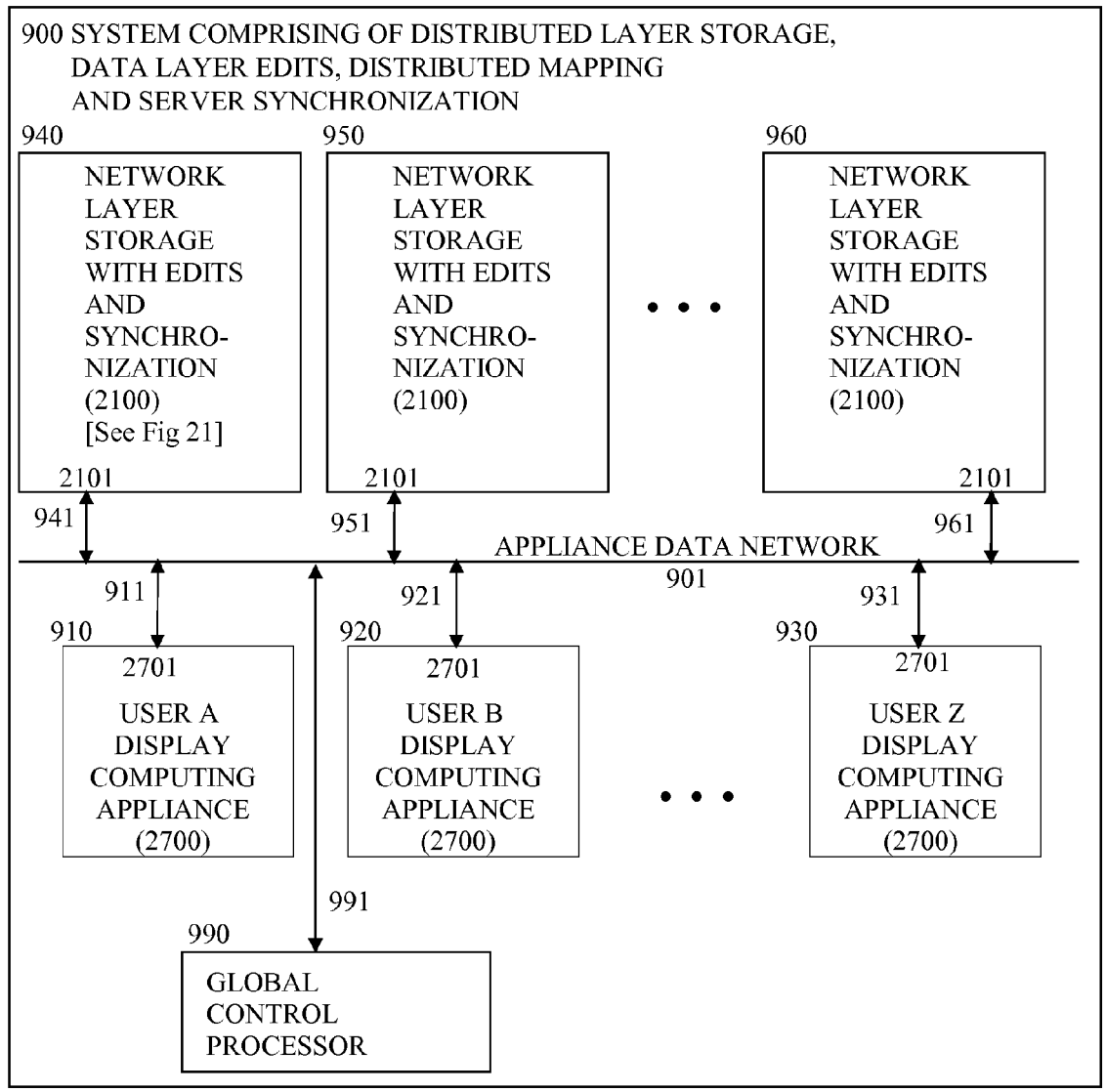
FIG. 9 illustrates an embodiment of a system of Distributed Layer Storage, Data Layer Edit Logic, distributed mapping and server synchronization.
Figure 10:
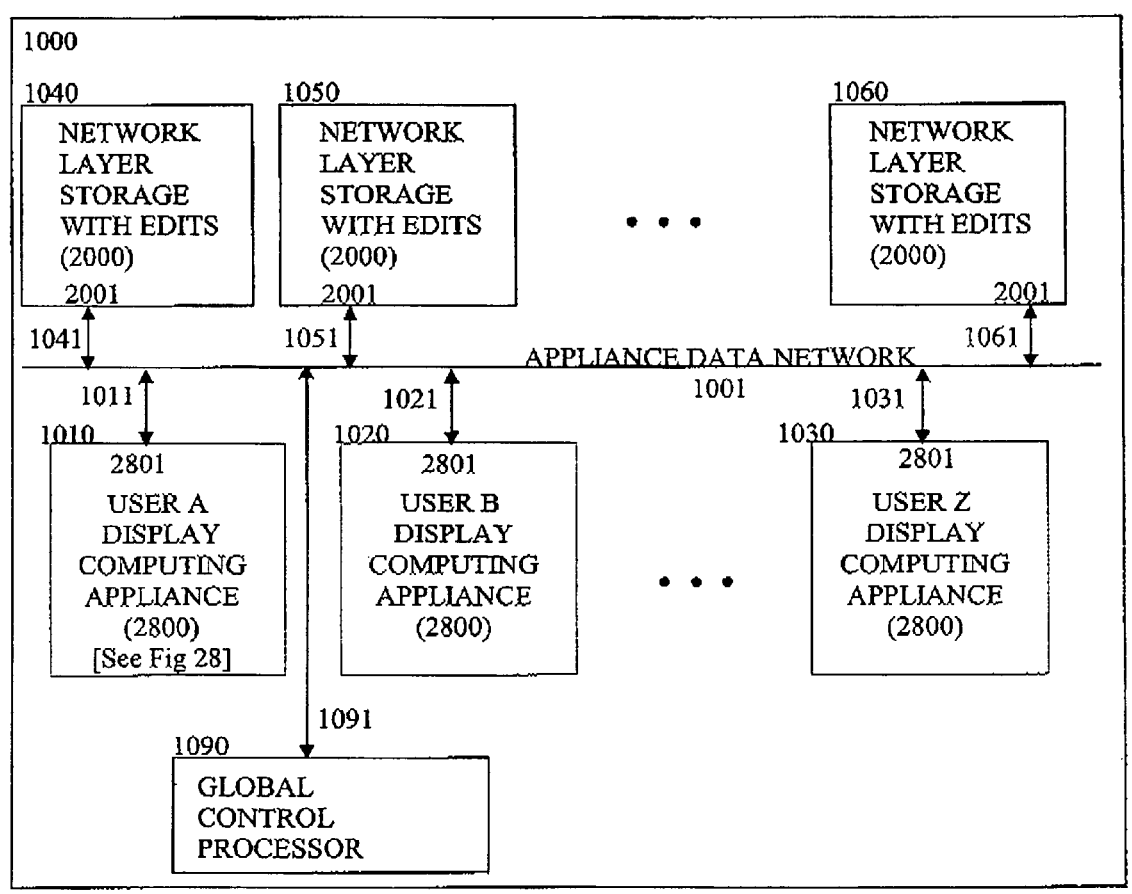
FIG. 10 illustrates embodies a system of Distributed Layer Storage, Data Layer Edit Logic, distributed mapping and client synchronization.

FIG. 7 illustrates an embodiment of a system with Distributed Layer Storage with mapping and Data Layer edits and server synchronization. This system is similar to FIG. 6 with the exception that each of the Network Layer Storage devices has server synchronization provided for and included in the storage device. The connected Appliance Data Network in this embodiment is comprised of a connection; 741, 751, 761, 711, 721, 731; of each subsystem; 740, 750, 760, 710, 720, 730 respectively; to the Appliance Data Network, 701. The Display Computing Appliance, 2600, is the embodiment of subsystems 710, 720 and 730 and is described in further detail in FIG. 26. The Network Layer Storage, 2200, is the embodiment of subsystems 740, 750 and 760 and is described in further detail in FIG. 22. This embodiment includes the synchronization logic with the Network Layer Storage, 2200. The embodiment illustrated in this FIG. 7 and the embodiments illustrated in FIGS. 9 and 10 provide for synchronization that allows for the same updated data for a respective particular layer to be stored in memory devices at multiple locations in each one of the Network Layer Storage devices, and allows the display computing appliances to access that respective layer from any one of the Network Layer Storage devices. The server synchronization provides the logic that makes sure that when a change is made to a layer in one of the Network Layer Storage devices that the change is communicated to all of the other Network Layer Storage devices that have the same respective layer stored in them, so that the respective layer has its Layer Data updated to contain the same information. This allows for a much more flexible storage network and the Network Layer Storage devices can optionally be, or not be, physically co-located with a respective one of the user display appliances. Alternative, or additionally, some of the user display appliances may have Network Layer Storage, while others do not. Also, it is not a requirement of the present invention that all layers are stored in each and all Network Layer Storage devices. The synchronization is only required when at least two of the Network Layer Storage devices contain a same respective layer, ie., duplicate copies, so that those storage devices can be maintained to have identical Layer Data stored for that respective same layer. In addition, there is no restriction on how many locations a particular layer is duplicated. Obviously, this provides for a very flexible choice of storage options that allows for static or dynamic allocation of storage for layers which can be optimized for tradeoffs in storage requirements, network traffic/bandwidth/latency and the complexity of managing multiple copies storage.

Figure 8:
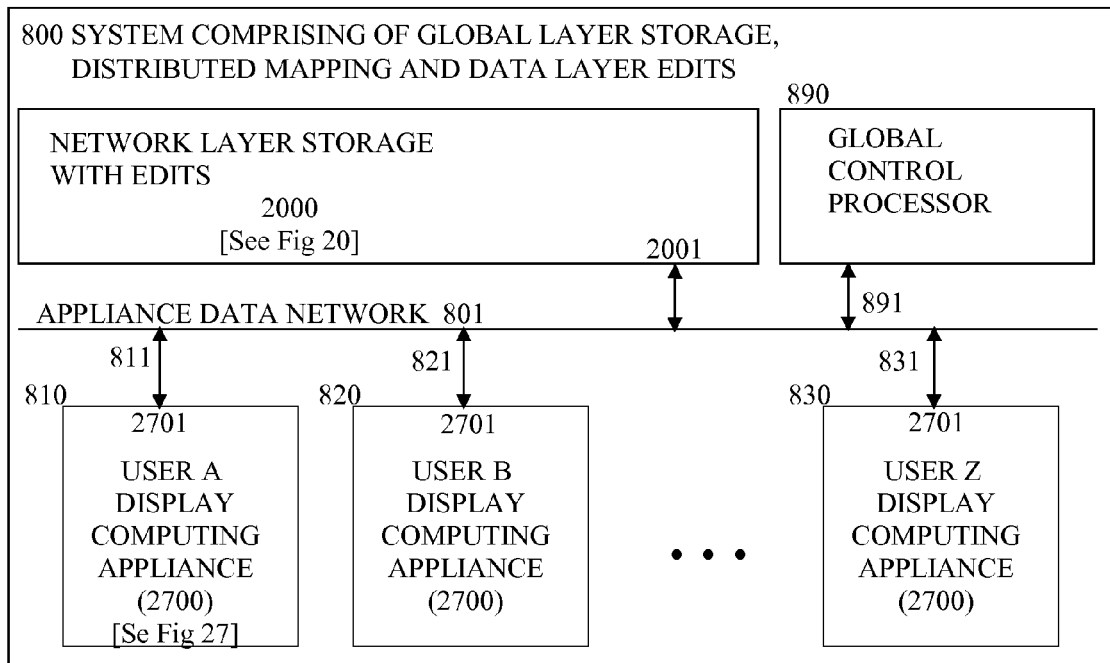
FIG. 8 illustrates an alternative system similar to FIG. 3, and shows an embodiment of a system of layered data storage with Global Data Layer Storage, distributed mapping and Data Layer Edit Logic.

FIG. 8 illustrates an embodiment of a system is similar to FIG. 3. FIG. 8 illustrates an embodiment of a system of layered data storage with global Data Layer storage, distributed mapping and selectively providing for Data Layer edits. In this illustrated embodiment of the system, there is a centralized global Network Layer Storage coupled for communication with multiple computing display appliances. The Mapping Logic is done at each appliance and, different from the system of FIG. 3. There is Edit Logic which has been added to each user display computing appliance and to the Network Layer Storage, so that for a selectively enabled user, the enabled user can make changes to a particular respective mapped edit layer. In addition, a Global Control Processor, 890, is included which works in conjunction with the Control Processors in the Display Computing Appliances, 810, 820, 830. The connected Appliance Data Network in this embodiment is comprised of a connection; 2001, 811, 821, 831, 891; of each subsystem; 2000, 810, 820, 830, 890 respectively; to the Appliance Data Network, 801. The Display Computing Appliance, 2700, is the embodiment of subsystems 810, 820 and 830 and is described in further detail in FIG. 27. The Network Layer Storage, 2000, is described in further detail in FIG. 20. Note that the Global Control Processor, in this embodiment and in the embodiments illustrated in FIGS. 9 and 10, is not required to be present. Some systems do not require centralized coordination of activities and the Global Control Processor would have nothing to do so can be eliminated.

FIG. 9 illustrates an embodiment of a system of Distributed Layer Storage, Data Layer edits, distributed mapping and server synchronization. This is similar to FIG. 4 with the exception that logic and storage to selectively permit Data Layer edits have been added so that selectively enabled ones of the users may change data stored for a particular layer, and there is server synchronization. The server synchronization logic in the Network Layer Storage, 2100, allows change data for a layer to be stored in multiple Network Layer Storage devices and locations and the server synchronization makes sure that once a change is made to Layer Data for a respective layer in one network storage device and location that the respective change to the respective Layer Data is synchronized and that an identical change is to respective Layer Data in all other locations that said respective layer exists. The connected Appliance Data Network in this embodiment is comprised of a connection; 941, 951, 961, 911, 921, 931, 991; of each subsystem; 940, 950, 960, 910, 920, 930, 990 respectively; to the Appliance Data Network, 901. The Display Computing Appliance, 2700, is the embodiment of subsystems 910, 920 and 930 and is described in further detail in FIG. 27. The Network Layer Storage, 2100, is the embodiment of subsystems 940, 950 and 960 and is described in further detail in FIG. 21. In the illustrated embodiment of FIG. 9, the user display-computing appliance may selectively access a respective layer from any of the network storage devices and locations that contains that respective layer. The user display-computing appliance also contains Edit Logic to selectively allow the user to make and communicate changes to the Network Layer Storage.

FIG. 10 illustrates an embodiment of a system of Distributed Layer Storage, Data Layer edits, distributed mapping and client synchronization. This is similar to FIG. 9 with a difference being that the synchronization is contained in the user display computing appliance and not the Network Layer Storage. Thus, in the embodiment of FIG. 10, it is the responsibility of each user display-computing appliance that when there is a change made at that respective user display-computing appliance to data for a respective layer in one network storage layer location that the user display-computing appliance synchronizes the change in the data for the respective layer so as to make the change in the data for the respective layer in all the network storage devices and locations so as to maintain that the respective data for the respective layer is identical in all layer storage devices. In this embodiment, the user display-computing appliance can selectively access the respective Data Layer from any one of the network storage devices/locations and the network storage layer device/location can be (or not be) co-located with each user display-computing appliance. The connected Appliance Data Network in this embodiment is comprised of a connection; 1041, 1051, 1061, 1011, 1021, 1031, 1091; of each subsystem; 1040, 1050, 1060, 1010, 1020, 1030, 1090 respectively; to the Appliance Data Network, 1001. The Display Computing Appliance, 2800, is the embodiment of subsystems 1010, 1020 and 1030 and is described in further detail in FIG. 28. The Network Layer Storage, 2000, is the embodiment of subsystems 1040, 1050 and 1060 and is described in further detail in FIG. 20.

FIG. 11 illustrates an embodiment of the mapping storage logic with Edit Logic and layer partitioning logic for global mapping. This mapping storage logic is used when the Mapping Logic is distributed and therefore each user at each user display-computing appliance is capable of having their own information for their mapping. The Mapping Logic is responsive to the display logic, which determines when to update the display. The display logic selects a particular user and communicates that to user input, 1111. The level input, 1112, is responsive to the display logic which starts with level 0 to obtain the first Data Layer pointer, 1113, and part, 1114, for the first layer of the display. The Network Layer Storage is responsive to the Data Layer pointer and part. The display logic in turn is responsive to the Network Layer Storage and receives the first desired portion of Layer Data. The display logic then increments the level to 1 to obtain the second portion of Layer Data for combining with the first layer for the display. The display logic continues to increment the level and combining the resulting portion of Layer Data with previous portions of Layer Data until an invalid Data Layer pointer is obtained indicating that no more layers are to be included in the display. The ordering of the Data Layers for display, since a layer layered hierarchically for display on top of another one may be different in appearance than the layers ordered the other way. The mapping table, 1110, provides a mapping (such as a pointer or data layer name) to each of the Data Layers that should be used and a description of the part of the Layer Data to use. For instance, one may want to only display the top part of the Data Layer so display mapping layers for the part would indicate that the Data Layer for only the top part be used for display. This Mapping Logic, 1100, also includes an Edit Logic, 1120, (such as a table with control logic) which is used to determine which layer should be used for editing for which user at each user display-computing appliance and when editing is to be allowed. The Edit Logic requires that it be indicated which user it is that the information is wanted for on the edit user input, 1121, and it provides the edit level on edit level output, 1122, which would then be used later in the Mapping Logic (or table) to find the particular pointer to the Data Layer which the changes would then be made to, and stored in. This storage Mapping Logic also includes an input to the Edit Logic (table), 1120, to be able to change the edit level in the Edit Logic for a particular user responsive to the mapping control logic. The Mapping Logic (table), 1110, also has inputs for the user, 1115, level, 1116, Data Layer, 1117, and part, 1118, to allow the mapping control logic to make changes to these mapping tables for the operation of the system. The Mapping Table Data Example, 1130, shows a case where there are 3 users and 4 Data Layers. User A is displaying 2 different layers. User B is displaying 2 layers, 1 of which is shared with user A and B. User C is displaying 4 layers, 1 of which is shared with user A and B, another is shared only with B, another is shared only with A, and the last layer is only displayed by C. In addition, user B is displaying a different part of the layer than either A or C. The Edit Table Data Example, 1140, shows a case, in conjunction with the Mapping Table Data Example, wherein user A is editing Data Layer 2, user B is editing Data Layer 3 and user C is editing Data Layer 4. User Input, 1121, is a dual purpose input. It selects a row based upon the user using the system, and gets/sets data value in table based on control input. Inputs and outputs for FIG. 11 are shown as coupled in FIGS. 18 and 20. The embodiment in FIG. 11 is compatible for distributed or centralized use.

FIG. 12 illustrates an embodiment of a system with Mapping Logic with layer partitioning for global mapping. This is similar to FIG. 11 with the exception that it does not include the Edit Logic, 1120, that is in FIG. 11. Table 1210 is similar to table 1110. Signals 1211, 1212, 1213, 1214, 1215, 1216, 1217 and 1218 are similar to signals 1111, 1112, 1113, 1114, 1115, 1116, 1117 and 1118 respectively. Other than that, the operation of this is similar to that of the system of FIG. 11. Example data for table 1210 is shown in 1230. Inputs and outputs for FIG. 12 are shown as coupled in FIG. 15. The embodiment in FIG. 12 is compatible for distributed or centralized use.

FIG. 13 shows the embodiment of a Mapping Logic for distributed mapping. This is similar to FIG. 12 except that with distributed mapping, there is a separate one of the Mapping Logic included for each user that is included in the user display-computing appliance. However, there is only the one user information in the Mapping Logic or table for each user, and therefore, there is no user input in this mapping table to select an entry by user, since the Mapping Logic in the user appliance all applies to a particular respective user. Again, the Mapping Logic is responsive to the display logic, which determines when to update the display which increments the level to obtain the Data Layer pointers and part information to find the associated part of the associated Data Layer in the correct order to create a combined display. The mapping control logic has input to the Mapping Logic (table) in order to modify the values of the table during operation. Table 1310 is similar to table 1210. Signals 1312, 1313, 1314, 1316, 1317 and 1318 are similar to signals 1212, 1213, 1214, 1216, 1217 and 1218 respectively. Other than that, the operation of this is similar to that of the system of FIG. 12. Example data for table 1310 is shown for three users in 1330, 1331 and 1332. Inputs and outputs for FIG. 1.3 are shown as coupled in FIG. 24.

FIG. 14 shows the embodiment of mapping layer logic with edits and for distributed mapping. Table 1410 operates exactly as Table 1310 in FIG. 13. Edit Table 1420, is similar to operation as Edit Level 1120 except that with distributed mapping, there is a separate one of the Edit Level included for each user that is included in the user display-computing appliance. However, there is only the one user information in the Edit Level for each user, and therefore, there is no user input to select an entry by user, since the Edit Level in the user appliance all applies to a particular respective user. Signals 1122 and 1123 are similar to signals 1422 and 1423 respectively. The edit level provides a mapping for a respective user at a respective user display-computing appliance, which mapping determines which Data Layer is a respective assigned level that the particular user should be using for editing. It should be noted that there is also an ability to put a value in the edit level that would indicate that the user is not able to edit any level. As one example, for no edit permission, the edit level could be set to an invalid level value, and if that value was accessed by the edit Mapping Logic (e.g., mapping table), it would provide an invalid Data Layer pointer, and therefore, no Edit Data Layer would be assigned, and thus, nothing could be edited for that respective user. Example data for table 1410 is shown for three users in 1430, 1431 and 1432. Example data for edit level 1420 is shown for three users in 1440,1441 and 1442. Inputs and outputs for FIG. 14 are shown as coupled in FIG. 27 or 28.

Figure 15:
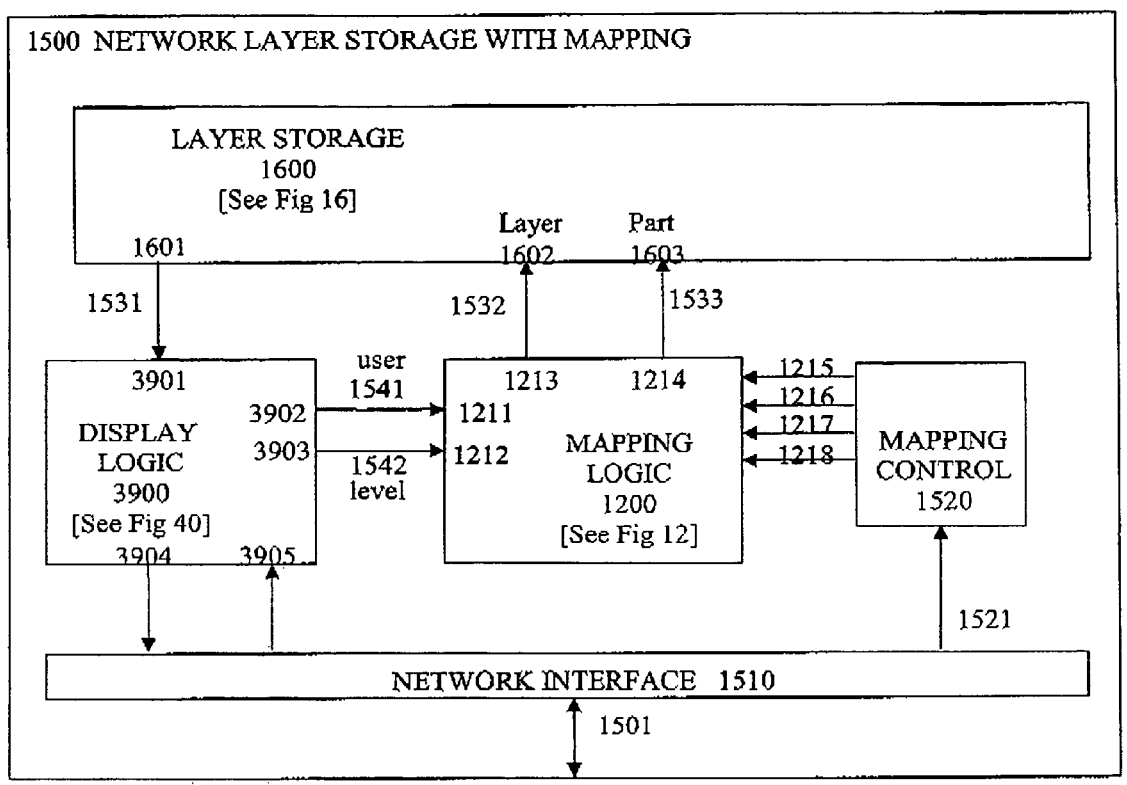
FIG. 15 illustrates the Network Layer Storage with mapping, and with, inter alia, layer storage display logic, which combines the layers dependent on the Mapping Logic.

FIG. 15 illustrates an embodiment of Network Layer Storage with mapping. This embodiment comprises layer storage display logic, which selectively combines for use in display respective selected ones of the layers responsive to the Mapping Logic. Layer data is obtained from layer storage, 1600, (further described in FIG. 16) on data path 1601 which is coupled via 1531 to signal 3901 of the display logic, 3900, (further described in FIG. 39). The desired layer data is selected by signal layer, 1602, and signal part, 1603, which specify which data layer and what part of the data layer to retrieve in layer storage 1600. Signal 1213 is coupled to 1602 via 1532 and signal 1214 is coupled to 1603 via 1533 from the mapping logic 1200 (further described in FIG. 12). The mapping logic, 1200, is setup through the signals 1215, 1216, 1217, and 1218 sent from mapping control, 1520. The mapping control is responsive to messages sent through the connected Appliance Data Network, 1501, translated by the network interface, 1510, and coupled via 1521 to the mapping control, 1520, from a plurality of Control Processors 2550 (see FIG. 25) to allow the Mapping Logic, 1200, to be modified. The Control Processors send messages based on role of the user and the specific embodiment. The modifications of the Mapping Logic, 1200, control which Data Layers are combined for display and their order for each user. The display logic, 3900, (further described in FIG. 39) generates the signal user, 3902 and signal level, 3903, which is coupled to the mapping logic, 1200, to signals 1211 and 1212 via 1541 and 1542 respectively. The layer data retrieved, 3901, previously described herein, is combined into display presentation data for the user on signal 3904. Signal 3904 is coupled to network interface, 1510, that sends the display presentation data via the appliance data network, 1501, to the appropriate display computing appliance. The display logic, 3900, obtains layer data combination parameters via signal 3905 that control how the layer data is combined. Signal 3905 is coupled to the network interface, 1510, which receives the layer data combination parameters. from the appliance data network, 1501, from a plurality of Control Processors. Mapping Control, 1520, sets up all of the values for the edit table and the mapping table, and what layers are being used .by which users, and what layers each user can be editing. User inputs, display data and program data are coupled via network interface 1510.

Figure 16:
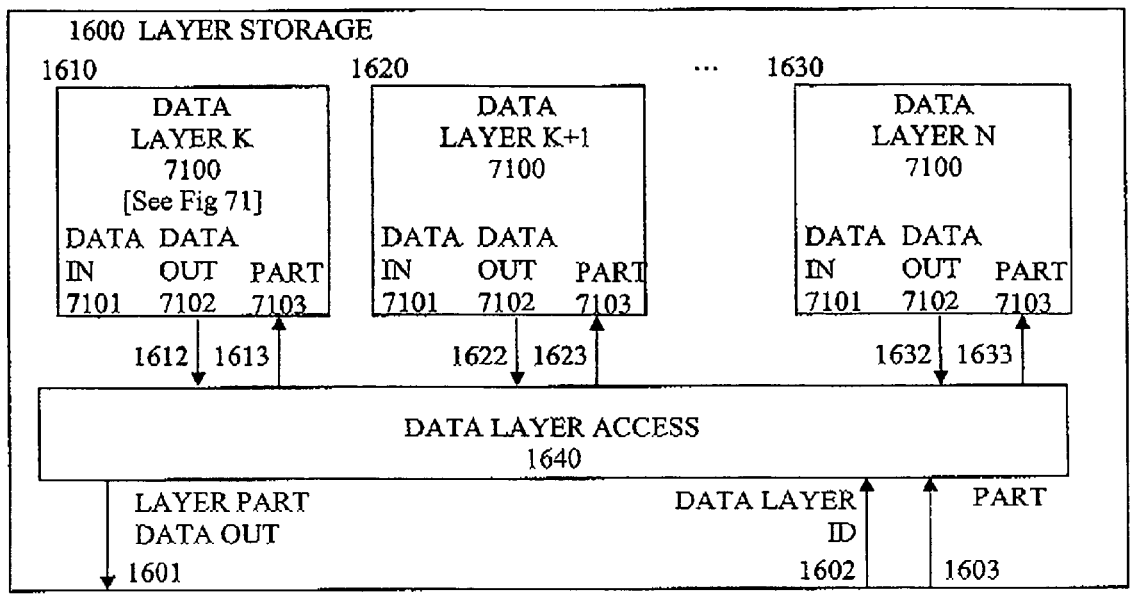
FIG. 16 illustrates details of the Layer Storage (as shown in FIG. 15 and several other illustrated embodiments as illustrated and described elsewhere herein).
Figure 71:
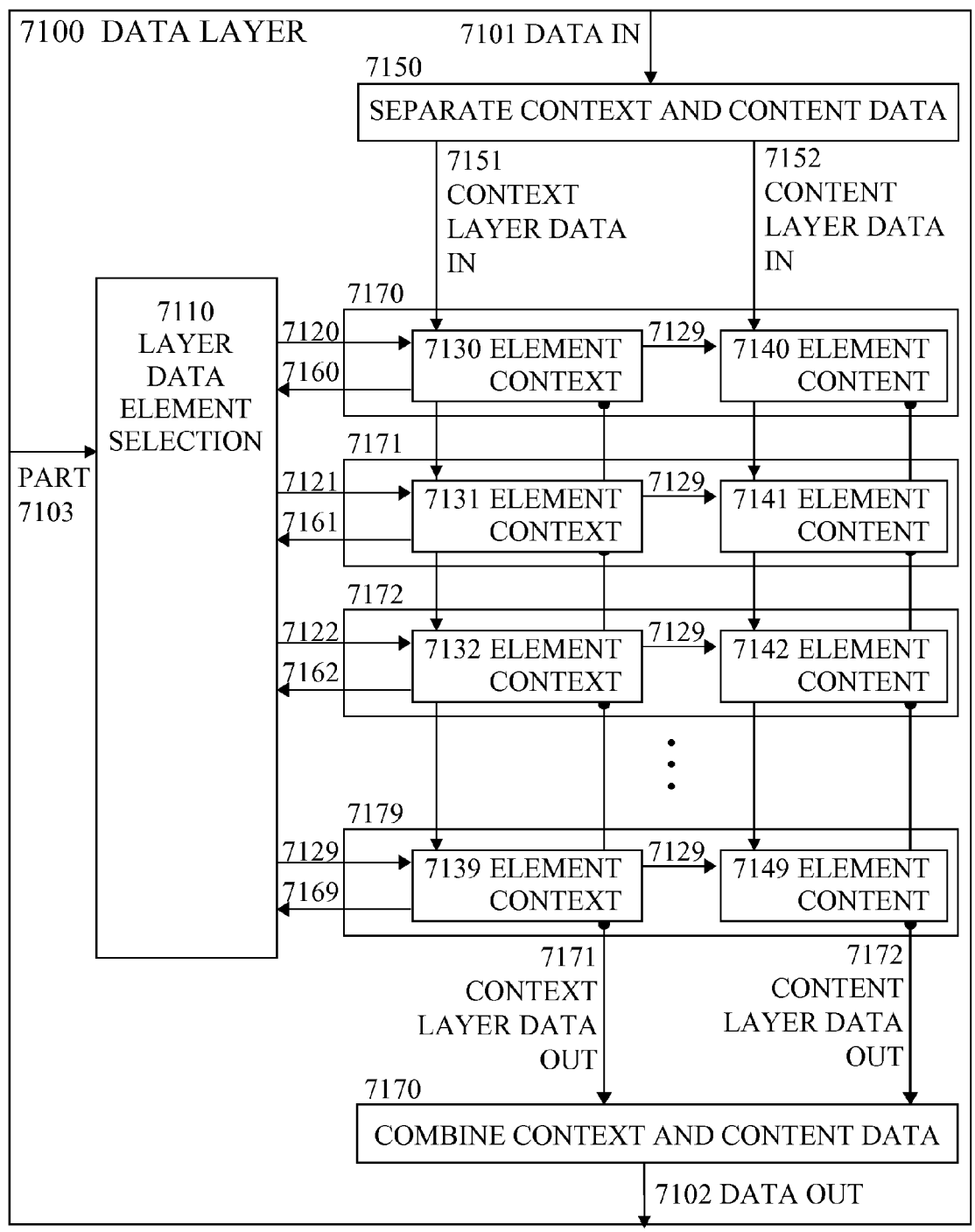

FIG. 16 illustrates an embodiment of a system showing layer storage, as illustrated and utilized in FIG. 15 and other embodiments. In this embodiment, there are multiple Data Layers, 1610, 1620, 1630, storing Layer Data and there is Layer Data Access Logic, 1640, to allow the system to access a particular Data Layer. The Data Layers, 1610, 1620, 1630 are each illustrated in block 7100 as shown in FIG. 71. Layer Storage 1600 does not use the Data In, 7101, input of Data Layer 7100 in elements 1610, 1620, 1630. The system is not limited to three Data Layers, there may be any number of Data Layers at any given time. The Data Layer Access Logic provides a mapping (e.g., a pointer or data layer name) for a respective particular Data Layer responsive to Mapping Logic, 1200 in FIG. 15 in one embodiment. The Data Layer ID, 1602, input (responsive to the layer output, 1213, FIG. 12, in said embodiment) identifies a particular Data Layer; 1610, 1620, or 1630. The part, 1603, is coupled via 1533 to the part, 1214, that defines a portion of said Layer Data which is communicated via connection 1613, 1623 or 1633 respectively. The data layer access, 1640, is coupled with signals 1602 and 1603. Signal 7103 of 1610 is coupled to 1613. Signal, 7103 of 1620 is coupled to 1623. Signal 7103 of 1630 is coupled to 1633. Signal 7102 of 1610 is coupled to 1612. Signal 7102 of 1620 is coupled to 1622. Signal 7102 of 1630 is coupled to 1632. The signal 1603 is sent to one of the signals 1613, 1623 or 1633 depending on the signal 1602. The corresponding data output, 1612, 1622 or 1632, respectively provides a portion of the requested Layer Data which is conveyed to the Layer Part Data Out, 1601, by means of the Data Layer Access, 1640. This provides the means to access a particular Data Layer and provides for output of the respective Layer Part Data Out, 1601, of Layer Data.

Figure 17:
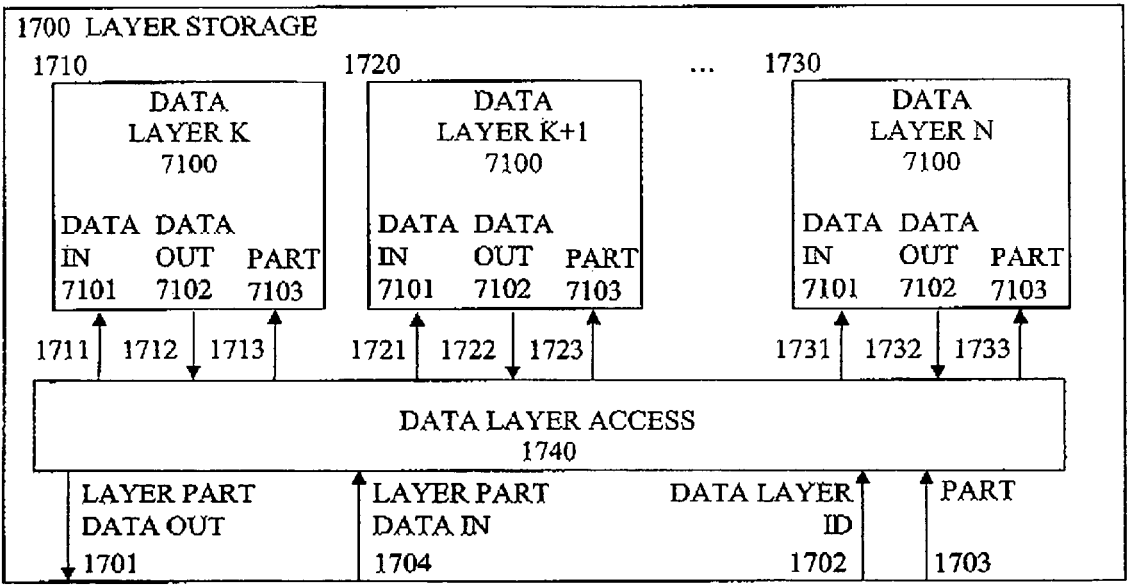
FIG. 17 shows an embodiment of Layer Storage with edit logic.

FIG. 17 illustrates an embodiment of a layer storage with Edit Logic for edits. This is used in various embodiments. It is similar to FIG. 16 with all the same functions of FIG. 16, plus with the addition of the ability to accept change data for a portion of a for a specific Data Layer. In this embodiment, there are multiple Data Layers, 1710, 1720, 1730, (similar to 1610, 1620, 1630 in FIG. 16) storing Layer Data and there is Layer Data Access Logic, 1710, (similar to 1640 in FIG. 16) to allow the system to access a particular Data Layer. The Data Layers, 1710, 1720, 1730 are each an instance of subsystem 7100 as illustrated in FIG. 71. The system is not limited to three Data Layers, there may be any number of Data Layers at any given time. The Data Layer ID input, 1702, and Part input, 1703, are responsive to the Mapping Logic, 1100, Mapping Control, 1820, and Layer Edit Logic, 4000, in one embodiment described in FIG. 18. The Layer Part Data Out, 1701, provides the current state of the portion of Layer Data described by inputs 1702 and 1703. The Layer Part Data In, 1704, is change data responsive to the Layer Edit Logic's, 4000, output, 4002, (in said embodiment) is used to replace the portion of Layer Data. Layer Part Data In, 1704, is result of processing by the Layer Edit Logic, 4000, (in said embodiment) to modify the specified contents of the portion of Layer Data with changes responsive to user input. Data Layers may be created at any time by the system by specifying a Data Layer ID that does not exist in Layer Storage 1700 and providing Layer Part Data In, 1704. A Data Layer, 1710, 1720, 1730, will be eliminated when a Data Layer has contains no Layer Data. If the Data Layer ID, 1702, identifies a nonexistent Data Layer then Layer Part Data Out, 1701,contains no data. Data layer access, 1740, uses the data layer id, 1702, to select on of the data layer storage subsystems, 1710, 1720 or 1730. The layer part data in, 1704, and part, 1703 are coupled by data layer access, 1740, to the aforementioned selected subsystem, 1710, 1720 or 1730 and coupled to the corresponding data in and part inputs, 7101 in 1710 via 1711 and 7103 in 1710 via 1713, 7101 in 1720 via 1721 and 7103 in 1720 via 1723, or 7101 in 1730 via 1731 and 7103 in 1730 via 1733. The selected subsystem 1710, 1720 or 1730 modifies a portion of the layer data stored within based on the change data on data in, 7101 and the part, 7103, specifying the portion.

Figure 18:
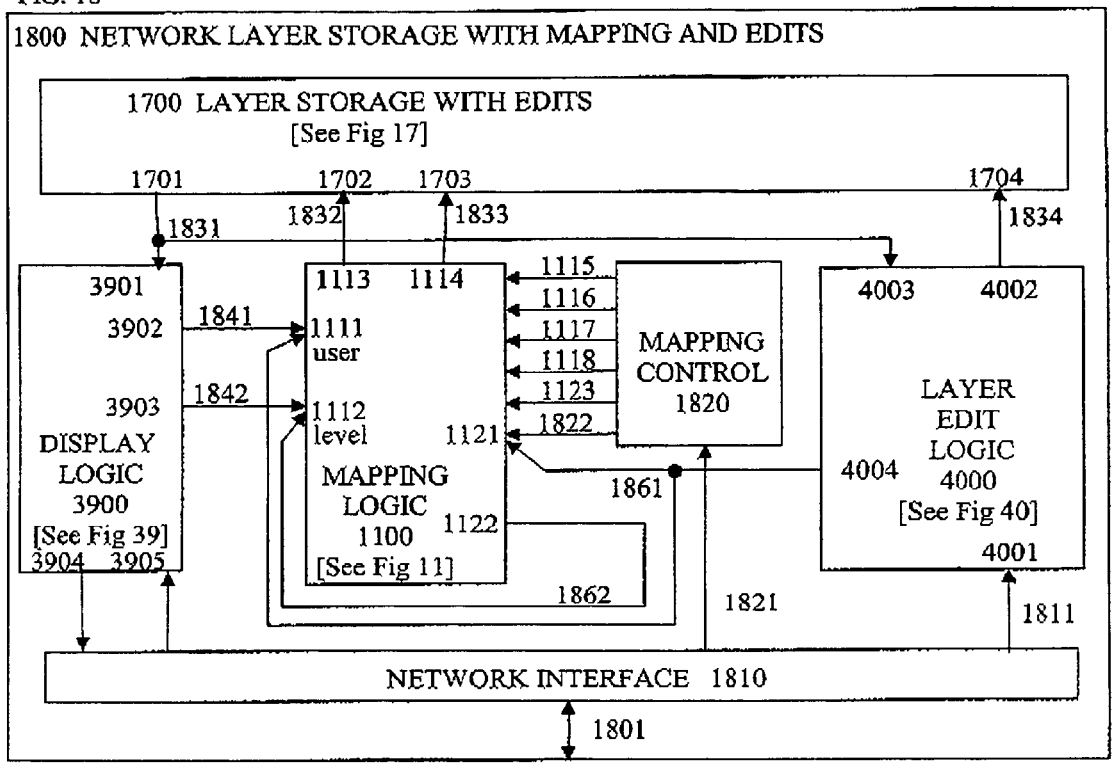
FIG. 18 shows an embodiment of a Network Layer Storage with Mapping Logic and edit logic.

FIG. 18 illustrates an alternate embodiment of the present invention, showing a system that is similar to FIG. 15 but with the addition of Layer Edit Logic, 4000, which provides for the network interface, 1810, to receive information defining permission to allow a respective selected Data Layer to be edited and provides the information on which Data Layer to edit and communicates change data from the respective user at the respective user display-computer appliance for storage in the respective Data Layer in the layer storage with edits 1700. The change data is received via the appliance data network, 1801, from a display computing appliance (see FIG. 5 or 6) which is coupled to the network interface 1810 that sends the change data via 1811 which is coupled to the Layer Edit Logic 4000, via 4001. The Layer Edit Logic is responsive to the change data provided on input 4001. This initiates a series of events. First, the user information is stripped from the change data request and output on 4004 and connected to the Mapping Logic, 1100, via 1861 to inputs 1121 and 1111. Inputs 1121 and 1111 are shared and each can independently trigger a request for the edit level. The Mapping Logic outputs the edit level on 1122 and is coupled to the level input, 1112, again a shared input via 1862. Now that the level and part are provided on inputs 1111 and 1112, the Mapping Logic outputs Layer Data pointer and part on outputs 1113 and 1114. These are connected to inputs 1702 and 1703 respectively. The layer storage is responsive to these inputs and outputs the edit portion of Layer Data on output 1701. This is information is conveyed via 1831 to input 4003 of the Layer Edit Logic, 4000. The Layer Edit Logic combines the edit portion of Layer Data with the change data and outputs the modified portion of Layer Data on 4002 which is coupled to 1704 via 1834, Finally, the layer storage with edits replaces the edit portion of Layer Data with the modified portion of Layer Data. The rest of the operation is similar to 1500 in FIG. 15. The signals 1701, 1702, 1703, 1111, 1112, 1113, 1114, 1115, 1116, 1117, 1118, 1801, 1821, 1831, 1832, 1833, 1841 and 1842 in FIG. 18 are similar in operation to 1601, 1602, 1603, 1211, 1212, 1213, 1214, 1215, 1216, 1217, 1218, 1501, 1521, 1531, 1532, 1533, 1541 and 1542 in FIG. 15 respectively and are described in detail in FIG. 15. In addition, subsystem 1700 in FIG. 18 is similar in operation to subsystem 1600 in FIG. 15 for retrieving layer data to generate the display and is described in detail in FIG. 15. Mapping Control, 1820, sets up all of the values for the edit table and the mapping table in Mapping Logic, 1100, and what layers are being used by which users, and what layers each user can be editing. User inputs, display data and program data are coupled via network interface 1810.

Figure 19:
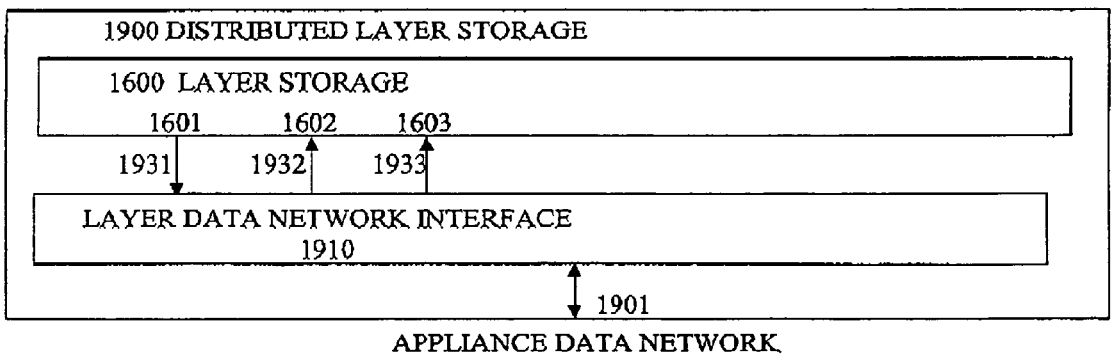
FIG. 19 shows an embodiment of a Distributed Layer Storage, with basic Layer Storage with a Layer Data network interface that allows it to communicate with the user display appliances and contains Layer Storage 1600.

FIG. 19 illustrates an alternate embodiment of the present invention showing Distributed Layer Storage. As illustrated in FIG. 19, layer storage, 1600, is illustrated with Data Layer network interface, 1910, that allows the layer storage to communicate with the user display computing appliance as shown in two embodiments in FIGS. 3 and 4. These embodiments are similar to the embodiments shown in FIGS. 1 and 2 respectively except that the Display Logic, 3900; Mapping Logic, 1300; and Mapping Control, 2420, is now located in the Display Computing Appliance, 2400. Layer Part Data Out, 1601 is coupled via 1931 to the layer data network interface, 1910, and then to network 1901 that is coupled (in FIG. 3 or 4 and 24) to the Display Logic, 3900 in one of the specific Display Computing Appliances; 310, 320, 330 or 410, 420, 430. The display computing appliance receiving the layer data is the same as the Display Computing Appliance that sends to the data Layer, 1313, and Part, 1314. Signals 1313 and 1314 are coupled through the appliance data network, 1901, (see FIG. 3 or 4 and 24) and coupled via the layer data network interface, 1910, to 1602 via 1932 and 1603 via 1933. The effective operation illustrated in FIG. 19 is the same in FIG. 15 except that the display logic, mapping logic and mapping control are moved from the layer storage and into the display computing appliance.

Figure 20:
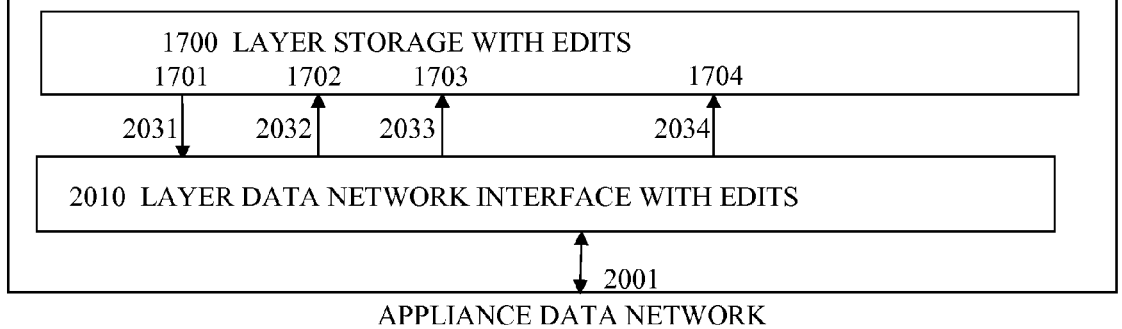
FIG. 20 illustrates an embodiment of Distributed Layer Storage structure with edit logic providing an embodiment with logic to allow the Layer Storage to be modified for editing.

FIG. 20 illustrates an alternate embodiment showing a system having Distributed Layer Storage structure with edit logic. This is similar to that shown in FIG. 19. However, this illustrated embodiment includes edit logic within Layer Storage With Edits, 1700, to selectively allow respective Data Layer in the layer storage to be modified for editing, permitting a respective user at a respective user display-computing appliance to make edits. The change data is output on 4002 in display computing appliance 2700 or 4102 in display computing appliance 2800 and coupled to the appliance data network, 2001 (see details in FIGS. 8 and 27 or FIGS. 10 and 28). The change data is coupled from the layer data network interface 2010 via 2034 to 1704. Similar to subsystem 1900, the signals 1702 and 1703 are similarly coupled from the display computing appliance via coupling 2032 and 2033 respectively to provide the layer storage with edits, 1700, the data layer and part to modify the storage based on the change data. The signals 2031, 2032, 2033 and 2001 are similar in operation to signals 1931, 1932, 1933 and 1901 for retrieving layer data and described in detail in FIG. 19. The effective operation illustrated in FIG. 20 is the same in FIG. 18 except that the display logic, mapping logic, layer edit logic and mapping control are moved from the layer storage and into the display computing appliance.

Figure 21:
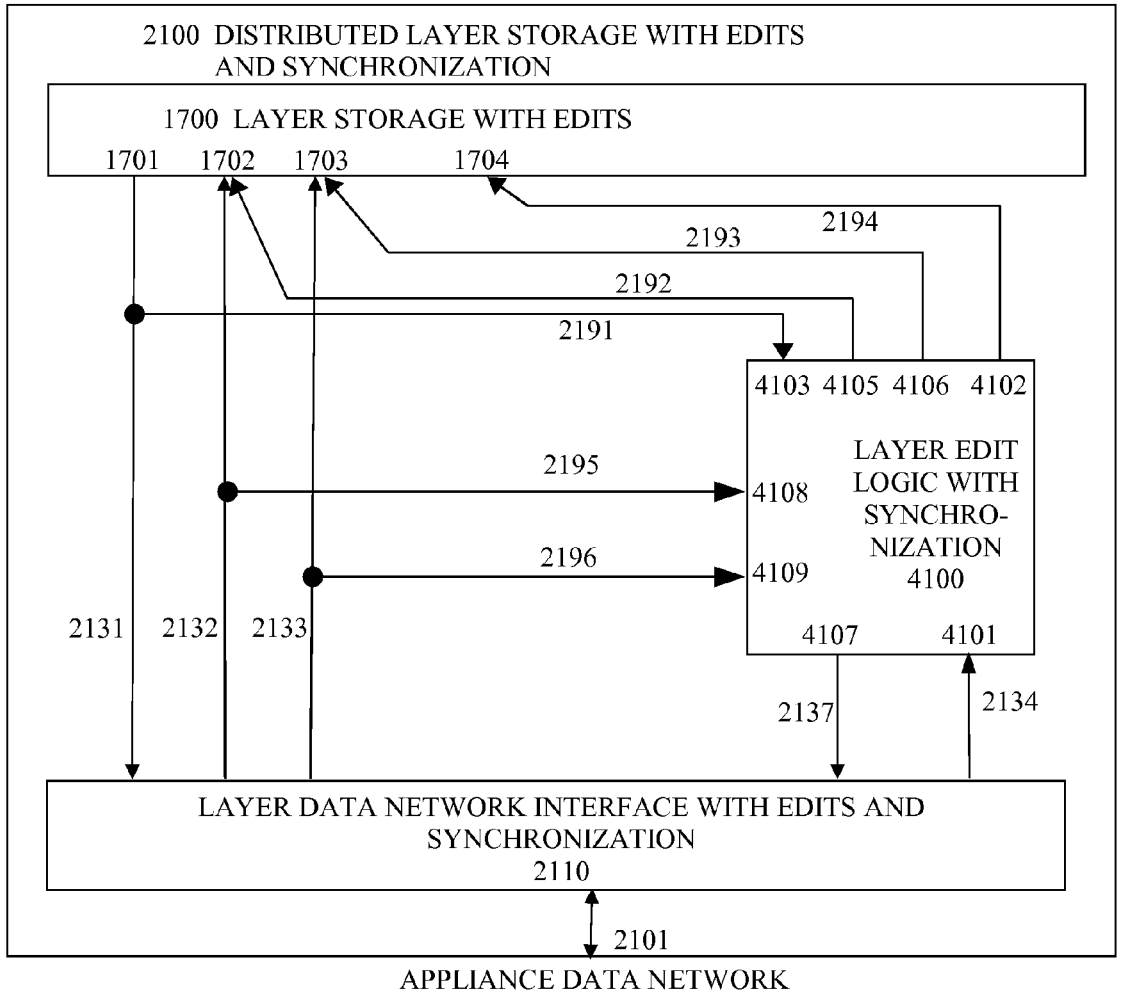
FIG. 21 shows the embodiment of a Distributed Layer Storage structure with edit logic and synchronization, similar to FIG. 20 with the addition that there is synchronization logic added so that when edits are made to a particular layer then those changes are communicated to other distributed Network Layer Storage elements to maintain the data in the proper defined layer at all places where that information needs to be stored.

FIG. 21 shows another embodiment of the present invention, showing a Distributed Layer Storage structure with edit logic and synchronization logic. This is similar to FIG. 20, with the addition of synchronization logic so that when edits are made to so as to change the Layer Data as stored in a particular layer of the Data Layers, then those changes are selectively communicated to other distributed Network Layer Storage elements for local storage of the respective change in the respective particular layer of the respective local Data Layers, so as to maintain the Layer Data in the respective Data Layer in all the places that that Data Layer is stored. Since in this embodiment, a respective particular layer can be stored in multiple elements, the system needs to have all those elements synchronized and updated so as to contain the same data, and the synchronization logic maintains that data integrity. The signals 2131, 2132, 2133, 2134 and 2101 are similar in operation to signals 2031, 2032, 2033, 2034 and 2001 for retrieving layer data and editing layer data and described in detail in FIG. 20. The only difference is that the change data, 2134, is coupled through the layer edit logic, 4100, to 4102 and then coupled by 2194 to layer data in, 1704. The synchronization logic in 4100 outputs change data information on 4107 and is coupled by 2137 to the layer data network interface, 2110, to send the change data information on the appliance data network, 2101, to the other layer storage locations that may have duplicate data layers so the layer data remains identical. When 2134 receives change data from synchronization logic in another layer storage, the synchronization logic, 4100, separates out the layer to sync, on 4105 and part to sync, 4106. The current layer data 4103 is responsive to 4105 and 4106 by coupling 4105 to 1702 via 2192 and coupling 4106 to 1703 via 2193. 1701 is responsive to 1702 and 1703. 1701 is coupled to 4103 via 2191. Finally, 4102 is responsive to both 2134 and 4103 and is coupled to 1704 via 2194 which replaces the change data in the layer storage, 1700. The effective operation illustrated in FIG. 21 is the same in FIG. 22 except that the display logic, mapping logic and mapping control are moved from the layer storage and into the display computing appliance but the layer edit logic with synchronization remains in the layer storage.

The synchronization logic can operate in different synchronization modes. There are 3 illustrated modes: one is a change sync mode, which allows all the changes made to the respective Layer Data in a respective Data Layer responsive to a respective user's edits, to be communicated to all layer storage locations that are storing the same layer regardless of user. In the full sync layer mode, all Layer Data in a respective Data Layer is communicated to all layer storage locations that are storing the same layer regardless of user. This mode is usually used only infrequently and at one location. There are times when the synchronization fails due to network failures, some layer storage not being available during operation and other failures. In this case, the best copy of the layer storage needs to be communicated with the layer storage that is not synchronized with the other layer storage, i.e., the layer storage is not an exact duplicate and the synchronization logic has lost track of what to do. This mode restores the synchronization and then the mode can be returned to the normal state of Change Sync Mode. The Full Sync Mode requires significant bandwidth to communicate all Layer Data to all the duplicate copies and is generally impractical to always perform so is only done when necessary. The last mode is the No Sync Mode which turns off the synchronization for a particular layer storage location. This could be used for a graceful way to remove layer storage from the system or to make changes offline and then implement them quickly by making changes to this layer storage then changing the mode to Full Sync Mode, and finally back to Change Sync Mode. Each layer storage location and Data Layer stored in said location can be set to one of these modes independently. However usually all are set to Change Sync Mode.

FIG. 22 illustrates an alternate embodiment of the present invention, showing a system similar to FIG. 18, but with the addition of synchronization that involves signals which, similar to FIG. 21, maintains the data integrity across the distributed Network Layer Storage elements as in FIG. 18. Signals 2211, 2231, 2232, 2233, 2241, 2242, 2222, 2261, 2262, 2201 in FIG. 22 are similar to 1811, 1831, 1832, 1833, 1835, 1836, 1822, 1861, 1862, 1801 respectively in FIG. 18 and are discussed in detail there. Signals 2291, 2292, 2293, 2294, 2234 and 2237 in FIG. 22 are similar to signals 2191, 2192, 2193, 2194, 2134 and 2137 respectively in FIG. 21.

FIG. 23 illustrates an embodiment of the present invention wherein simultaneous document collaboration, video, voice and audio communications occur in the same system. Illustrated in FIG. 23 are two multimedia collaboration systems 2300 and 2350. Contained within the multimedia collaboration systems is a display computing appliance, 2301 and 2351 respectively. The display computing appliances communicate via connection 2310. Such communication is detailed elsewhere in this document as described in FIGS. 1 through 10 and elsewhere herein. A display, 2304 and 2354 respectively, is contained in each multimedia collaboration system. The output of the display computing appliance 2301 is coupled to the display 2304 via signal 2305. Likewise, the output of the display computing appliance 2351 is coupled to the display 2354 via signal 2355. The displays provide a visual output for the user of each display computing appliance. A speaker, 2302 and 2352 respectively, a microphone, 2303 and 2353 respectively, and video camera, 2307 and 2357 respectively, are contained in each of the collaboration systems. Microphone, 2303, is cross coupled via 2306 with the speaker, 2352. Likewise, microphone, 2353, is cross coupled via 2356 with the speaker, 2302. This system of speakers and microphones allows the users of the collaboration systems to carry on an voice conversation while using the display computing appliances 2301 and 2351. Video camera 2307 is coupled to the display 2354 via signal 2308. Video camera 2357 is coupled to the display 2304 via signal 2358. The display, 2304, will simultaneously provide a video output from signals 2305 and 2358. Likewise, the display, 2354, will simultaneously provide a video output from signals 2355 and 2308. The video along with the voice provides for a simultaneous video conferencing ability along with the display computing appliance's document collaboration.

This illustration shows both voice and video used simultaneously with the display computing appliances. However, only the voice or the video could be used with the display computing appliance. The connections 2306, 2356, 2308, 2358 and 2310 can be separate physical connections or can be combined in a single, fewer, or networking type physical network connections. The signals 2306, 2356, 2308 and 2358 can be analog or digital in nature. Other multimedia collaboration systems can be added with voice and video capabilities. In cases of 3 or more multimedia collaboration systems, the microphone and camera signals, similar to 2306 and 2308, can be optionally coupled to the display and speakers of one or a plurality of other multimedia collaboration systems providing video conferencing capabilities for more the one user. In addition, the source for the audio could be provided by another source other than a microphone such as a digital audio file, video file, tape recorder, MIDI file or other audio source. Likewise, the video does not need to be supplied by a video camera and could be provided by a digital video file, video tape, or other video source.

Figure 24:
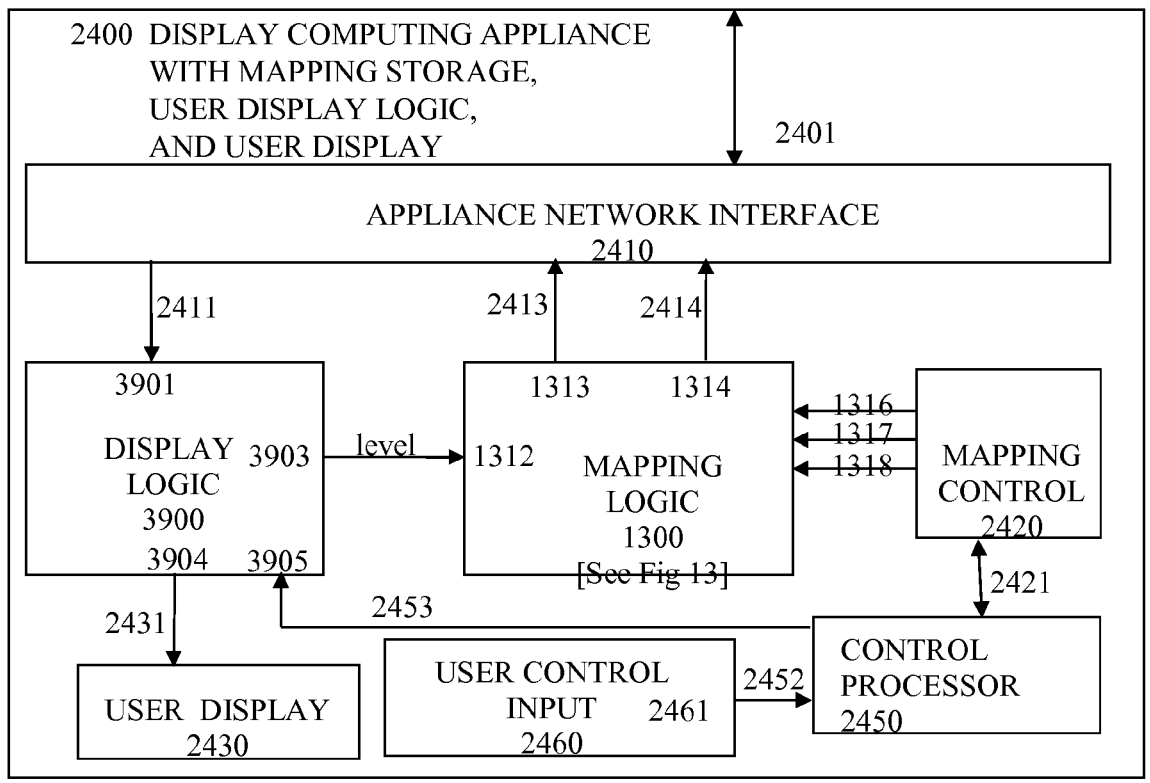
FIG. 24 illustrates an embodiment of the display-computing appliance with mapping storage, user display logic and a user display.

FIG. 24 illustrates another embodiment of the present invention, showing a system comprising a display computing appliance with Mapping Logic, an appliance network interface, user display logic, Control Processor, and a user display, (also referred to as a user appliance). This user appliance accesses the network storage through the appliance network interface, 2410, which is coupled with the appliance data network, 2401, that is coupled to network layer storage, 1900. (See FIGS. 3, 4 and 19) The Mapping Control, 2420, is coupled responsive to the Control Processor, 2450, via 2421, which is used to control the operation of the user appliance by defining the Data Layers and parts used to make up the display to the user. The Mapping Logic, 1300, is responsive to and modified by mapping control, 2420, coupled via level 1316, data layer 1317 and part 1318. The mapping control sets the level and can obtain the value of the data layer and part which would then be reported back to the control processor. Also the mapping control can set the level and set the value of the data layer and part obtained from the control processor. The display logic, 3900, is responsive to the Control Processor, 2450, for setup. The portion of Layer Data is responsive to a the Mapping Logic, 1300, which in turn is responsive to the display logic, 3900, via level, 3903, coupled to 1312. The Mapping Logic, 1300, is responsive to level on 1312, and outputs a Layer Data pointer, 1313, and part, 1314, which is coupled to layer storage via the appliance network interface, 2410, and the connected Appliance Data Network connector, 2401. The display logic is also responsive to portion of Layer Data from layer storage coupled by the connected Appliance Data Network connector, 2401, appliance network interface, 2410, and data path 3901. In this manner the display logic changes the level, 3903, and obtains layer data on 3901 which is used to build a display presentation for output on 3904. The display presentation, 3904, is coupled via 2431 to the user display, 2430. The user control input, 2460, provides input via mouse, keyboard, touchscreen, voice recognition, video recognition and other devices to provide user control of the operation of the system. The user input is coupled to the control processor, 2450, via 2452.

Figure 25:
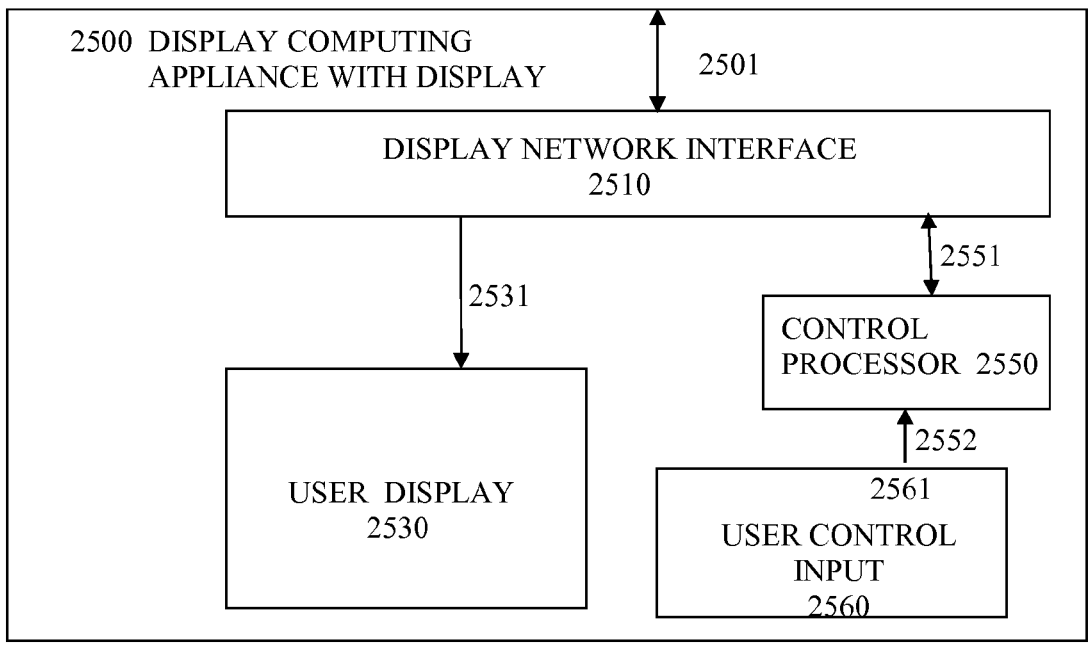
FIG. 25 illustrates a display-computing appliance with display, where the user appliance has an interface to access network storage that's stored elsewhere, and a user display.

FIG. 25 illustrates another embodiment of the present invention, showing a system comprising a display computing appliance with display, 2530, Control Processor, 2550, and an interface, 2510, (also referred to as a basic user appliance) to access network storage, Mapping Logic, display logic and mapping control via the connected Appliance Data Network. This particular embodiment requires that the network storage also provide logic to provide an output defining a combined display of various Data Layers for a local display on a respective basic user appliance for a particular respective user. The User display receives a display presentation from the display network interface, 2510, coupled by 2531. The display network interface receives the display presentation from the coupled appliance network 2501 which is coupled to network layer storage, 1500 (see FIGS. 1, 2 and 15.) The user control input, 2560, provides input via mouse, keyboard, touchscreen, voice recognition, video recognition and other devices to provide user control of the operation of the system. The user input is coupled to the control processor, 2550, via 2552. The control processor is coupled with other control processors in the system (see FIGS. 1 and 2) via signal 2551 coupled with the display network interface, 2510, and the appliance data network, 2501. The control processor is also coupled with network layer storage, 1500, in the system (see FIGS. 1, 2 and 15) via signal 2551 coupled with the display network interface, 2510, and the appliance data network, 2501.

Figure 26:
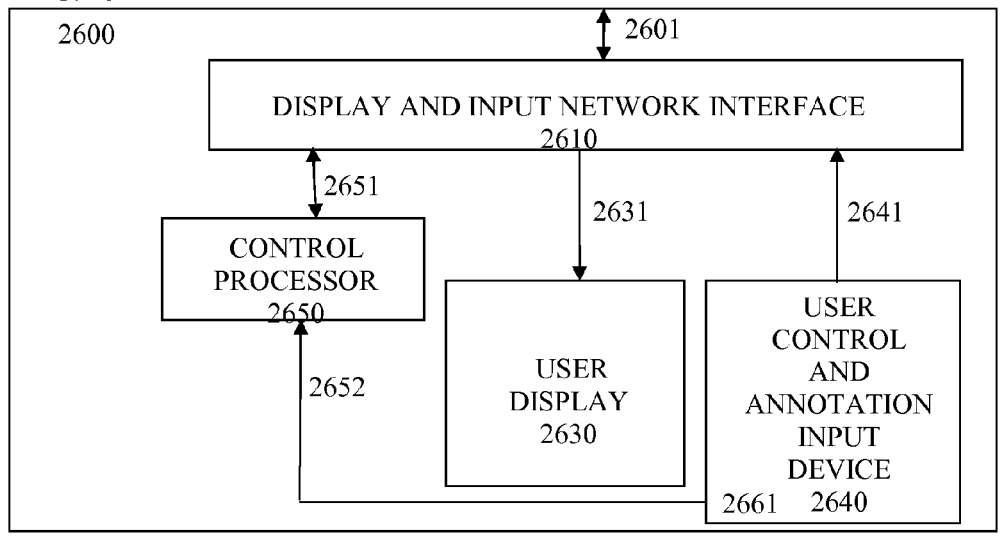
FIG. 26 illustrates an embodiment of a display computing appliance with display and input device, similar to FIG. 25, but with the addition of an input user device at the user display computing appliance which is used, inter alia, to communicate with the network storage to provide changes to the Network Data Layer.

FIG. 26 illustrates an alternate embodiment of the present invention, showing a display-computing appliance with display, 2630, Control Processor, 2650, and input device, 2640. This is similar to FIG. 25 with the addition of an user input device at the user display-computing appliance which user input device is used to communicate with the network storage to provide communication of changes to respective Layer Data in a respective Data Layer in the network storage. The signals 2652, 2651, 2631 and 2601 are similar to 2552, 2551, 2531 and 2501 respectively in FIG. 25 and are described in detail therein. FIG. 26 uses network layer storage, 1800 or 2200 (see FIG. 18 or 22 instead of 15). display computing appliance, 2600, is included in embodiments illustrated in FIGS. 5, 6 and 7 instead of FIGS. 1 and 2. There is an additional coupling from the user control and annotation input device, 2640, via 2641 to the display and input network interface, 2610. User supplied changes for the document are sent on this path and then are coupled via the appliance data network, 2601, to the layer edit logic in network layer storage, 1800 or 2200 (see FIGS. 5, 6, 7, 18 and 22). The user input device provides an interface between the user and the system to provide data of various types for changes to Layer Data. Textual data can be provided with a physical keyboard, virtual keyboard on a touch screen, virtual keyboard using a mouse, mouse gestures, camera gesture recognition, voice recognition, import from a file or network data transfer and other means. Images are provided by mouse, touchscreen input, stylus and digitizer input, camera, and import of images from a file or network data transfer in the form bitmap images such as JPEG, TIFF, PNG, GIF and many other formats, vector drawings, 2D and 3D models and other means. Video is provided by camera, and import of video from a file or network data transfer in the form of a sequence of images or computer simulations such as AVI, MPG, FLV, M1V, M4P, MOV, MPEG, OGG, VOB, WMV, DirectX, OpenGL, many other formats and other means. Audio is provided by microphone, and import of video from a file, CD, DVD, iPod, MP3 player, cell phone or network data transfer in the forms such as WAV, WMA, AIFF, the audio portion of aforementioned video, many other formats and other means.

Figure 27:
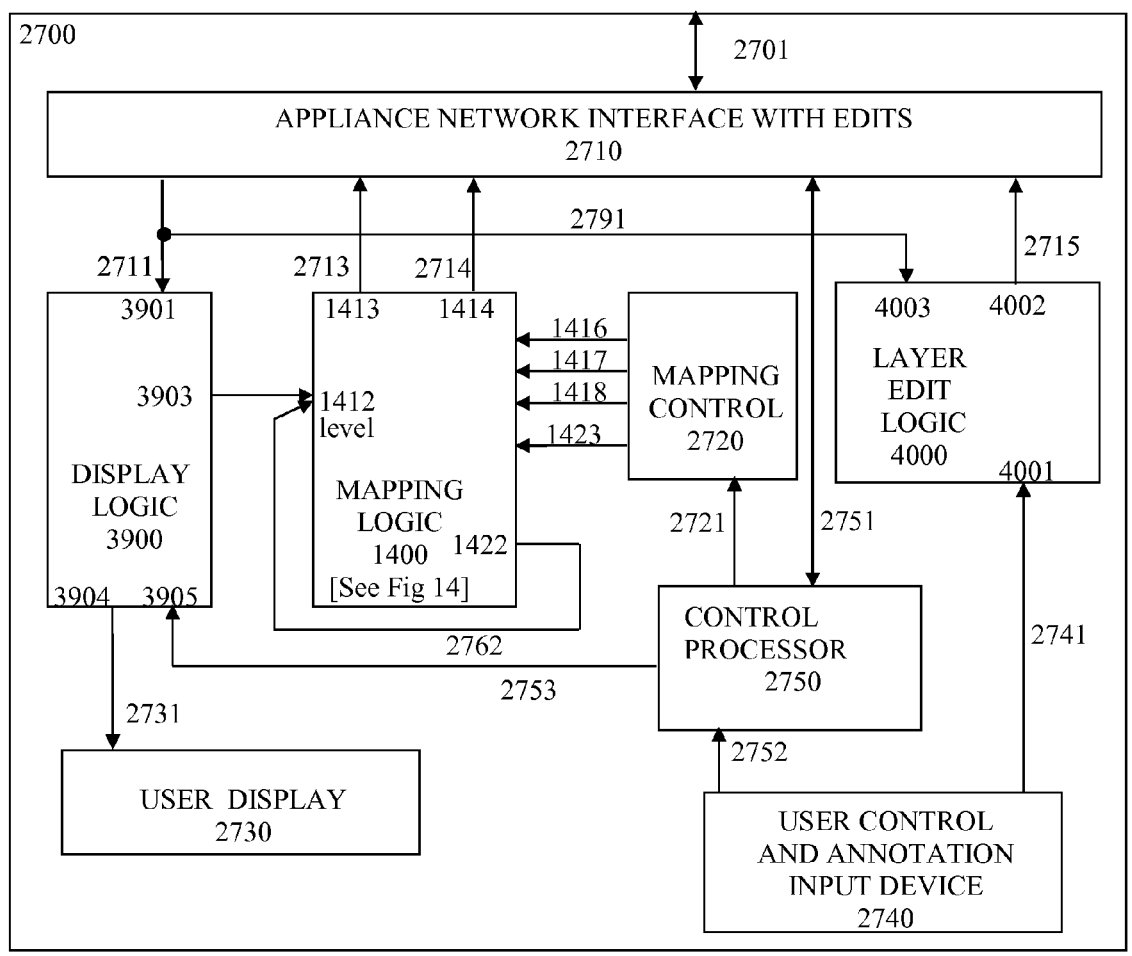
FIG. 27 illustrates an embodiment of a display computing appliance with mapping storage, user display logic, user display and user layer editing logic, similar to FIG. 24 with the addition of a user input device and Layer Edit Logic, inter alia, to allow the display computing appliance to make changes to the Layer Data in network storage that's stored elsewhere.

FIG. 27 illustrates another embodiment of the present inventions, showing a display-computing appliance with Mapping Logic, 1400, mapping control, 2720, user display logic, 3900, Control Processor, 2750, user display, 2730, user input device, 2740, and Layer Edit Logic, 4000, for a respective user. This embodiment is similar to FIG. 24 with the addition of a user input device and Layer Edit Logic to allow a user of the display-computing appliance to make changes to the Layer Data that is communicated to the layer storage. This embodiment also contains Mapping Logic utilized for that respective user and the display logic for that respective user, and the user display device to provide a presentation responsive to the display logic. The synchronization for the system is performed in the network layer storage with edits and synchronization, 2100. See FIGS. 9 and 21 for the rest of the system. The user control and annotation input device, 2740, is coupled with the control processor, 2750, via 2752 to all the user to control various aspects of the system. The user control and annotation input device is also coupled via 2741 to the layer edit logic, 4000, to provide user changes to the document presented on the user display, 2730. The layer edit logic uses the current layer data, on 4003, which is coupled via 2791 to the appliance network interface with edits. The current layer data is obtained when accessing layer data for the display presentation, detailed later. The layer edit logic combines the user changes to the document with the current layer data and outputs the change data on 4002 and sends it via coupling 2715 to the appliance network interface with edits, 2710. The appliance network interface with edits in turn sends the change data to the network layer storage with edits and synchronization, 2100 (see FIGS. 9 and 21) to change the layer data that is stored. The control processor is responsive to other control processors in the system and the global control processor, 990, via the coupling of the control processor to the appliance network interface with edits, 2710, via 2751 and the appliance data network, 2701. The mapping control 2720 is responsive to setups from the control processor, 2750, via 2721. The display logic 3900 is responsive to setups from the control processor via 2753. The mapping logic, 1400, is responsive to the mapping control, 2720, via 1416, 1417, 1418, 1423 as described in FIG. 14. The mapping logic uses the output from 1422 coupled to the level, 1412, to look up the data layer, 1413, and part, 1414, when user changes to the document are being processed in layer edit logic, 4000, so the current layer data is available on 2791 for editing. The display logic, 3900, also sets the level, 3903, for creating the display presentation. The mapping logic uses this output from 3903 coupled to the level, 1412, to look up the data layer, 1413, and part, 1414. The data layer is coupled by 2713 to the appliance network interface with edits, 2710, to the appliance data network, 2701, which is coupled to 1702 in the network layer storage, 1800 (see FIGS. 9 and 18). Likewise, part is coupled by 2714 to the appliance network interface with edits, 2710, to the appliance data network, 2701, which is coupled to 1703 in the network layer storage, 1800. If there are multiple network layer storage instances such as 940, 950, 960 shown in FIG. 9, then the control processor and appliance network interface with edits determine which of the instances to communicate with on the appliance data network. The requested layer data responsive to data layer and part is output on 1701 in the selected network layer storage, 2100. The layer data is coupled to the appliance data network, 2701 and the appliance network with edits, 2710, couples the layer data to 3901 via 2711 for the display or 4003 via 2791 for edits. The display logic combines the layer data for each level and outputs the display presentation on 3904. The display presentation is coupled to the user display, 2730, via 2731.

FIG. 28 illustrates an alternate embodiment of a display-computing appliance with Mapping Logic, 1400, mapping control, 2820, user display logic, 3900, user display, 2830, user Layer Edit Logic with synchronization, 4100. This embodiment is similar to FIG. 27, with the addition of synchronization as in FIG. 22. The signals 2892, 2893 and 2894 in FIG. 28 are similar to signals 2292, 2293 and 2294 are used for synchronization as described in FIG. 22. The signals 2841, 2852, 2851, 2853, 2862, 2831, 2811, 2813, 2814, 1416, 1417, 1418, 1423 and 2801 in FIG. 28 are similar signals 2741, 2752, 2751, 2753, 2762, 2731, 2711, 2713, 2714, 1416, 1417, 1418, 1423 and 2701 respectively in FIG. 27. This embodiment is used when synchronization is not part of the network data storage, but is instead distributed and contained in every user appliance. It is then the responsibility of each user appliance to communicate changes to all other locations (e.g., other user appliances) of Network Layer Storage to make changes to a respective particular layer if that respective particular layer is it stored in multiple locations.

FIG. 29 illustrates an example of a setup of the Mapping Logic as embodied in Mapping Logic, 1400, as illustrated in FIG. 14 for a music team where the Mapping Logic is distributed in each display computing appliance. This example has two display computing appliances, leader 1 and leader 2, in the leader role and two display computing appliances, member 3 and member 4, in the member role. All the Control Processors on the team of display computing appliances are responsive to a Control Processor in display computing appliance that is assigned a leader role. The Control Processors add the Data Layer of the leader display computing appliance that is being edited to their mapping control to be displayed. Thus a leader always has their layer displayed on all appliances in the team. This example has two leaders so both are displayed. Leader 1 is displaying a common layer, optional 2 layer, optional 1 layer, leader 2 layer and leader 1 layer. The leader 1 layer is being edited by leader 1 because the edit level is set to 4 and the leader 1 layer is level 4 in the mapping table. The user of leader 1 does not see the optional 3 layer, member 3 layer or member 4 layer because they are not in the mapping table. Leader 2 is displaying a common layer, leader 1 layer and leader 2 layer. The leader 2 layer is being edited by leader 2 because the edit level is set to 2 and the leader 2 layer is level 2 in the mapping table. The user of leader 2 does not see the optional 1, optional 2, optional 3 layer, member 3 layer or member 4 layer because they are not in the mapping table. Member 3 is displaying a common layer, optional 3 layer, leader 2 layer, leader 1 layer and member 3 layer. The member 3 layer is being edited by member 3 because the edit level is set to 4 and the member 3 layer is level 4 in the mapping table. The user of member 3 does not see the optional 1 layer, optional 2 layer, or member 4 layer because they are not in the mapping table. Member 4 is displaying a common layer, leader 2 layer, leader 1 layer and member 4 layer. The member 4 layer is being edited by member 4 because the edit level is set to 3 and the member 4 layer is level 3 in the mapping table. The user of member 4 does not see the optional 1 layer, optional 2 layer, optional 3 layer, or member 3 layer because they are not in the mapping table. This example show the flexibility of the display options for each display computing appliance in the system. The roles of each display computing appliance define the operations of the Control Processors which can quickly quickly change the Mapping Logic to provide dynamic display options for the users. The example in FIGS. 29, 32 and 37 can also be applied to the embodiment of the Mapping Logic 1100, 1200 and 1300. The setup for Mapping Logic, 1300, is identical to Mapping Logic, 1400, except that the edit level is not included. Mapping Logic 1100 and 1200 are similar to 1400 and 1300 respectively except that all the mapping tables are combined into one table that contains another column for the user. Similarly, the edit levels are combined into one table with another column for the user. Examples of a setup are provided with each of the respective Mapping Logic elements, 1100, 1200, 1300 and 1400. The synchronization mode for teacher layer and all student layers is normally the change sync mode. A teacher can initiate a synchronization mode of full sync mode for the teacher layer. A teacher can initiate a synchronization mode of full sync for one or a plurality of student layers.

Figure 30:
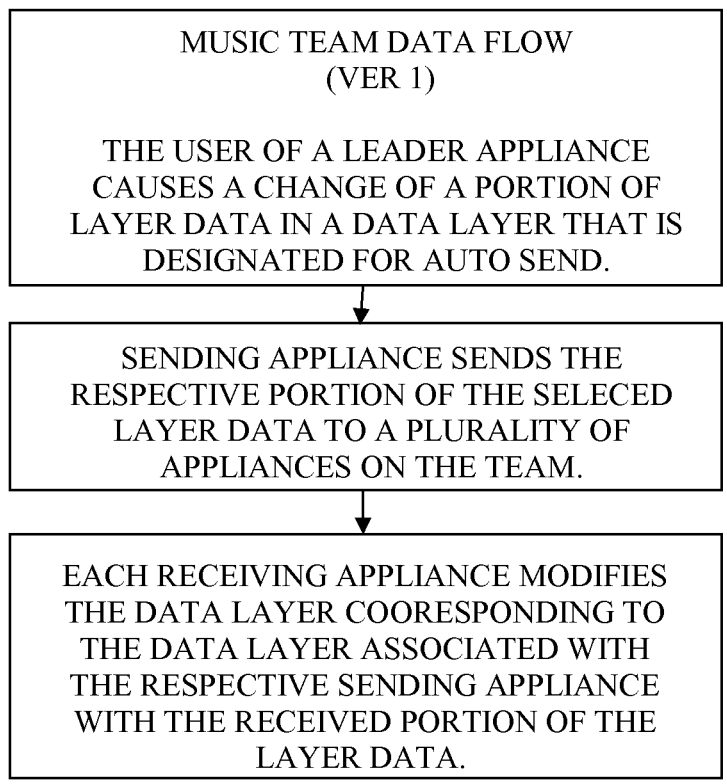
FIG. 30 illustrates a first method of data flow for a music team.

FIG. 30 illustrates the music team data flow for a the first embodiment. Some team roles allow a portion of Layer Data to be sent from its original Data Layer to a different Data Layer. This flow diagram illustrates the steps for a system as illustrated in FIG. 9. This embodiment describes the receiving appliance making the determination of which Data Layer to put the portion of Layer Data.

Figure 31:
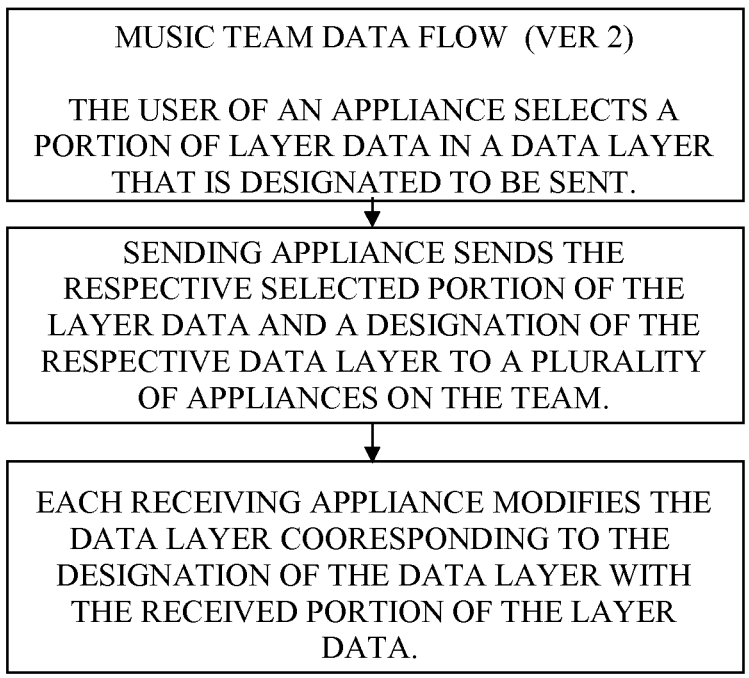
FIG. 31 illustrates a second method of data flow for a music team.

FIG. 31 illustrates the music team data flow in a second embodiment of that workflow. This flow diagram illustrates the steps for a system as illustrated in FIG. 9. This embodiment describes the sending appliance making the determination of which Data Layer to put the portion of Layer Data.

Figure 60:
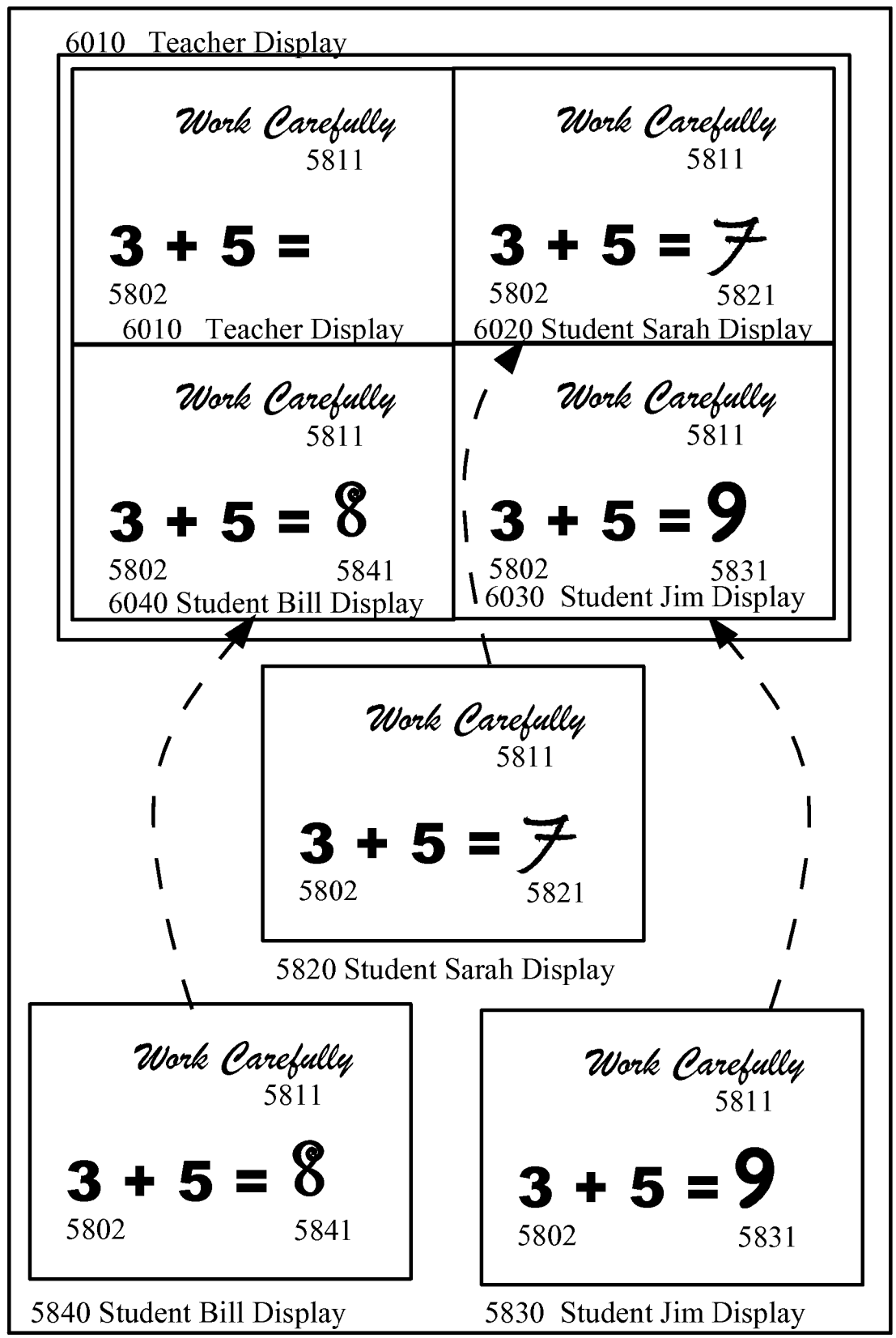
FIG. 60 illustrates an education team with one teacher and three students where the teacher is monitoring the entire classroom's progress.

FIG. 32 illustrates an example of a setup of the Mapping Logic as embodied in Mapping Logic, 1400, as illustrated in FIG. 14 for an education team where the Mapping Logic is distributed in each display computing appliance. This example has one display computing appliance, teacher, in the teacher role and a plurality of display computing appliances, student 1, student 2, student 3, . . . , in the student role. All the Control Processors on the team of display computing appliances are responsive to a Control Processor in display computing appliance that is assigned a teacher role. The Control Processors add the Data Layer of the teacher that is being edited to their mapping control to be displayed. Thus a teacher always has their layer displayed on all appliances in the team. This example has one teacher but multiple teachers are allowed, however all teachers share the same Teacher Data Layer. This example illustrates the entire class viewing the same part, lesson 6 but this does not have to be the case. However, the teacher's Control Processor may communicate with the student Control Processors and prohibit the students from changing the part being viewed, or alternatively allow one or all the students change the part, e.g., move on to lesson 7. A student always shows 3 Data Layers, the Common Data Layer, the Teacher Data Layer and the student's own Data Layer as illustrated in the example setup "Student Y Mapping Logic". The student always edits their own Data Layer but the Teacher Data Layer is always included on the display. .A teacher has three difference modes for display: teacher mode, multi-mode and teacher-student mode. The teacher mode displays 2 Data Layers, the Teacher Data Layer and Common Data Layer as illustrated in the example setup "Teacher Mapping Logic in Teacher Mode". The teacher edits the Teacher Data Layer (multiple teacher appliances would edit the same Data Layer) and since the students are viewing this Data Layer they receive the edits as well but can't modify them. The multi-mode displays the Teacher Data Layer and all the Student Data Layers as shown in FIG. 60. The teacher display logic operates in a multi-view mode. The common layer, level=0, is reduced in size and duplicated combined for the display multiple times. Then every other layer is reduced in size and placed over one of the copies of theCommon Data Layer. The resulting display provides an overview of everyone in the class. The example of the Mapping Logic setup is shown in "Teacher Mapping Logic in Multi-Mode". Alternative embodiments would allow the Mapping Logic to include the Common Data Layer with different parts to correspond to the parts that are currently being used by each student. The student layer would then have a part corresponding to the current student's part. This is accomplished with communication between the Control Processors. The teacher-student mode is identical to the mapping for a specific student. This allows the teacher to modify that Student's Data Layer and work one-on-one with the student to correct their mistakes or give private comments as shown in the section "Teacher Mapping Logic in Student Mode for Student X". Since the teacher is modifying the student's layer the student can make changes to the teacher's comments. An alternative embodiment would create another Data Layer for each student for the teacher to edit and visible only on the respective student's appliance. This would allow the teacher to make private edits on for a student but not allow the student to edit them. The synchronization mode for teacher layer and all student layers is normally the change sync mode. A teacher can initiate a synchronization mode of full sync mode for the teacher layer. A teacher can initiate a synchronization mode of full sync for one or a plurality of student layers.

FIG. 33 illustrates the team data flow for an education team, for a student, for a first embodiment. This flow diagram illustrates the steps for a system as illustrated in FIG. 9. This embodiment describes the receiving teacher appliance of student portion of Layer Data making the determination of which Data Layer to put the portion of Layer Data.

FIG. 34 illustrates an alternative data flow for an education team, for the student. This flow diagram illustrates the steps for a system as illustrated in FIG. 9. This embodiment describes the sending student appliance of student portion of Layer Data making the determination of which Data Layer to put the portion of Layer Data.

FIG. 35 illustrates the team data flow for an education team, for a teacher. This flow diagram illustrates the steps for a system as illustrated in FIG. 9. This embodiment describes the receiving appliance of teacher portion of Layer Data making the determination of which Data Layer to put the portion of Layer Data.

FIG. 36 illustrates the education team data flow for student layer edits made by the teacher. This flow diagram illustrates the steps for a system as illustrated in FIG. 9. This embodiment describes the sending teacher appliance of teacher portion of Layer Data making the determination of which Data Layer to put the portion of Layer Data.

FIG. 37 illustrates an example of a setup of the Mapping Logic as embodied in Mapping Logic, 1400, as illustrated in FIG. 14 for an ad hoc team where the Mapping Logic is distributed in each display computing appliance. This example has a plurality of display computing appliances, member 1, member 2, member 3, . . . , in the ad hoc role. The ad hoc role does not put many limits on each appliance. Each appliance is allowed to select whatever Data Layers they choose to display and what ever part to choose. In this example, member 1 is displaying page 7 of the Common Data Layer, notes 1 Data Layer and member 1 Data Layer. Member 1 is editing their own Data Layer, member 1. Member 2 is displaying page 8 of the Common Data Layer, member 1 Data Layer and member 2 Data Layer. Member 2 is editing member 1's Data Layer, not their own. Note that member 2 is editing a portion of the Data Layers that neither member 1 or 3 are currently viewing, however, if member 1 or 3 changes their part to page 8 they would obtain the changes being made by member 2. Member 3 is displaying page 7 of the Common Data Layer and member 1 Data Layer. It is not editing any layer and just monitoring member 1's activities. The Control Processor of each appliance could change the Mapping Logic responsive to user input. Alternative embodiments would allow the Control Processors to communicate and prohibit some settings, e.g., an appliance could prohibit viewing or editing of their Data Layer.

FIG. 38 illustrates data flow of user-to-user edits in an Ad Hoc team. The flow chart illustrates to steps that the user and Display Computing Appliances follow to share edits. Initially, the user on the sending appliances selects a portion of the layer data in a data layer. They the user selects appliances that the should receive the selected layer data. The layer data is sent to those appliances. The receiving appliances do not store the received layer data in the same data layer. They store a copy of the layer data in the data layer that the receiving appliances has marked for edit. The sending and receiving appliances thus copy layer data from one data layer to a different data layer. Each appliance then has an unique combination of layer data from other appliances and the layer data generated on their own respective appliance. Once copied into the edit data layer of the appliance, each appliance can selectively send it to another appliance, remove or modify the layer data.

FIG. 39 illustrates another embodiment of display logic. This display logic has Layer Data Combined Storage, 3920, for combined Layer Data, a Display Logic Controller, 3930, and a logic means, Layer Data Combine, 3910, to combine layer data from Data Layers for multiple Data Layers, and a connection, 3904, to send the result to the display for presentation. The Display Logic Controller, 3930, receives a display setup, 3905, from the Control Processor, e.g., the user to display. It then outputs the user on 3902 and successive levels, 3903, starting with 0 to the Mapping Logic. The layer storage is responsive to the Mapping Logic and provides a portion of layer data, 3901. The Display Logic Controller senses when no portion of layer data is available to stop the process and indicate via connection, 3931, to the Layer Data Combined Storage, 3920, to output the result on display out, 3904. When a valid portion of layer data is present on 3901, the Display Logic Controller, 3930, indicates via 3932 to the Layer Data Combine, 3910, to combine in a specified way the portion of layer data with the current Layer Data Combined Storage, 3920, via 3912. The Layer Data Combine, 3910, outputs the combination result on 3911 and the Layer Data Combined Storage, 3920, is instructed by the Display Logic Controller, 3930, via 3931 to store this combined result.

FIG. 40 illustrates an embodiment of the Layer Edit Logic, 4000, which is responsive to Data Layer change information, 4001, that is obtained from user input. The information separation, 4010, is responsive to the Data Layer change information and provides two outputs: user to be modified, 4004, and modifications, 4011. The Mapping Logic is responsive to the user to be modified and the Layer Storage is responsive to the Mapping Logic which provides the Current Data Layer coupled via 4003. The Data Layer modifier, 4020, is responsive to both the Current Data Layer and modifications and applies the modifications to the Current Data Layer and outputs the modified Data Layer, 4002. The modified Data Layer is then coupled to the Layer Storage where it replaces the current layer data.

FIG. 41 illustrates an embodiment of Layer Edit Logic with synchronization, 4100. This is similar to the embodiment, 4000, in FIG. 40 but with the addition of synchronization of multiple copies of Data Layers. The elements 4101, 4160, 4161, 4120, 4103, 4102 are functionally equivalent to 4001, 4010, 4011, 4020, 4003, 4002 respectively. The "send changes to other Layer Storage locations", 4140, otherwise known as "send changes" is responsive to the user modifications, 4161. The layer changed, 4108, and part changed, 4109.

Signals 4108 and 4109 are active when a display computing appliance makes a change in the layer storage. 4108 and 4109 are coupled to the Mapping Logic which is responsive to the user to be modified, 4104. Send changes combines these inputs and sends it to other Layer Storage locations that have a duplicate of the layer changed via coupled by Data Layer Sync Out, 4107, which is connected Appliance Data Network. Data Layer Sync Out is received from the connected Appliance Data Network from other instances of Layer Edit Logic, 4100 on Data Layer Sync In, 4101. The user information separation, 4160, provides three outputs, layer to sync, 4105, part to sync, 4106, and user modifications, 4151. 4105 and 4106 are only output when a synchronization change occurs, when initiated by a user the user to be modified, 4104 is active. Thus the operation varies depending on the source of the change. The synchronization process bypasses the Mapping Logic because it is dependent only on the Layer Storage. The layer to sync and part to sync are sent directly to the Layer Storage which is responsive to those signals and returns the Current Data Layer, 4103. Similar to user modifications, a synchronization change is applied to the Current Data Layer, 4103, and the Data Layer Modifier, 4120, outputs a Modified Data Layer, 4102, which is used to replace the Current Data Layer in layer storage.

Figure 42:
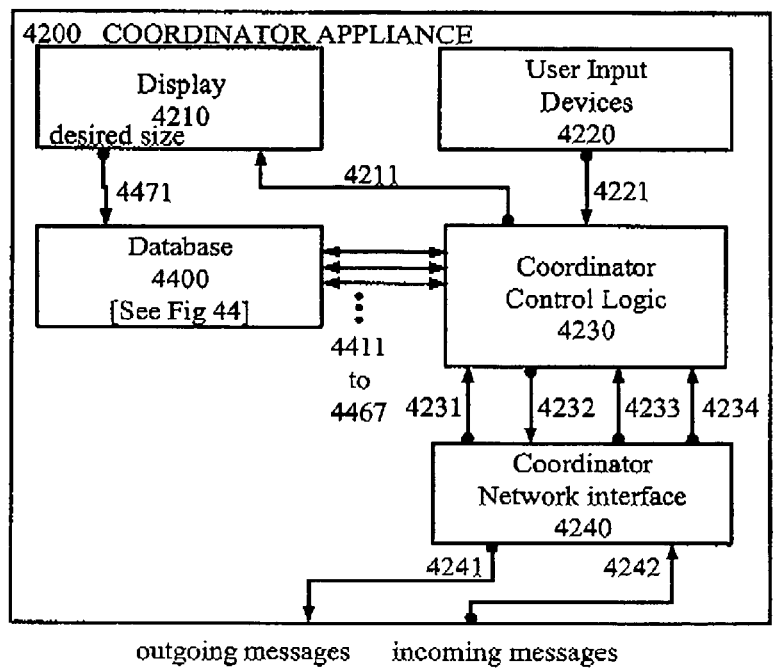
FIG. 42 illustrates an embodiment of a coordinator appliance that has coordination functions on a team.

FIG. 42 illustrates an embodiment of a coordinator appliance that provides coordination functions on a team. The illustrated embodiment of the coordinator appliance is comprised of a user input, 4220, coordinator logic, 4230, database, 4400, coordinator network interface, 4240, and a display, 4210. The user input devices, 4220, includes all the inputs used by the user of the appliance such as keyboards, mouse, touch screen, pen tablets, microphones, cameras, etc. These inputs coupled to the coordinator control logic, 4230, via 4221. The coordinator control logic evaluates this input, 4212, and messages from the network, 4231, 4233, 4234, to determine create a presentation for the display. The coordinator control logic is also responsive to the database, 4400, and the assigned role for the appliance. Coordinator appliances generally lead the team and determine which appliances are part of the team. The assigned role helps determine how to create the display presentation and what messages should be sent to other appliances via 4232. The coordinator network interface, 4240, handles the network communications and keeps track of other appliances on the network. Outgoing messages, 4241, are sent to other appliances both for identification and controlling other appliances. Incoming messages, 4242, contain both identification and control information. The database, 4400, contains information about the current state of the appliance but also the Layer Storage. The display presents information to the user. Many times this is visually on a computer screen, but may also take other forms such as sound, music, static images, movies, flash, interactive games, projectors, tactile feedback (resistance to movement in a joy stick, or vibration), motion of objects, etc.

Figure 43:
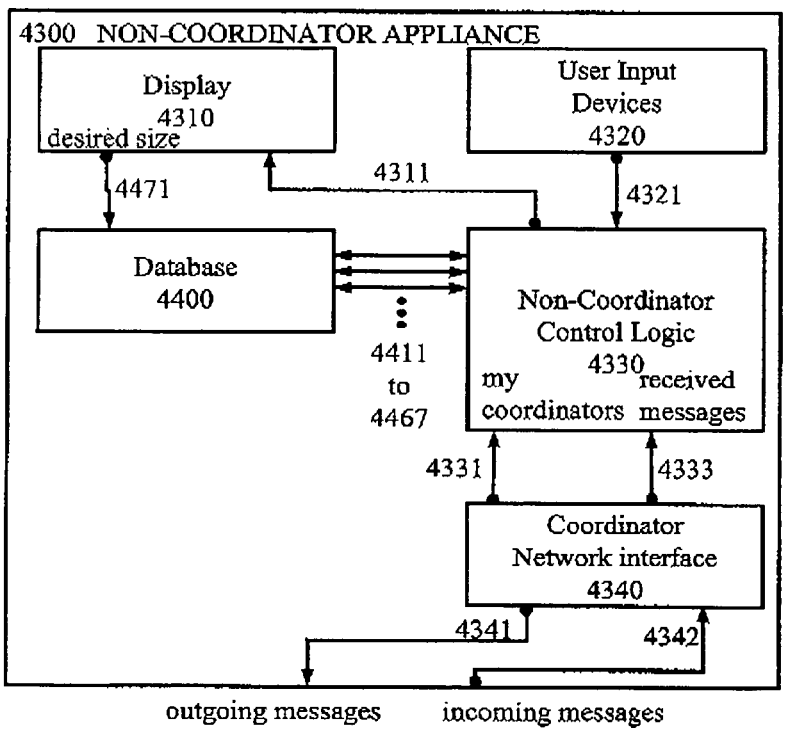
FIG. 43 illustrates a non-coordinator appliance, similar to a coordinator appliance but without coordinator control logic.

FIG. 43 illustrates an embodiment of a non-coordinator appliance. It is similar to the illustrated coordinator appliance as in FIG. 42, having a user input, but instead of having coordinator database logic and coordinator network interface and logic, the illustrated non-coordinator appliance has non-coordinator control logic. The embodiment in FIGS. 42 and 43 is that the control logic is different as to what messages are sent and not sent. A non-coordinator appliance is a member of a team but is not a leader. For example, in an educational team, the teacher role is a coordinator appliance and the student appliances are non-coordinators. The facilitator role in a meeting is the leader of a meeting team. Participants in a meeting are non-coordinators. The presenter in a meeting team is also a participant but has different functionality than a participant. However, the presenter could be assigned both the facilitator and presenter roles.

Figure 44:
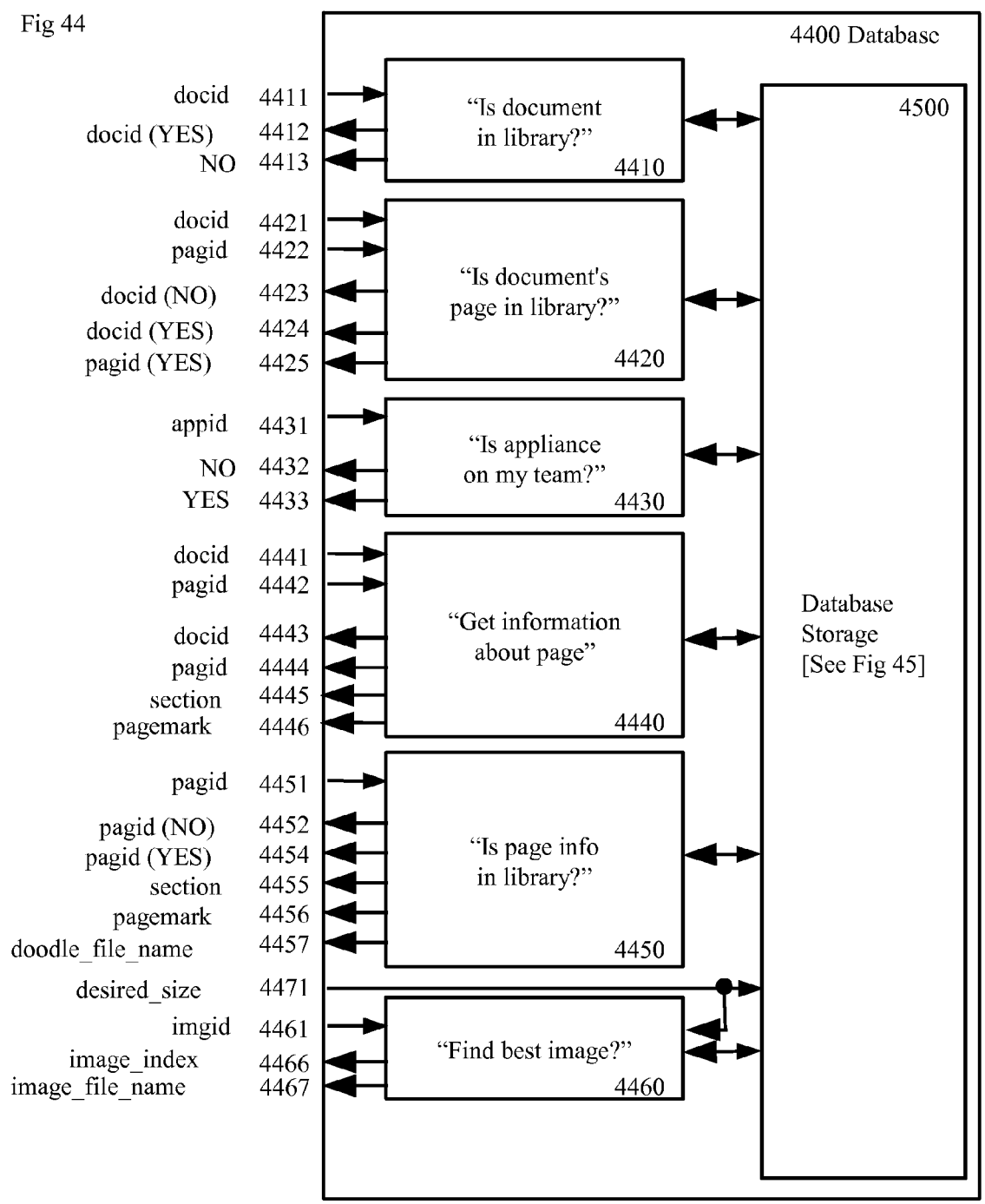
FIG. 44 illustrates a database system that provides control information and Data Layer storage.

FIG. 44 illustrates an embodiment of a database, 4400. The database has two basic parts: database storage, 4500, and information gathering functions as illustrated by 4410, 4420, 4430, 4440, 4450 and 4460. The database storage provides a structured method for storing and retrieving information. A common form of this is a relational database which provides tables of information that can be joined together to provide complex, yet efficient, searches for the stored information. However, other methods can be used which may be similar to a relational database but not meeting the standards for a relational database, such as indexed lists, b-trees, linked-lists and other methods. Some of these can provide the same information but with a significantly different structure than a relational database. In this embodiment, the docid is a unique descriptor of a unique document. The pagid is a unique descriptor of a unique page within a document (identifies part of layer data). The imgid is a unique descriptor of a unique set of images which comprises the common base layer for a page of a document (part of layer data). image index selects on the unique set of images for a imgid. Each image in the set is visually identical to the others in the set except that it is a different resolution. image file name is the file that contains the image data for a given imgid and image index. The appid is a unique descriptor of a specific appliance on the network. The section and pagemark are a user-friendly description of a specific page (pagid) in a document (docid). Doodle file name is the name of a file that contains the layer data for a specific page (pagid). The desired size is a signal responsive to the display that provides the optimum size for the display. "Is document in the library?", 4410, receives an docid on 4411, and queries the database storage, 4500, and returns a yes (and the docid), 4412, or no, 4413. "Is document's page in the library?", 4420, receives an docid, 4421, and pagid, 4422, and queries the database storage, 4500, and returns yes and the docid, 4424, and the pagid, 4425; or no and docid, 4423. "Is appliance on my team?", 4430, receives an appid, 4431, and queries the database storage, 4500, and returns yes, 4432, and no, 4433. "Get information about page", 4440, receives an docid, 4441, and pagid, 4442, and queries the database storage, 4500, and returns the docid, 4443, pagid, 4444, section, 4445, pagemark, 4446. "Is page info in library?", 4450, receives a pagid, 4451, and queries the database storage, 4500, and returns yes and pagid, 4454, no and pagid, 4452, section, 4455, pagemark, 4456, and doodle file name, 4457. "Get information about page", 4440, receives an docid, 4441, and pagid, 4442, and queries the database storage, 4500, and returns the docid, 4443, pagid, 4444, section, 4445, pagemark, 4446. "Find best image?", 4460, receives an imgid, 4461, and desired size, 4471, and queries the database storage, 4500, and returns image index, 4466, and doodle file name, 4467.

Figure 45:
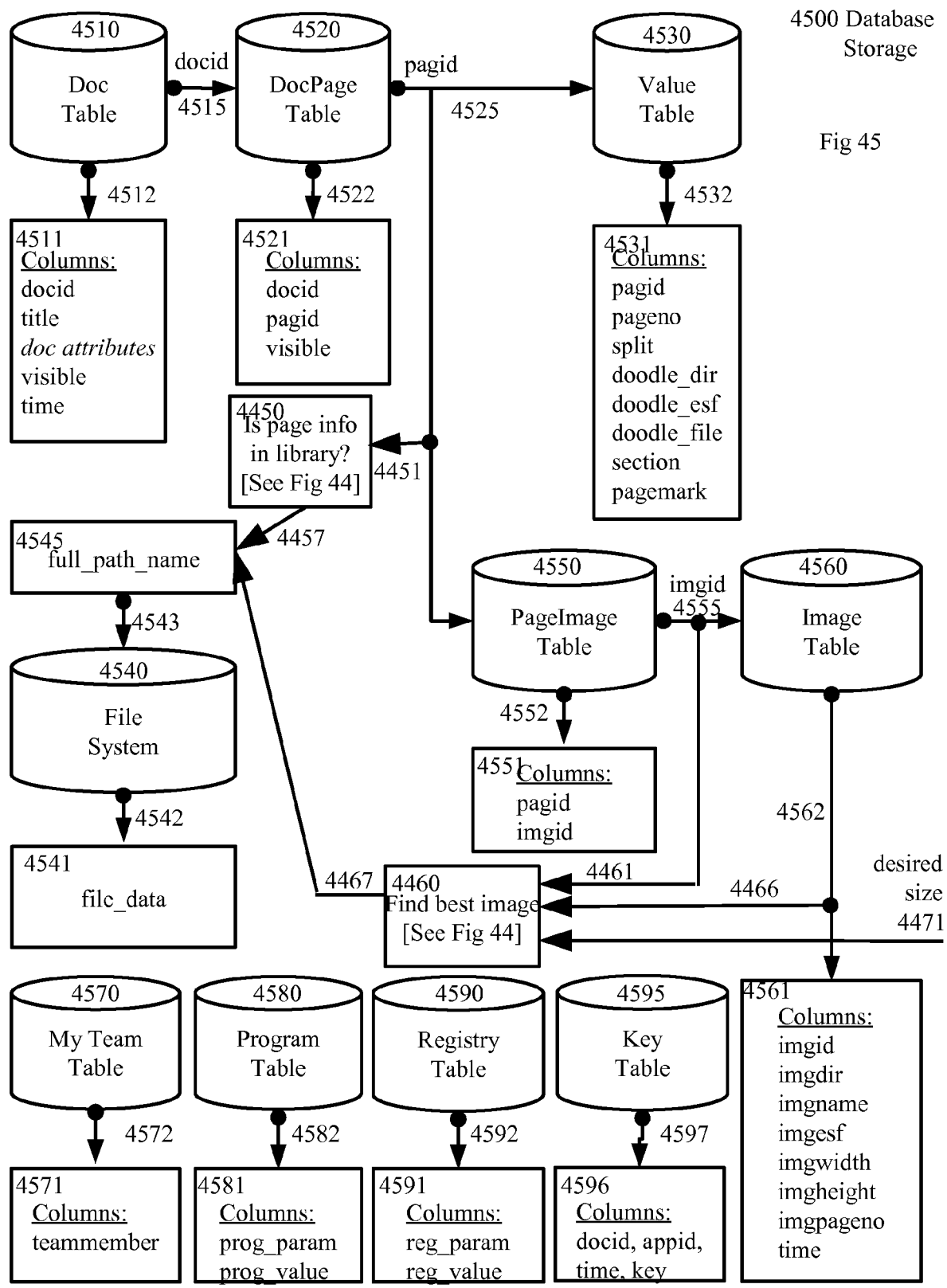
FIG. 45 illustrates the embodiment of database storage contained in the database system illustrated in FIG. 44.

FIG. 45 illustrates an alternate embodiment of Database Storage, 4500. The database storage is composed a plurality of tables and a file system, 4540, for storing large amounts of data, e.g., layer data. The tables could be implemented in a number of ways included the use of a relational database, group object structure (5300) using properties as column values, b-tree files, etc. The tables have rows and columns. The ordering of the columns is not important, but the ordering of the rows is important in some tables. In this case, some implementations will need to add a column sortable values to keep track of the preferred order. The doc table, 4510, and docpage table, 4520, need to maintain ordering of the rows and the others do not. Ordering is important in these tables because the order of the rows define the order that the user sees the documents and pages within the document. The tables are: doc table, 4510, docpag table, 4520, value table, 4530, pageimage table, 4550, image table, 4560, my team table, 4570, program table, 4580, registry table, 4590, and key table, 4595.

The tables are coupled together by common columns. When a row in one table and a row in another table have a common column and the values are the same then the other columns in each of the tables are related. This is called a join in a relational database. The doc table is coupled, 4515, to the docpage table via a common column docid. The docpage table is coupled, 4525, to the value table, 4530, and pageimage table, 4550, via a common column pagid. The pageimage table is coupled, 4555, to the image table, 4560, via the common column imgid. The rows of the doc table represent a set of documents in a particular order, much like books carefully placed in a bookshelf. The columns in the doc table, 4511, are the docid, title, visible and time.

The docid is a unique identifier of the document. The title is the title of the document. Visible determines whether the document will be shown or hidden. Time is the date the document was created. Other document attributes can also be stored in other columns. The rows of the docpage table represent a page in each document and the order of the rows put the pages in order as they are in a book. The columns are docid, pagid, and visible. There are usually many rows with the same docid, one for each page in the document but each row has a different pagid. This allows pages to be quickly reordered in using just this table. The visible column allows an individual page to be shown or hidden. The value table has the following columns: pagid, pageno, split, doodle_dir, doodle_esf, doodle_file, section and pagemark. The pagid is used to couple the rows of the docpage table and the pagid values are unique in each row of the value table. The pageno column provides a page number for the page which is used for the display for the user. The split value is provides a location on the page where it can be split between the top and bottom halves for display. The doodle_dir provides a directory in the file system, 4540, where the a plurality of Data Layer store their layer data for this page in a doodle file. The doodle_esf provides for a container file like zip that contains the doodle file. The doodle_file provides the name of the file in the file system or in the doodle_esf container. Section provides a descriptive name of this page and all pages that follow in this document until a new section is provided for the user. Pagemark provides a descriptive name of this page only for the user. The pageimage table, 4550, has two columns: pagid, imgid. The pagid values are unique in each row of the pageimage table. The imgid usually is unique but not always. This allows an image to be duplicated by using the same imgid value for two different pagid's. The image table, 4560, provides the location and attributes of the base common images used as the common layer data for the page. The columns in the image table are imgid, imgdir, imgname, imgesf, imgwidth, imgpageno, time. The imgid is a unique identifier for a set representations of a visually identical image to the user. There are multiple images stored at different resolutions but visually look the same to the user. This reduces the computations required by the appliance to resize an image to fit on a particular display, the closest best fit can be selected that has been precomputed and stored. The imgdir provides the directory in the file system where the image is located. Imgesf is the file name of a container that can hold many files like a zip file. Imgname is the file name of the image on the file system directly or the name in the imgesf if provided. imgwidth and imgheight provide the width and height of the image so the optimum image can be selected.

Since there can be multiple rows with the same value of imgid, the image index indicates which of the rows contains the selected image for a page and display. Find best image, 4460, uses the imgid, 4565, matching image table rows, 4562, and the desired size, 4471, to find the best image location, 4467. The location is combined in the full_path$_{13}$ name, 4545. The file system, 4540, is responsive to the full_path$_{13}$ name coupled by 4543 and outputs the file data, 4541, via 4542 which is the image data to be sent to the display. The "Is page info in library?", 4450, is responsive to the pagid coupled by 4525 and 4451. The output, 4457, provides information about the page including the Layer Storage except base Common Data Layer (doodle) location. The full_path$_{13}$ name, 4545 is responsive to the page information and creates a description of the location of the Layer Storage for the file system, 4540. The file system is responsive to the coupling signal 4543, and outputs via 4542 to the file_data, 4541, which is the Layer Storage except the base Common Data Layer for processing by the display logic in the coordinator control logic or non-coordinator control logic.

The my team table has one column which is teammember. This table has a list of team members on their team. This table is only present on a coordinator appliance. The program table has two columns, prog_param and grog_value. Each row of the program table has a prog_param value which defines parameter for the application. The grog_value in the same row is the value for the prog_param is the value for the parameter. These parameters are used to define a number of items for the appliance like its name, the current document and page being displayed and many other items that need to be remembered when the appliance is turned off and then back on. The registry table has two columns, reg_param and reg$_{13}$ value. It is similar to the program table but is used for installation parameters and on some cases may be stored in a different manner than the other tables. The key table has the following columns: docid, appid, time, key. This table is used to store encryption keys that some of the content may be using. The key column contains the key for a document specified by docid and for a specific appliance specified by appid. A group of documents may have been created at the same time and can have the same key so they are identified with the time column.

Figure 46:
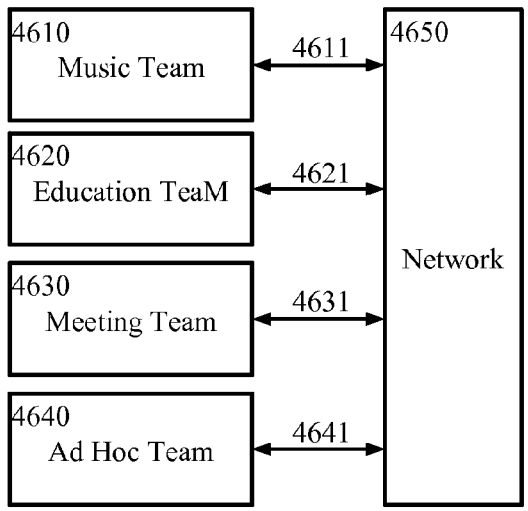
FIG. 46 illustrates an embodiment wherein multiple teams are each separately made up of multiple appliances and can each co-exist on the same network but act as independent teams, showing a music team, an education team, a meeting team and an Ad Hoc team.

FIG. 46 illustrates an alternate embodiment of the present invention, showing a system wherein multiple teams each are made up of multiple appliances, and wherein the multiple teams can co-exist on the same network, but act as independent teams. All teams communicate over a common network, 4650, and connections 4611, 4621, 4631, 4641. As illustrated in FIG. 18, there is shown a music team, 4610, an education team, 4620, a meeting team, 4630, and an Ad Hoc team, 4640. The music team is shown as optimized for people collaborating using music to rehearse, edit, and/or perform the displayed music. The education team is shown as optimized for a system operating in a classroom setting where there is a teacher and multiple students collaborating. The meeting team is sown as optimized for the use during a meeting for collaboration of multiple people, where there are multiple participants, each having an input device with one or more (some) making presentations and with each member having the ability to make their own separate input onto the team presentation. The Ad Hoc team is shown as optimized for collaboration of informal gatherings of people so that they can each communicate with their own ideas to a common display, and provides a system to facilitate those meetings. Many other teams are possible, four have been shown in this illustration.

Figure 47:
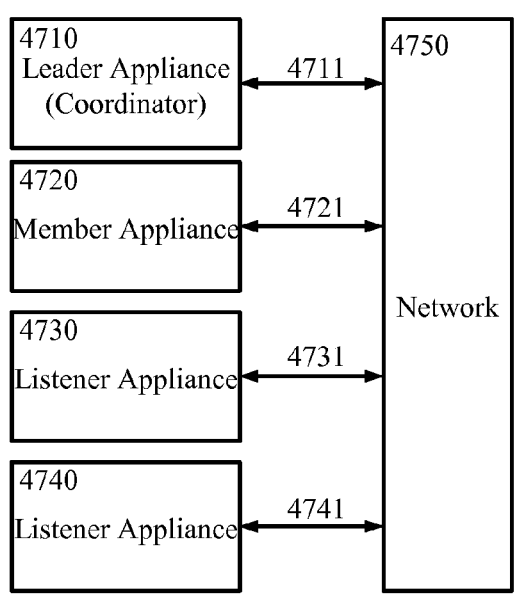

FIG. 47 illustrates roles within a music team. There are shown multiple roles and the functioning of the appliance. What layers are used by a particular appliance depends on its role. Any edits that may be made will depend on the role that an appliance is functioning in. The team communicates over a common network, 4750 and connections 4711, 4721, 4731, 4741.

In a music team, there can be a leader appliance, 4710, which is the coordinator, and the leader appliance can make changes to and communicate these changes (ranging from edits to a display document, to page jumps, to document ordering, to import or export, etc.) with all the other appliances. There may be multiple leader appliances on a team.

A member appliance, 4720, is one that generally listens to what the leader appliance is doing but may be able to have some other limited functionality (such as making local-only edits, or local-only page jumps, or local-only document order changes).

A listener appliance, 4730 and 4740, is similar to a member appliance, but it is strictly only able to listen to commands and input from the members and leaders, and cannot make any changes by itself.

Figure 48:
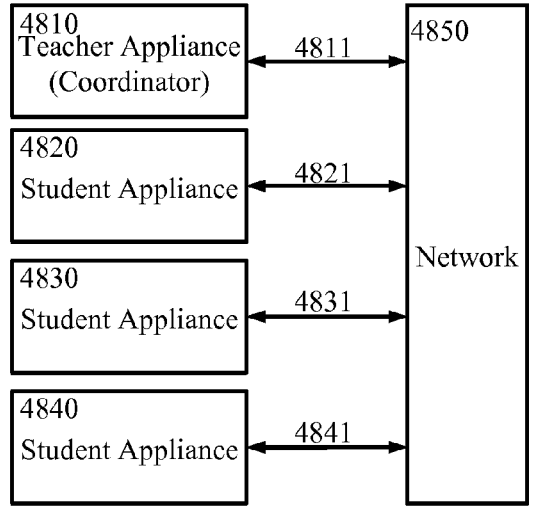
FIG. 48 illustrates roles in an education team, showing the case where there are two different roles: the teacher and the student.

FIG. 48 illustrates roles in an education team. In the illustrated embodiment, there are two different roles: the teacher and the student. The team communicates over a common network, 4850 and connections 4811, 4821, 4831, 4841. As illustrated, the teacher, 4810, (or all teachers on a team) has the ability to communicate with all the students, 4820, 4830 and 4840, as well as with any other teacher on a same team that may be on the team and can selectively choose for communication with and to students as either to the entire class or to an individual selected student. The teacher appliance can also select to view in real-time all of the students' appliances' displays at once in a multi-screen mode. As illustrated, the student appliance communicates only with the teacher (or teachers, but not with other students) so that the teacher is aware of what the student is doing and themselves. The student is not able to communicate with other students.

Figure 49:
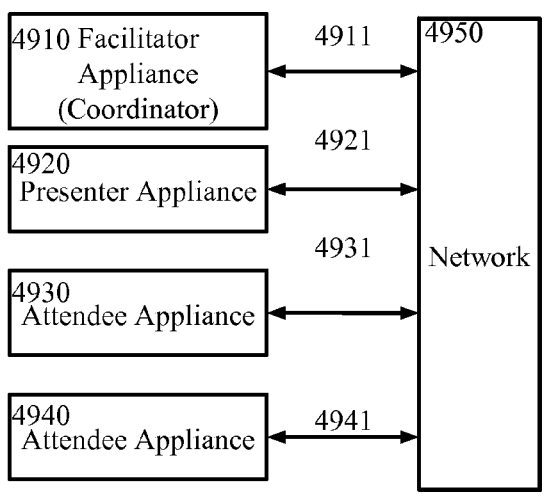
FIG. 49 shows appliance roles in a meeting team, showing the case where there are three different roles, which can change during the course of a meeting, the three roles being facilitator, presenter and attendee.

FIG. 49 shows an embodiment of appliance roles in a meeting team. The team communicates over a common network, 4950 and connections 4911, 4921, 4931, 4941. As illustrated, three are different roles. The roles of a particular appliance can change during the course of a meeting. The three illustrated roles are facilitator, presenter and attendee. The facilitator, 4910, is the appliance that determines which appliances are allowed to be at and in the meeting and determines and decides which appliances are permitted to be a presenter and which appliances are an attendee, 4930 and 4940. The presenter, 4920, is allowed to have his/her edits sent from his/her appliance to the appliances of other members of the team. The presenter can selectively control which page the respective users at each appliance in meeting is looking at. The facilitator can selectively change which appliance is the presenter. Individual attendees have more limited control. At the discretion of the facilitator appliance, an attendee appliance may or may not be permitted to communicate with other appliances. A meeting can have different presenters at different times. The facilitator an change who (which appliance) is enabled as a presenter. Usually there are multiple attendees and one presenter, however there are cases when multiple presenters are desired. Multiple presenters can be confusing to the attendees in a meeting but there are times when two or more people are mutually presenting. In extreme cases, everyone could be assigned the presenter role. There can be times when there is no presenter, such as times in between different presenters or during breaks. A presenter and facilitator has all the functionality of an attendee.

Figure 50:
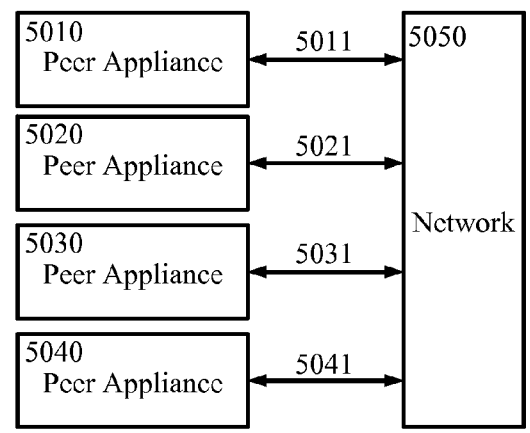
FIG. 50 shows appliance roles in the Ad Hoc team, where there is illustrated only one role, wherein each appliance has the same functionality and communicates with any of the other appliances as desired.

FIG. 50 shows appliance roles in the Ad Hoc team. As illustrated, in an Ad Hoc team, there is only one role. The team communicates over a common network, 5050 and connections 5011, 5021, 5031, 5041. Each peer appliance, 5010, 5020, 5030 and 5040, has the same role and functionality as the other appliances, and can selectively communicate with any one or multiple or all of the other appliances, as desired. The Ad Hoc of team gives each appliance a great deal of flexibility, and does not require the structure that the other types of teams have.

Figure 51:
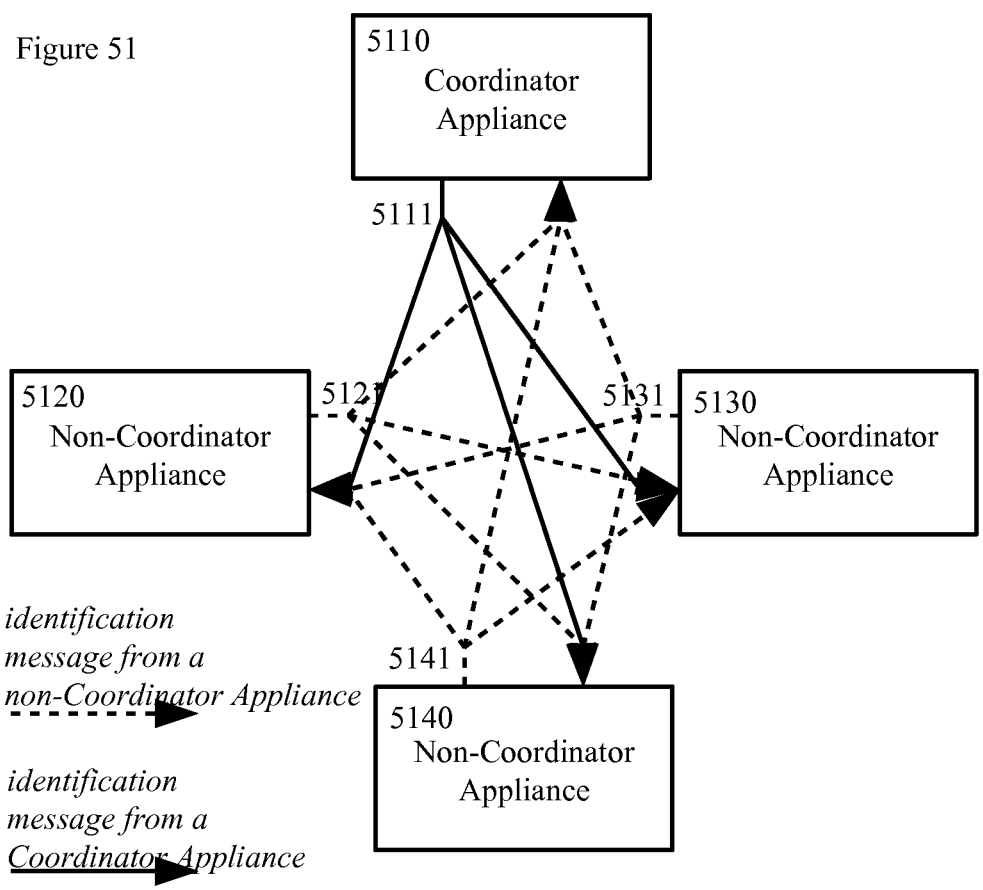
FIG. 51 shows identification messages in a team.

FIG. 51 shows identification messages in a team. A coordinator appliance, 5110, receives messages, 5121, 5131 and 5241, from all other appliances, 5120, 5130 and 5140, indicating what role and what capabilities each appliance has. The coordinator appliance can then send messages, 5111, to all the other appliances to indicate what role they have in a particular team and whether they are on the team and what that appliance functionality is. In some teams, there may be multiple coordinator appliances. In some embodiments, the team can be made up of all coordinator appliances (as in an Ad Hoc team). However in the case of a meeting team or education team, there is generally one coordinator appliance and all the rest are non-coordinator appliances.

Figure 52:
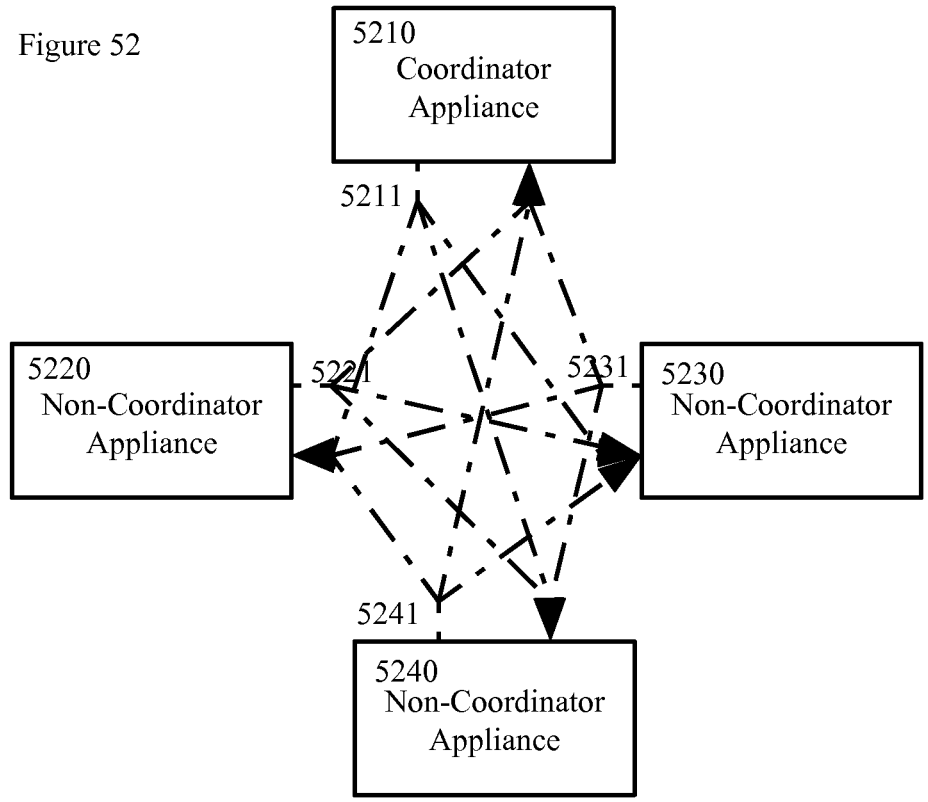
FIG. 52 shows conversational messages in a team.

FIG. 52 shows conversational messages in a team. Regardless of whether an appliance is a coordinator appliance, 5210, or a non-coordinator appliance, 5220, 5230 and 5240, each appliance has an ability to send messages, 5211, 5221, 5231 and 5241, between one appliance and one or all the other appliances. Whether a message is sent, or not, is dependent on the logic of the role and the team, and is controlled according to the role of the respective appliance on a respective team. For example, in general, the rule is that an appliance will not send a message to a appliance that is on a different team. Therefore, the logic for the roles in respective appliances determine which appliance a message is sent depending on what that other appliances' role is.

Figure 53:
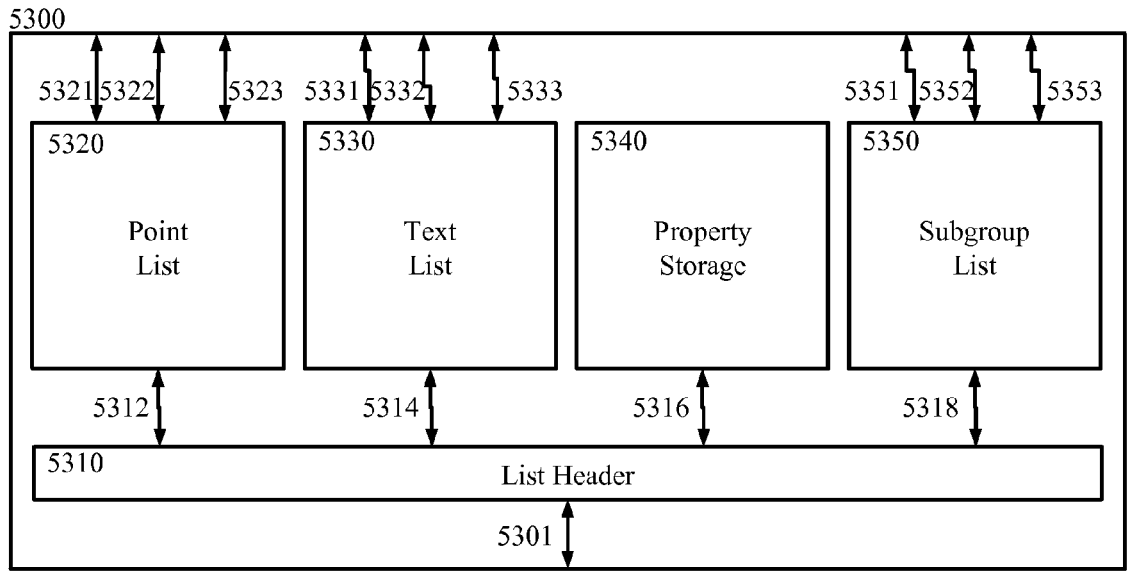
FIG. 53 illustrates an embodiment of a structure used to contain Layer Data.

FIG. 53 illustrates an embodiment of a group object, 5300. This is a container object for other group objects, text objects, point objects and properties stored in memory. The subgroup list, 5350, is coupled to the list header, 5310, via 5318 and contains an ordered list of pointers to a plurality of group objects as shown by links 5351, 5352 and 5353. While 3 links are shown here in the subgroup list, point list and text list any number of links can be in the list including none. The ordering of the subgroup list allows groups to be traversed in a specific order, this is important later when used to define drawing operations and the order that items are drawn. This list defines a group tree of expanding subgroups. The point list, 5320, is coupled to the list header, 5310, via 5312 and contains an ordered list of pointers to a plurality of point objects as shown by links 5321, 5322 and 5323. The point objects in the list define a vector that can be used to draw lines. The text list, 5330, is coupled to the list header, 5310, via 5314 and contains an ordered list of pointers to a plurality of text objects as shown by links 5331, 5332 and 5333. Each text object in the list is drawn with the provided text in the object and in the order in the text list. Property storage, 5340, provides for a value responsive to a property in property storage which is communicated via 5316. Any number of properties are available and subgroups can access the properties in any of their parents. A subgroup can redefine a specific property and then the subgroup will use that value instead of the value from the parent. In this manner, the text font, text color, text style, line width, line color, line style and other properties can be defined to control the appearance of the lines and text drawn. In addition, a visible property can be set which controls whether a group object is to be drawn or skipped. These properties are used later to define Data Layers (see FIG. 56).

Figure 54:
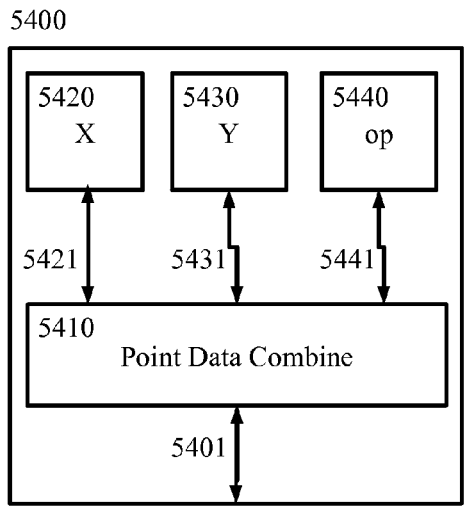
FIG. 54 illustrates an embodiment of a structure used to contain Layer Data vector information.

FIG. 54 illustrates an embodiment of a Point Object, 5400. The point object stores three items, an X location, 5420, Y location, 5430, and op, 5440, or operation to be performed. The operations minimally are move to and draw to but other draw operations are possible. When used in a point list, 5320, the point objects allow you to move to an XY location, draw to a plurality of other XY locations, and then start again with another move to as many times as desired to make a vector drawing. Note that properties in the property storage of one of the containing group objects can be used to modify how the lines are drawn (color, width, . . . ).

Figure 55:
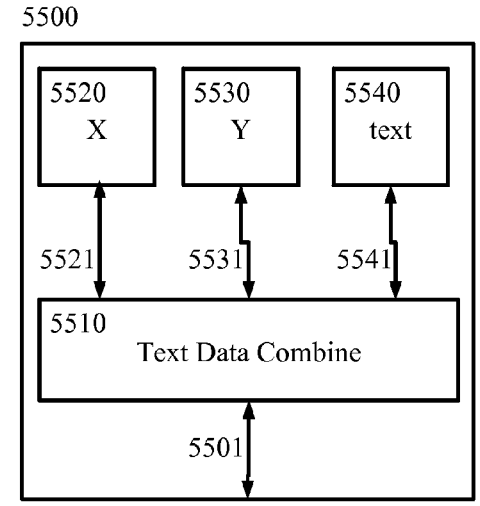
FIG. 55 illustrates an embodiment of a structure used to contain Layer Data textual information.

FIG. 55 illustrates an embodiment of a Text Object, 5500. The text object stores three items, an X location, 5520, Y location, 5530, and text, 5540. When used in a text list, 5330, the text objects allow you to place text at an XY location in the order of the text list. Note that properties in the property storage of one of the containing group objects can be used to modify how the text is drawn (font, style, color, . . . ). As with point objects, text objects in their respective list share the same property values. If you wish some objects to use different property values then place them in their own group object and link to it in the subgroup list.

Figure 56:
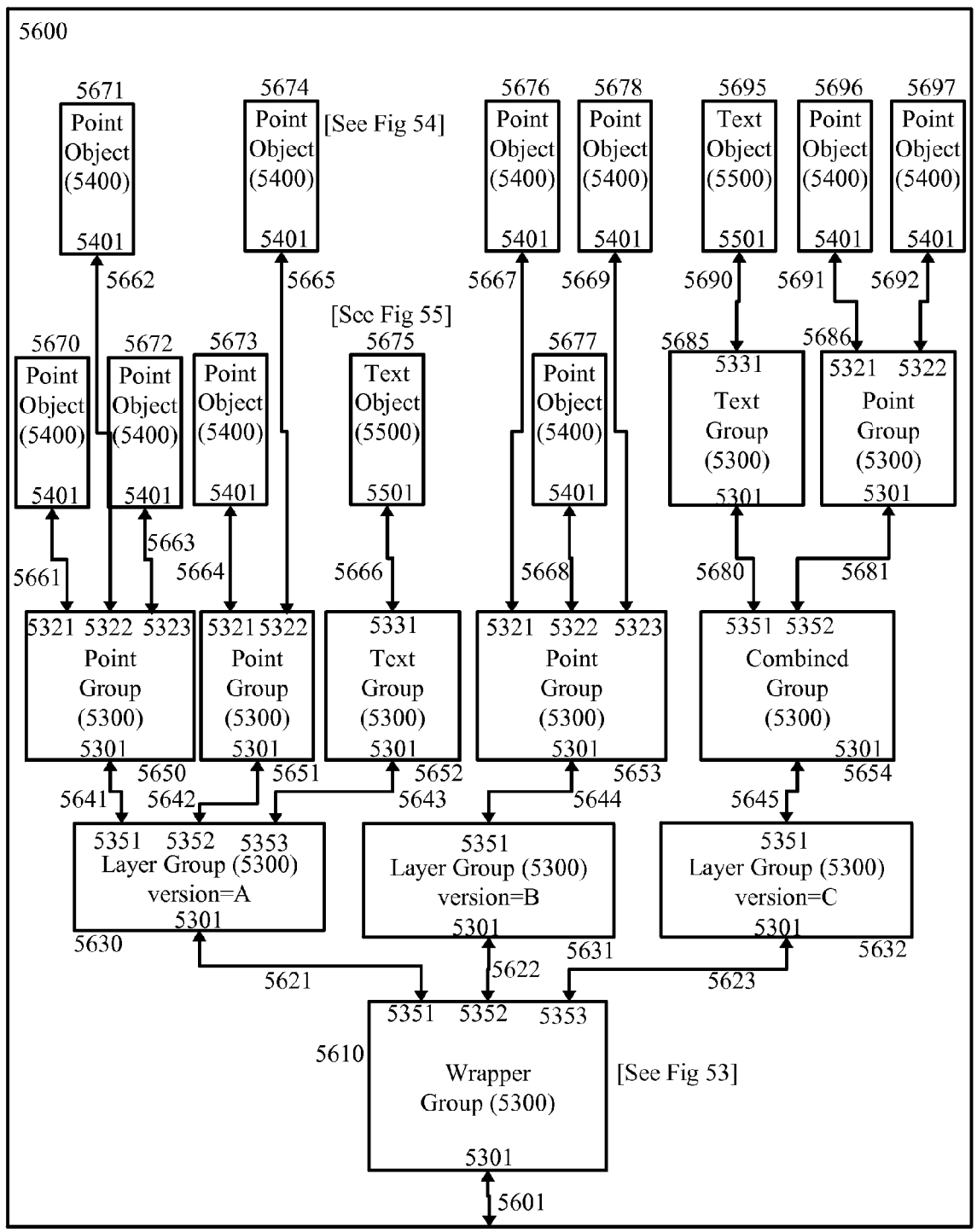
FIG. 56 illustrates an embodiment of a structure used to contain Layer Data combining group objects, point objects and text objects illustrated in FIGS. 53-55.

FIG. 56 illustrates an embodiment of a Annotation Wrapper Group, 5600. The annotation wrapper group provides an alternative embodiment for the combination of storage of layer data and Mapping Logic. This embodiment stores a part of the layer data except the common image stored elsewhere. The wrapper group, 5300, is entered from link 5601. The wrapper group has a subgroup list that points to group objects that define the Data Layers. Shown in this example are 3 Data Layers, layer group, 5630, 5631 and 5632, linked by 5641, 5642 and 5643 respectively, however any number of Data Layers can be defined. A version property is defined in each layer group. In this manner the layer data can be selected by traversing only the group tree where the version property matches the desired Data Layer. For instance, Data Layer A would be contained in layer group 5630, similarly Data Layer B would be contained in layer group 5631 and lastly Data Layer C would be contained in layer group 5632. Each layer group contains a subgroup list that provides the layer data for the Data Layer. Layer group, 5630, contains 3 subgroups: two point groups, 5650 and 5651, and one text group, 5652, coupled by 5641, 5642 and 5643 respectively. Layer group, 5631, contains just 1 subgroup: point group 5653 coupled by 5644. Layer group, 5632, contains just 1 subgroup: combined group 5654 coupled by 5645. The point groups, 5650, 5651, 5653 and 5686, and the text groups, 5652 and 5685, each have property values that define how the respective points and text are drawn. The point groups link their respective point lists, 5320, to point objects, 5670, 5671, 5672, 5673, 5674, 5676, 5677, 5678, 5696, 5697, via links 5661, 5662, 5663, 5664, 5665, 5667, 5668, 5669, 5691, 5692 respectively. The text groups link their respective text lists, 5330, to text objects, 5675 and 5695, via links 5666, 5690 respectively. The combined group, 5654, allows for a more complex structure of drawing items by containing a subgroup list with a text group and point group. This allows properties to be set once in the combined group, 5654, e.g., color property, and then the text and point groups, 5685 and 5686, do not need to set this property and will use the property in the combined group 5654. Also, the combined group, 5654, can set its visible property to hidden and then the text group, 5685, and point group, 5686, will not be drawn but can be easily drawn by changing the visible property in the combined group to show. Quite complex tree structures can be created for the layer data and only some of the simpler structures are shown, however, the structure shown in this example provides a very flexible and useful structure for layer data. For instance, when layer data B needs to be delivered to an element in the system for processing, only the link 5622, needs to be passed to access the data.

Figure 57:
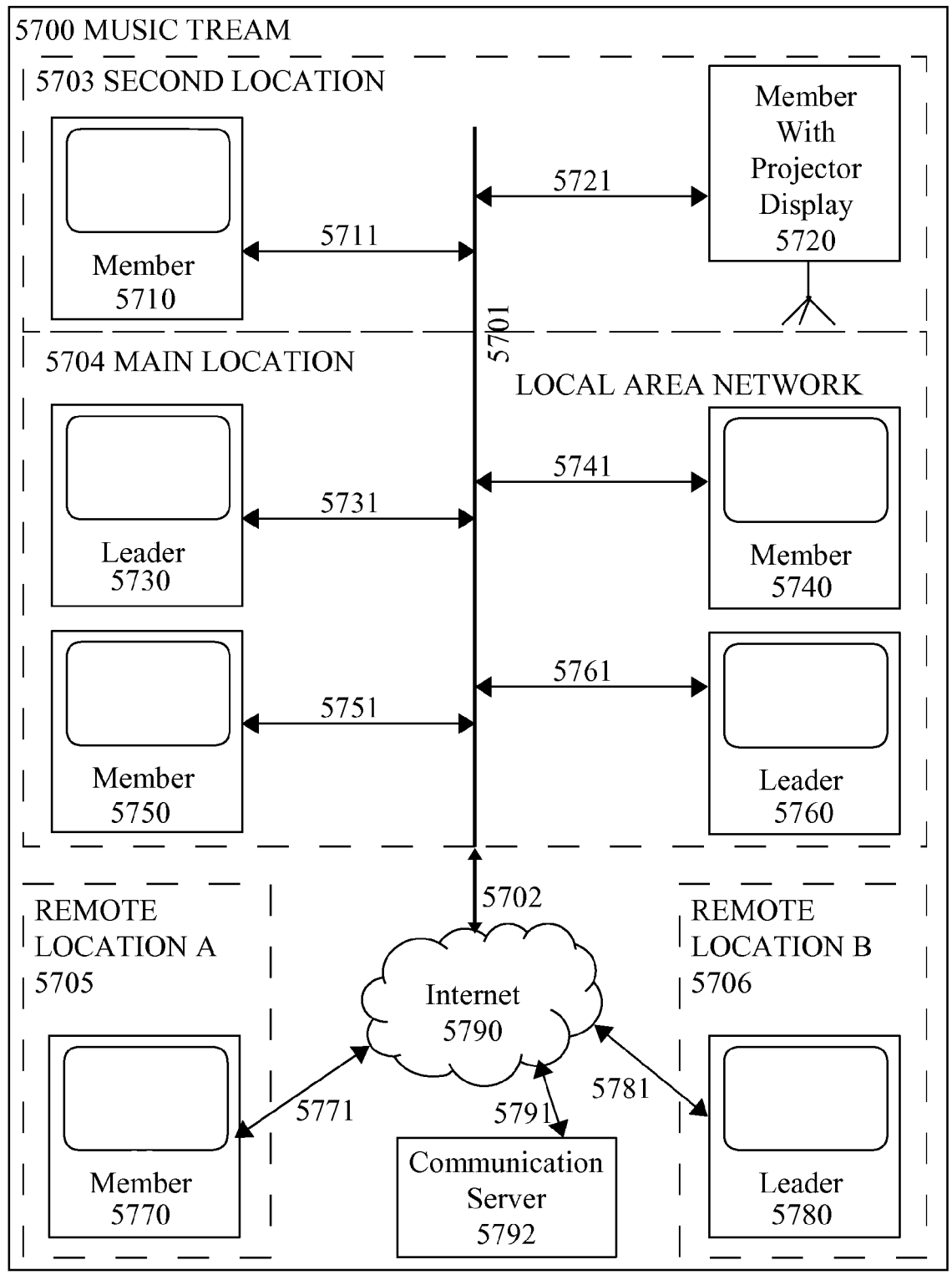
FIG. 57 illustrates a system of appliances connected via a local area network and the Internet in various physical locations.

FIG. 57 illustrates an embodiment of a Music Team. A music team is composed of one or more leader appliances, 5730, 5760 and 5780, and a number of member appliances, 5710, 5720, 5740, 5750 and 5770. The appliances are connected to a network. Appliances 5710, 5720, 5730, 5740, 5750 and 5760 are connected to a local area network, 5701, via connections 5711, 5721, 5731, 5741, 5751 and 5761 respectively. Although connected to the same local area network, appliances 5710 and 5720 are in a physically different room than appliances 5730, 5740, 5750 and 5760 but the operation is identical. The local area network, 5701, connects to the Internet, 5790, via connection 5702. Appliances 5770 and 5780 are in different remote location and connected to the Internet, 5790, via connections 5771 and 5781. The Internet connections generally do not allow the connections 5702, 5771 and 5781 to communicate directly. In some cases this is possible with the use of static IP addresses or VPN connections, and then the appliances 5770 and 5780 can communicate with the other appliances just as if they are in the same room. When this is not available, most of the time, then the connections 5702, 5771 and 5781 communicate with a static connection on the Internet 5791 which is coupled with a communication server, 5792. The communication server relays messages between the connections 5702, 5771 and 5781. In this manner, appliances 5770 and 5780 can communicate with the other appliances just as if they are in the same room. Some appliances may have special displays such as 5720, which has a projector attached and may users can view the display.

Figure 58:
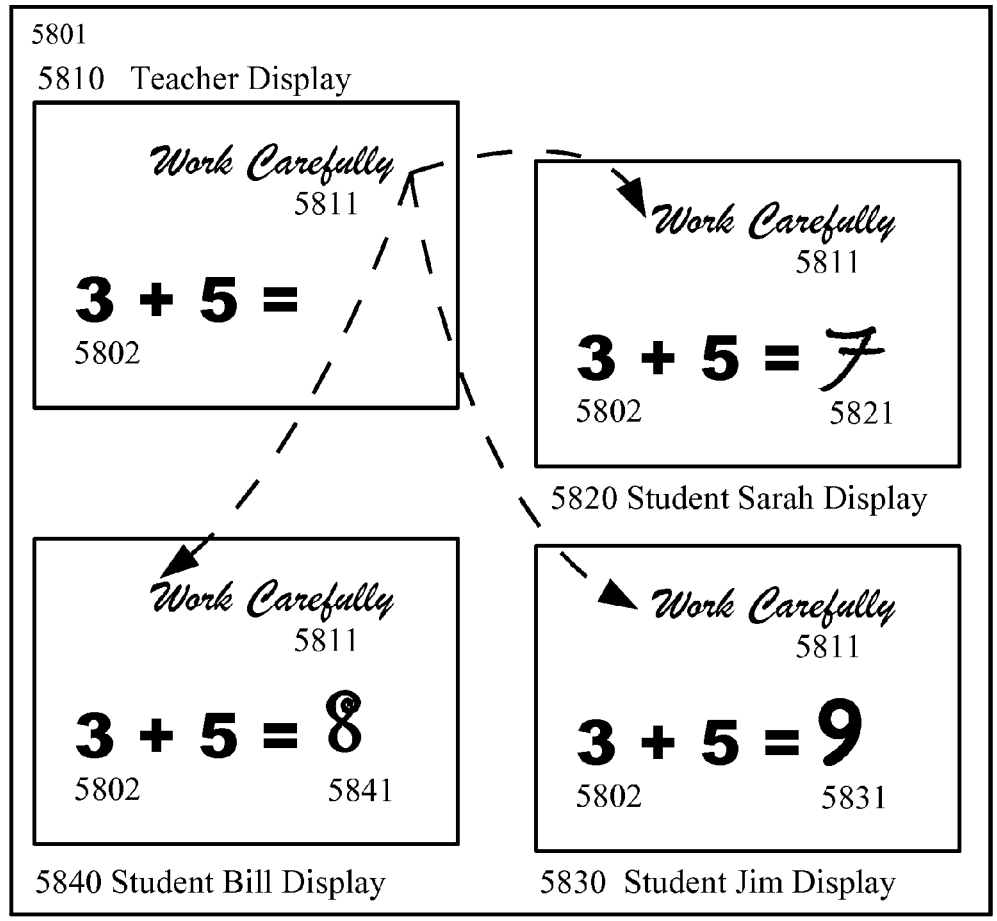
FIG. 58 illustrates an education team with one teacher and three students where the teacher is communicating to the entire classroom.

FIG. 58 illustrates an education team, 5801, with one teacher, 5810, and three students, 5820, 5830, 5840, displays where the teacher is communicating to the entire classroom. All appliances view the background image, 5802, as the Base Data Layer. The teacher can write an annotation, 5811, on their appliance in the Teacher Data Layer, (in the example shown, the word "Work Carefully"). Each student is also viewing the Teacher Data Layer so each student immediately sees the annotation, 5811, on their appliance also. Each student appliance has a unique Data Layer that they view and edit. Each student sees the Teacher Data Layer and their own Data Layer. Thus, Sarah, 5820, views the Sarah Data Layer and the Teacher Data Layer. Jim, 5830, views the Jim Data Layer and the Teacher Data Layer. And Bill, 5820, views the Bill Data Layer and the Teacher Data Layer. Each student is doing the assignment as well. Student Sarah, 5820, wrote "7", 5821, as her answer in the Sarah Data Layer. Student Jim, 5830, wrote "9", 5831, as his answer in the Jim Data Layer. Student Bill, 5830, wrote "8", 5841, as his answer in the Bill Data Layer. In this mode of operation the teacher does not see the students' work because the teacher only views the Teacher Data Layer.

Figure 59:
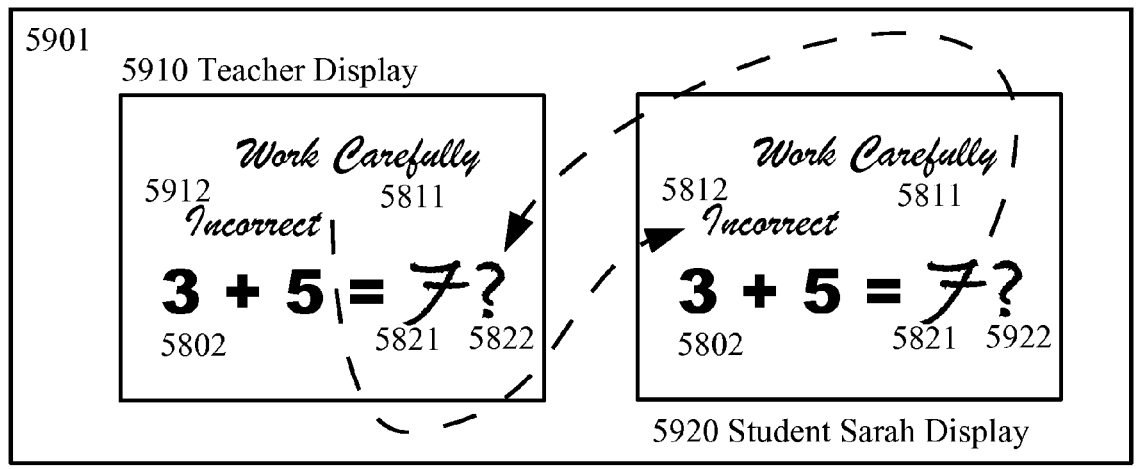
FIG. 59 illustrates an education team with a teacher interacting with a student one-on-one.

FIG. 59 illustrates an education team, 5901, with a teacher, 5910, interacting with a student, 5920, one-on-one. Illustrated is Sarah which is viewing the Sarah Data Layer and Teacher Data Layer. The teacher is viewing the Teacher Data Layer and a specific student's Data Layer, in this example the same as Sarah, 5920. Both the student and teacher edit the Sarah Data Layer. This allows the teacher and the student to make annotations in the specific student's Data Layer which are visible by both, but not the entire classroom. In this illustration, the teacher wrote "Incorrect", 5912, which is also viewed on the Sarah display 5920. The student responded with a "?", 6022, which the teacher views on their display, 5910. None of the other students are viewing this interaction between Sarah and the teacher so Sarah can be more confident in asking a question. Nor are the other students bothered by the Sarah/teacher interaction.

FIG. 60 illustrates an education team, 6010, with one teacher, 6010, and three students, 5820, 5830 and 5840, where the teacher is monitoring the entire classroom's progress. The student displays are the same as in FIG. 58. This illustrates an embodiment of a Teacher multi-view screen. The display screen, 6010, is shown with 3 reduced size images of the screens of various appliances. Shown is a 2 by 2 grid of reduced size display screen images but a different grid is possible such as 3 by 3, 4 by 4, 5 by 5, etc. The preferred embodiment is uses the same division vertically as horizontally because the aspect ratio of the reduced images is the same as the original. Alternatively, 3 by 4, 2 by 3 and other divisions are possible. Alternatively, some of the reduced images can overlap on another and when highlighted they move to the top of the display so they can be fully seen. The teacher can view a version of each student on a portion of the teacher display, 6010. Each student version uses a scaled version of the background image, 5802, as a Data Layer as well as the teacher and specific student layer. In this illustration, student display, 5820, is shown in the teacher display, 6010 as 6020. Student display, 5830, is shown in the teacher display 6010 as 6030. Student display, 5840, is shown in the teacher display 6010 as 6040. The teacher display, 5810 as shown in FIG. 58, is shown in the teacher display 6010 as 6010. When a student modifies their own Data Layer, the teacher is updated with the annotations made by the student in their part of the display. The teacher can select one of the portions of the teacher display, 6020, 6030 or 6040, to enter the mode as shown in FIG. 59 for a teacher-student one-on-one session. The teacher can select the portion of the teacher display, 6010, to enter the mode as shown in FIG. 58 for working with the entire classroom.

FIG. 61 illustrates a social team where the owner, Frankie, 6103, is viewing all the messages 6111, 6112, 6113, 6114, 6115, 6116, 6117, 6118, 6119, 6120, 6121, 6122, 6123, 6124, 6125, 6126, 6127 and 6128 on a display 6101. These messages are displayed in various combinations in FIGS. 62, 63, 64, 65, 66, 67, 68, 69 and 70, responsive to the user, 6103 in this figure, and selections by the user. Frankie is a recording artist and does concerts. He is using Chat to keep in touch with his fans and his manager, John. This chat team is composed of three entities: user and owner (Frankie), user (John) and a Groupie subteam. The Groupie subteam is composed of many users, in this example: Mary, Jim, Sally, Jane, David, Fred, Randy, Kim and Bill and FrankS. User Frankie can use two different Data Layers, Frankie and FrankS As the owner, Frankie can has control of who can join, what Data Layers they can view and what Data Layers they can modify. John is allowed to view all Data Layers but does not have a Data Layer in the Groupie subteam. Frankie can see everything that is going on but only Frankie will be able to see his messages. The Groupie subteam users each have a separate Data Layer but they can only view Data Layers in the Groupie subteam. The Groupie subteam can communicate with each other and can communicate with Frankie only if Frankie uses the FrankS Data Layer. In this figure the user, Frankie, 6103, has selected to view all the messages available.

FIG. 62 illustrates a social team where the user, Frankie 6203, is viewing messages, 6111, 6114, 6120, 6125 and 6128 between himself and his manager, John 6204, on display 6201. Frankie can keep in touch with his manager, John, without the clutter of the fans. His responses to John are not viewed by the fans. The Data Layers for the Groupie subteam are not displayed, including FrankS Data Layer. The John Data Layer is visible because the user has requested that Data Layer. The Frankie Data Layer is visible because that is the user's Data Layer. They are combined by the display logic, 3900 (see FIG. 39).

FIG. 63 illustrates a social team where the user, Frankie 6303, is viewing is messages 6112, 6113, 6115, 6116, 6117, 6118, 6119, 6121, 6122, 6123, 6124, 6126, and 6127 on a display 6301. Frankie can keep in touch with his fans, his responses or messages to the fans are seen by everyone. All the Data Layers in the subteam, Groupies, 6301, are shown. The Frankie Data Layer and John Data Layer are not visible. John's messages, 6111, 6120, 6128 are in the John Data Layer and are thus not shown. Only the message, 6124, from Frankie in the FrankS Data Layer is shown. Messages 6114 and 6125 from Frankie are not shown because they are in the Frankie Data Layer. These messages combined by display logic 3900.

FIG. 64 illustrates a social team where the user, Frankie 6403, is viewing threads of messages that he has participated in. Frankie can see the message threads that he has participated in. Here is a thread with his manager and with the fans. Note how this eliminates extraneous messages. A more expanded view of the thread could also be shown (see FIG. 70). All Data Layers are shown but only messages in all layers that are directly referenced by a Frankie Data Layer or FrankS Data Layer message are shown. One thread of messages is shown because of Frankie's messages 6114 and 6125 in the Frankie Data Layer referenced to John. John starts the thread of messages with message 6111 to Frankie to which Frankie responds with message 6114. John responds with message 6125 and Frankie finishes the thread of messages with message 6128. This single thread of messages contains two messages from Frankie but any number could be included. A second thread of messages is shown because of Frankie's message 6124 in the FrankS Data Layer to Jane's message 6119. David's message 6118 is included because it was responded to by Jane's message 6119. Russ' message 6117 is included because it was responded to by message 6118. Jane started the thread of messages with message 6116 which was responded to by message 6116. Only one message, 6124, from Frankie is in this thread of messages. Only messages directly responded to Frankie's message 6124 in the FrankS Data Layer are included by the display logic 3900.

FIG. 65 illustrates a social team where the user, John 6503, is viewing all the messages. John can keep track of everything going on the in the chat room for Frankie Since John has viewing rights for all Data Layers, all Data Layers are shown. The messages shown are the same as in FIG. 61. Only the user 6503 is different in display 6501 from the display 6101 with user 6103.

FIG. 66 illustrates a social team where the owner, John 6603, is viewing messages between himself and Frankie John can keep in touch with Frankie without the clutter of the fans. His responses to Frankie are not viewed by the fans. The Frankie Data Layer is visible because the user has requested that Data Layer. The John Data Layer is visible because that is the user's Data Layer. The Data Layers for the Groupie subteam are not displayed, including FrankS Data Layer. They are combined by the display logic, 3900.

Figure 67:
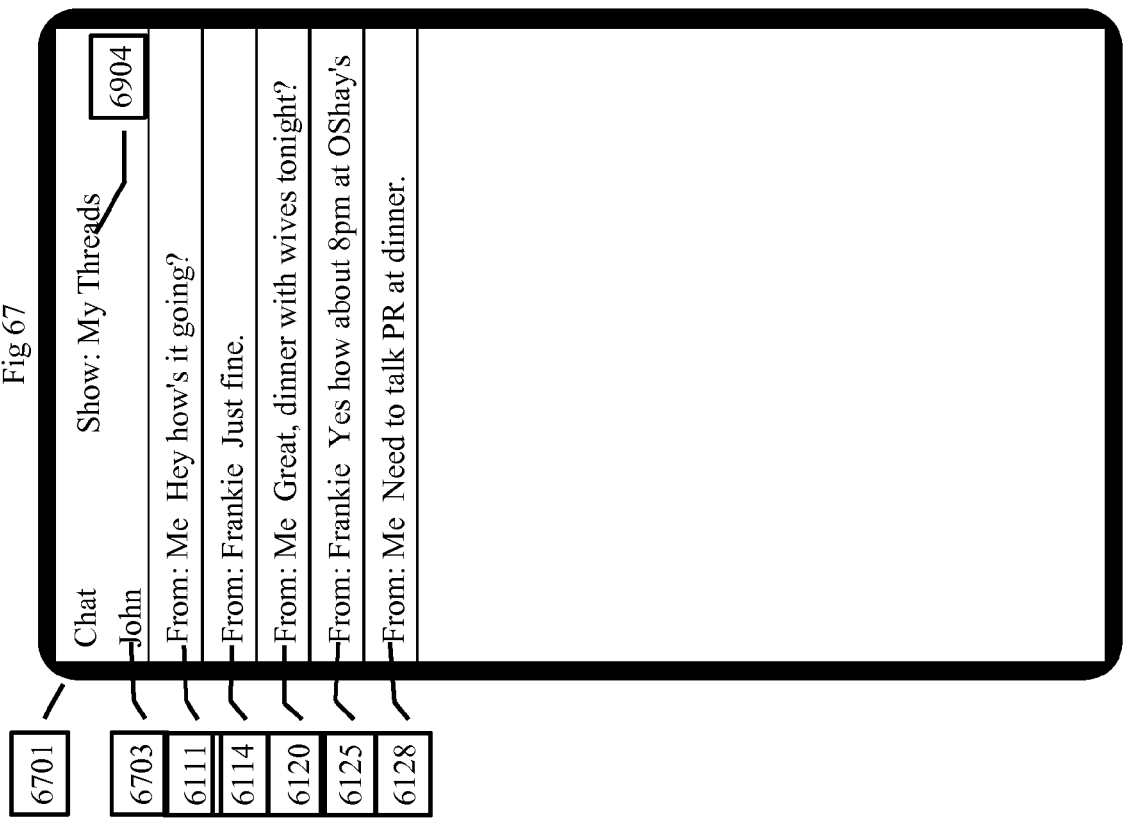

FIG. 67 illustrates a social team where the owner, John 6703, is viewing threads of messages that he has participated in. All Data Layers are shown but only messages in all layers that are directly referenced by a John Data Layer are shown. One thread of messages is shown because of Frankie's messages 6114 and 6125 in the Frankie Data Layer referenced to John. John starts the thread of messages with message 6111 to Frankie to which Frankie responds with message 6114. John responds with message 6125 and Frankie finishes the thread of messages with message 6128. This single thread of messages contains three messages from Frankie but any number could be included. Not illustrated in this figure is the possibility that John could have responded to a message in the Groupie subteam in the John Data Layer. For instance, John, could have responded to message 6127 with a message of "We should remove this spammer". This response would only be visible to Frankie and not to anyone in the Groupie subteam (except Frankie). This would create a thread of messages that John participated in and would be shown in this display, 6701, if John had responded to a message as such.

Figure 68:
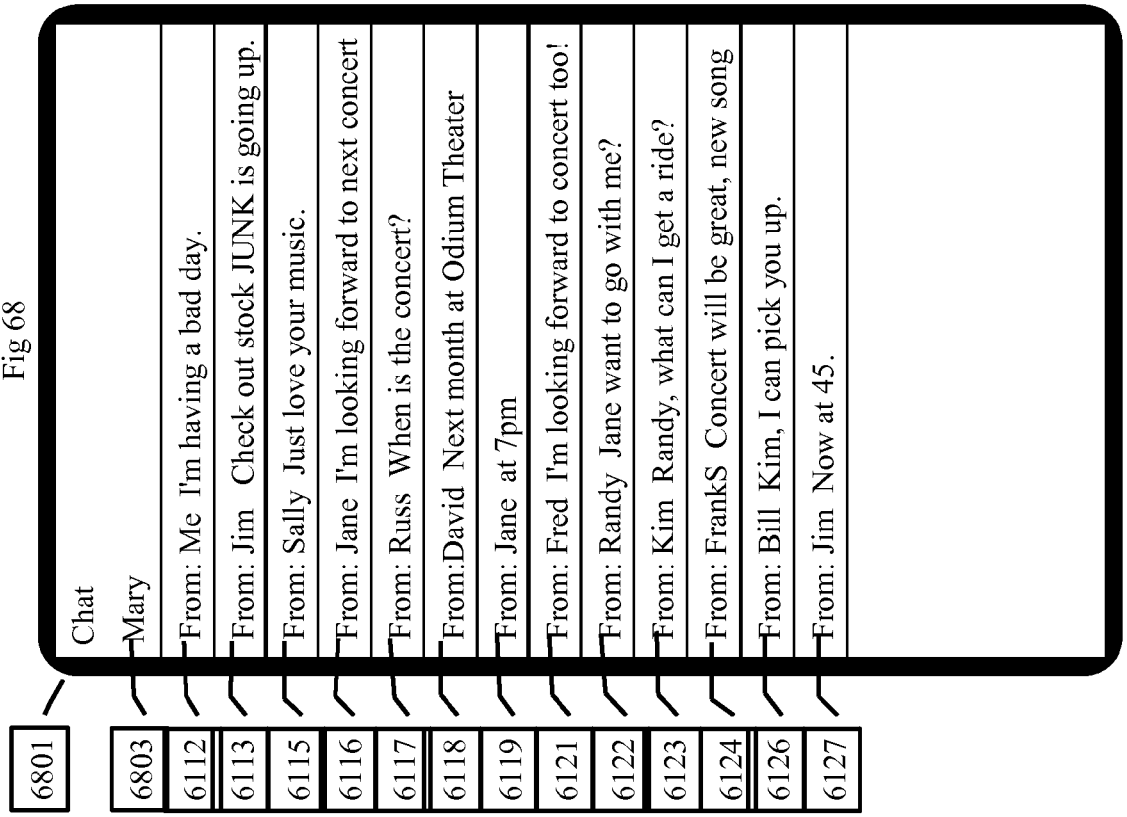
FIG. 68 illustrates a social team where the owner, Mary, is viewing all the messages available to her.

FIG. 68 illustrates a social team where the user, Mary 6803, is viewing all the messages available to her. Mary is one of the fans. She and the other members of the Groupies subteam can't view the private messages between Frankie and John. Since Mary is only a member of the Groupies subteam, she can only have the Groupies subteam member Data Layers visible. The Frankie Data Layer and John Data Layers are not visible but the FrankS Data Layer is visible. Thus the messages 6112, 6113, 6115, 6116, 6117, 6118, 6119, 6121, 6122, 6123, 6124, 6125, 6126 and 6127 on a display 6801.

FIG. 69 illustrates a social team where the user, Mary 6903, is viewing all the threads she has participated in. Since Mary is only a member of the Groupies subteam, she can only have the Groupies subteam member Data Layers visible. The Frankie Data Layer and John Data Layers are not visible but the FrankS Data Layer is visible. Mary only sent one message 6112. No one responded to said message and so only said message is displayed. When and if someone does, she'll be able to easily see the response in context.

FIG. 70 illustrates a social team where the user, Frankie 7003, is viewing threads of messages that he has participated in with a detailed view, 7004, on display 7001. Frankie can see expanded messages (all branches) of a thread he participated in. This is similar to FIG. 64. The element 6404 in FIG. 64 indicates a normal My Threads view and the element 7004 in FIG. 70 indicates a My Thread detail. There is no difference in the thread of messages that include messages, 6111, 6114, 6120, 6125 and 6128. The second thread has messages 6121, 6122, 6123 and 6126 also included in addition to the messages in FIG. 64. Message 6121 is included because it is in response to message 6116 which was directly included in the normal My Threads view. Message 6122 is included because it is in response to message 6119 which was directly included in the normal My Threads view. Message 6123 is included because it is in response to message 6122. Message 6126 is included because it is in response to message 6123. These messages are combined by the display logic, 3900.

FIG. 71 illustrates an individual Data Layer, 7100, that contains layer data that is segmented into Layer Data Elements, 7170, 7171, 7172, 7179. This illustration shows four (4) Layer Data Elements making up the layer data but any number of Layer Data Elements are possible. Each Layer Data Element contains context and content information. Layer Data Element 7170 contains an element context, 7130 and an element content, 7140. Layer Data Element 7171 contains an element context, 7131 and an element content, 7141. Layer Data Element 7171 contains an element Context, 7131 and an element content, 7141. Layer Data Element 7172 contains an element context, 7132 and an element content, 7142. Layer Data Element 7179 contains an element context, 7139 and an element content, 7149. The context information, 7160, 7161, 7162, 7169, from each Layer Data Element, 7170, 7171, 7172, 7179, is coupled to the Layer Data Element selection, 7110. In one embodiment, Part, 7103, is responsive and coupled to 1612, 1622, 1632 in FIG. 16. In another embodiment, Part, 7103, is responsive and coupled to 1712, 1722, 1732 in FIG. 17. Part provides an input to the Layer Data Element Selection, 7110, which selects one or more Layer Data Elements within the layer data, 7100. The selection of an element is indicated on signal 7120 for Layer Data Element 7170, 7121 for Layer Data Element 7171, 7122 for Layer Data Element 7172, 7129 for Layer Data Element 7179. Part, 7103, can specify more than one Layer Data Element. The specification provided by Part may include "Select all Layer Data Elements", "Select no Layer Data Elements", "Create a new Layer Data Element", or a selection based on comparison with context information from the respective Layer Data Elements. Successful comparisons will cause the layer element selection signals 7120, 7121, 7122, 7132 to be asserted for the respective Layer Data Element. Element selection signal 7120 is coupled to element context, 7130, and element content, 7140. Element selection signal 7121 is coupled to element context, 7131, and element content, 7141. Element selection signal 7122 is coupled to element context, 7132, and element content, 7142. Element selection signal 7129 is coupled to element context, 7139, and element content, 7149. Element contexts, 7130, 7131, 7132, 7139, output the context information on context layer data out, 7171, and is coupled to Combine Context And Context Data, 7170. Element Contents, 7140, 7141, 7142, 7149, output the content information on Content Layer Data Out, 7172, and is coupled to Combine Context And Content Data, 7170. Combine Context And Context Data provides Data Out, 7102, that contains all the context and content information of all the Layer Data Elements that are asserted by signals 7120, 7121, 7122, 7129. If none of the signals 7120, 7121, 7122, 7129, are asserted then Data Out, 7102, contains no data. In one embodiment, Data Layer Access, 1740 via 1712, 1722 or 1732 in FIG. 17 is responsive and coupled to Data Out, 7102. In another embodiment, Data Layer Access, 1640 via 1612, 1622 or 1632 in FIG. 16 is responsive and coupled to Data Out, 7102. Data In, 7101, provides replacement layer data for a Layer Data Element, 7170, 7171, 7172 or 7179. Data In is responsive to and coupled to Data Layer Access, 1710, via 1711, 1721 or 1731 in FIG. 17. Data In, 7101, is coupled to Separate Context And Content Data, 7150. Separate Context And Content Data divides the data into two parts, the context information which is output on Context Layer Data In, 7151, and content information which is output on Content Layer Data In, 7152. Context Layer Data In, 7151, is coupled to the Layer Data Elements to Element Contexts, 7130, 7131, 7132, 7139. Content Layer Data In, 7152, is coupled to the Layer Data Elements to Element Contents, 7140, 7141, 7142, 7149. Part, 7103, asserts a single signal, 7120, 7121, 7122 or 7129, to one of the Layer Data Elements. The selected Layer Data Element, 7170, 7171, 7172 or 7179, replaces the information in its respective Element Context (7130, 7131, 7132 or 7139) and Element Content (7140, 7141, 7142 or 7149) with Context Layer Data In and Content Layer Data In. If "Create a new Layer Data Element" is specified by Part, 7103, then a new Layer Data Element is created and Context Layer Data In and Content Layer Data In is stored in the said new Layer Data Element. Data Out, 7102, contains a duplicate of the Data In, 7101, when Data In is used to create or replace Layer Data Element layer data.

What is claimed is:

1. A system for collaborating among a plurality of users each said user utilizing an associated computing appliance having a display apparatus and an input apparatus providing an output of data having an associated image and associated with said user providing the input, the system comprising:

memory logic providing structured storage in a plurality of parts of a non-transitory memory;

mapping logic exclusively associating each said user with at least one of the plurality of parts to provide for storage of the data associated with said user;

input logic permitting at least two of the users to provide concurrent input of the data while viewing a same display presentation image on the display apparatus of the computing appliance associated with each said user;

storage logic providing selective storage and retrieval of the data associated with each said user, for at least two said users, in the memory responsive to the mapping logic and the input logic; and, display logic providing an updated display presentation on the display apparatus of at least one of the computing appliances, responsive to the mapping logic and the storage.

2. The system as in claim 1, wherein the plurality of parts of memory are comprised of a plurality of storage locations that are associated together to form an associated data layer that provides storage associated with the user that provided the input of the data being stored.

3. The system as in claim 2, wherein the mapping logic associates each of the users to a unique one of the data layers; and wherein the storage logic provides storage of the data in the associated data layer responsive to the mapping logic;

wherein the display logic creates the updated display presentation at at least one of the computing appliances, responsive to the mapping logic and the storage.

4. The system as in claim 2, wherein the mapping logic is comprised of a mapping memory storing a plurality of user layer list comprising one said user layer list associated with each of said user;

wherein each said user layer list is comprised of a respective list of pointers for each of the plurality of users, pointing to specific ones of the data layers associated and defining which of the data layers are to be associated with each said respective user; and wherein there are a plurality of separate user display apparatus for each of a plurality of respective said users providing a respective local display presentation on each said local user display apparatus responsive to the respective user layer list associated with said user and to the memory.

5. The system as in claim 2, wherein the mapping logic is comprised of a table memory storing a mapping table providing mapping of each of the users to the associated data layer.

6. The system as in claim 1, further comprising:

facilitator logic creating a user mapping associating each of the users with one of the computing appliances and with the input of the data from said computing appliance;

wherein the mapping logic is responsive to the facilitator logic.

7. The system as in claim 1, further comprising:

user selection logic selecting at least one of the users as selected users;

wherein the display logic provides the updated display presentation on the display apparatus of at least one of the computing appliances, responsive to the mapping logic and the parts of a memory associated with the selected users.

8. The system as in claim 1,
selection logic selecting from the associated images associated with at least one of the users to provide selected images;
wherein the display logic provides the updated display presentation on the display apparatus of at least one of the computing appliances, responsive to the mapping logic and the parts of a memory associated with the selected images.

9. The system as in claim 1,
wherein the display logic provides
a first display of a specific image,
then a display of annotations as input by at least one said user to said user, then a display of the annotations as input by at least two of the users.

10. The system as in claim 2,
wherein the mapping logic provides storage of a plurality of user layer lists, each said user layer list associated with one said user;
wherein each said user layer list comprises a pointer list indexing each said user to be associated with one said data layer;
wherein the data, representative of displayable information is retrieved from at least one said data layer associated with one said user responsive to the user layer list;
wherein the display logic combines the displayable information for each respective user responsive to the respective user layer list for said each respective user, to provide data for combined displayable information for said each respective user and provides a presentation for each said respective user of the combined displayable information for each said respective user.

11. The system as in claim 1,
wherein the plurality of parts of memory are comprised of a plurality of data layers;
wherein the mapping logic exclusively associates each said user with at least one of the data layers to provide storage of the data associated with said user;
the system further comprising:
list logic providing a plurality of user layer lists comprised of one said user layer list for each of a plurality of respective said users;
wherein each said user layer list is comprised of a respective list of pointers for each of the plurality of users, pointing to specific ones of the data layers and defining which of the layers are to be associated with each said respective said user responsive to the mapping logic; and
wherein the display logic provides the updated display presentation on a plurality of the display apparatus each providing a separate display presentation responsive to the respective said user layer list, the memory, and the mapping logic.

12. The system as in claim 11,
wherein the memory is global memory located at a centralized location;
wherein the plurality of data layers is comprised of a plurality of global data layers;
wherein each said user layer list is comprised of a respective list of pointers for each of the plurality of users, pointing to specific ones of the global data layers and defining which of the global data layers are to be associated with said associated user; and
wherein said local display presentation is provided responsive to the user layer list and the global memory.

13. The system as in claim 11, further comprising:
input apparatus providing annotation data having a corresponding display, provided responsive to an input of annotations by a respective said user as made while viewing a display of a base document for each of two said users providing the input;
wherein the memory stores the annotation data in a mapped structure wherein the stored annotation data is associated with the respective said user making the input of said annotation data and is stored in the data layer that is associated with the user providing the input.

14. The system as in claim 11, further comprising:
user selection logic, providing selection of at least one of the users as selected users;
wherein the local display presentation is provided responsive to the annotation data stored in the data layers associated with the selected users.

15. The system as in claim 11,
wherein the memory is global memory located at a centralized location;
wherein the memory logic, input logic and storage logic are located at the centralized location.

16. The system as in claim 11,
wherein the display logic provides a display output to each of at least two said users, of an individualized said updated presentation, provided responsive to the memory and to the user layer lists associated with each said user.

17. The system as in claim 11,
wherein each said list of pointers is further comprised of a control flag associated with each of the data layers in said list of pointers; and
wherein said control flag is utilized to selectively enable, at any given time, one of the data layers to be utilized for storing the data as input by the associated said user in the associated said data layer responsive to said list of pointers.

18. The system as in claim 1,
wherein the display logic concurrently provides a different said updated display presentation for at least two of the users.

19. The system as in claim 1,
wherein the plurality of parts of memory are comprised of a plurality of data layers;
wherein the mapping logic exclusively associates each said user with at least one of the data layers to provide storage of the data associated with said user;
the system further comprising:
list logic providing a plurality of user layer lists comprised of one said user layer list for each of a plurality of respective said users;
list memory, storing a plurality of user layer lists for each of a plurality of said users, each of the plurality of user layer lists comprising a pointer list indexing said respective user to a plurality of respective associated said data layers;
wherein the storage logic selects the associated said data layers associated with each said user layer list responsive to the respective pointer list for each said respective user;
wherein the display logic is responsive to the user layer list for each respective said user, to provide the updated display presentation to said respective said user, responsive to combining the data for all of the data layers retrieved for each respective said user responsive to the layer list associated with said respective said user, so as to create combined layer display information for said respective said user; and wherein the updated display presentation for said respective said user is provided responsive to the combined layer display information for said respective said user.

20. A method for collaborating among a plurality of users, each said user utilizing an associated computing appliance having a display apparatus and an input apparatus providing an output of data having an associated image and associated with said user providing the input, the method comprising:
providing structured storage in a plurality of parts of a non-transitory memory;
exclusively associating each said user with at least one of the plurality of parts to provide for storage of the data associated with said user;
permitting at least two of the users to provide concurrent input of the data while a same display presentation image is provided for viewing on the display apparatus of the computing appliance associated with each said user;
providing selective storage and retrieval of the data associated with each said user, for at least two said users, in the memory responsive to the exclusively associating and the input of the data; and,
providing an updated display presentation on the display apparatus of at least one of the computing appliances, responsive to the exclusively associating and the storage.

21. The method as in claim 20,
wherein the plurality of parts of memory are comprised of a plurality of storage locations that are associated together to form an associated data layer that provides storage associated with the user that provided the input of the data being stored.
wherein the memory is structured for storage of the data for a plurality of the users as layer data for each user stored in a plurality of the data layers comprised of at least two parts of the memory providing storage associated as a data layer;
wherein the mapping logic associates each of the users to a unique one of the data layers; and
wherein the storage logic providing storage of the data in the associated data layer responsive to the mapping logic; and
wherein the display logic creates a display presentation at at least one of the computing appliances, responsive to the exclusive associating and the storage.

22. The method as in claim 21, further comprising:
selecting which of the data layers are enabled data layers associated with each said user;
retrieving at least some of said data from the enabled data layers as selected data;
wherein the providing the updated display presentation is responsive to the selected data.

23. The method as in claim 21,
wherein the mapping logic is comprised of a mapping memory storing a plurality of user layer lists comprising one said user layer list associated with each said user;
wherein each said user layer list is comprised of a respective list of pointers pointing to specific ones of the data layers associated and defining which of the data layers are to be associated with each respective said user for each of the plurality of users; and
wherein each of a plurality of separate user display apparatus for each of a plurality of said users provide a respective said local display presentation on said separate user display apparatus responsive to the respective said user layer list and the memory.

24. The method as in claim 23,
wherein each said list of pointers is further comprised of a control flag field associated with each of the data layers, the method further comprising:
utilizing said control flag field to selectively enable at any given time, one of the data layers to be an enabled data layer that is utilized to provide the data associated therewith to use in providing the updated display presentation.

25. The method as in claim 20, further comprising:
enabling as enabled layers, at least one said data layer as pointed to in the user layer list as associated with each said user, for storage of the data associated with each said user in the layer associated with said user; and,
providing the updated display presentation responsive to the data in the enabled layers.

26. The method as in claim 20, further comprising:
enabling as an enabled layer, at least one said data layer as pointed to in the user layer list as associated with each said user, to provide for storage of the data as input by the associated said user providing the input;
wherein the data as input by each said user is stored in the data layer pointed to in said user layer list that is associated with said user.

27. A system for supporting collaboration at a centralized location among a plurality of users at remote locations remote to the centralized location, each said user utilizing an associated computing appliance having a display apparatus and an input apparatus providing an output of data having an associated image and associated with said user providing the input, the system comprising:
memory logic providing structured storage in a plurality of parts of a non-transitory memory;
mapping logic at the centralized location exclusively associating each said user with at least one of the plurality of parts to provide for storage in the memory of the data associated with said user;
input logic at the centralized location permitting at least two of the users to provide concurrent input at the remote locations, of the data, while a same display presentation image is provided for viewing at the remote location on the display apparatus of the computing appliance associated with each said user;
storage logic providing selective storage of the data associated with each said user, for at least two said users, in the memory responsive to the mapping logic and the input logic; and,
display logic providing an updated display presentation on the display apparatus of at least one of the computing appliances, responsive to the mapping logic and the storage logic.

28. The system as in claim 27,
wherein the memory logic provides the structured storage at the centralized location.

29. The system as in claim 27,
wherein the display logic is located at the centralized location.

30. The system as in claim 27,
wherein the memory is located at the centralized location.

31. The system as in claim 27,
wherein the memory is distributed and located in a plurality of the computing appliances.

32. The system as in claim 1,
wherein the memory is located at a centralized location, and in a plurality of the computing appliances at remote locations remote to the centralized location.

33. The system as in claim 27,
wherein the memory is located in the centralized location and is located in a plurality of the computing appliances.

34. The system as in claim 27,
wherein the display logic provides an updated display presentation on the display apparatus of at least two of the users, responsive to the mapping logic and the storage.

35. The system as in claim 27,
wherein the storage logic is located at the centralized location.

* * * * *